United States Patent
Ruat et al.

(10) Patent No.: US 9,073,835 B2
(45) Date of Patent: Jul. 7, 2015

(54) N-ACYLTHIOUREA AND N-ACYLUREA INHIBITORS OF THE HEDGEHOG PROTEIN SIGNALLING PATHWAY

(75) Inventors: Martial Ruat, Orsay (FR); Hélène Faure, Gif-sur-Yvette (FR); Elisabeth Traiffort, Paris (FR); Angèle Schoenfelder, Lampertheim (FR); André Mann, Ostwald (FR); Maurizio Taddei, Monteriggioni (IT); Antonio Solinas, Siena (IT); Fabrizio Manetti, Castelnuovo Berardenga (IT)

(73) Assignees: Centre National De La Recherche Scientifique, Paris (FR); Universite De Strasbourg, Strasbourg Cedex (FR)

( * ) Notice: Subject to any disclaimer, the term of this patent is extended or adjusted under 35 U.S.C. 154(b) by 598 days.

(21) Appl. No.: 12/988,975

(22) PCT Filed: Apr. 16, 2009

(86) PCT No.: PCT/FR2009/000442
§ 371 (c)(1),
(2), (4) Date: Jan. 11, 2011

(87) PCT Pub. No.: WO2009/130422
PCT Pub. Date: Oct. 29, 2009

(65) Prior Publication Data
US 2011/0275663 A1    Nov. 10, 2011

(30) Foreign Application Priority Data

Apr. 24, 2008 (FR) ..................... 08 02302

(51) Int. Cl.
| | |
|---|---|
| C07C 275/54 | (2006.01) |
| C07C 335/26 | (2006.01) |
| C07D 213/81 | (2006.01) |
| C07D 209/08 | (2006.01) |
| C07D 209/14 | (2006.01) |
| C07D 235/14 | (2006.01) |
| C07D 307/68 | (2006.01) |
| C07D 317/68 | (2006.01) |
| C07D 319/18 | (2006.01) |
| C07D 333/38 | (2006.01) |
| C07D 471/04 | (2006.01) |
| C07D 513/04 | (2006.01) |
| C07D 235/18 | (2006.01) |
| C07C 335/08 | (2006.01) |

(52) U.S. Cl.
CPC ............ *C07C 335/26* (2013.01); *C07D 235/18* (2013.01); *C07C 335/08* (2013.01); *C07C 275/54* (2013.01); *C07C 2101/14* (2013.01); *C07D 209/08* (2013.01); *C07D 209/14* (2013.01); *C07D 213/81* (2013.01); *C07D 235/14* (2013.01); *C07D 307/68* (2013.01); *C07D 317/68* (2013.01); *C07D 319/18* (2013.01); *C07D 333/38* (2013.01); *C07D 471/04* (2013.01); *C07D 513/04* (2013.01)

(58) Field of Classification Search
CPC . A61K 2300/00; A61K 31/00; A61K 31/167; C07D 213/81; C07D 235/18; D07D 513/04; C07C 335/08
See application file for complete search history.

(56) References Cited

U.S. PATENT DOCUMENTS

| | | | |
|---|---|---|---|
| 6,521,643 B1 | 2/2003 | Tomishima et al. | |
| 6,677,365 B2 * | 1/2004 | Laborde et al. | 514/379 |
| 2003/0187043 A1 | 10/2003 | Maurer et al. | |
| 2004/0087659 A1 * | 5/2004 | Defossa et al. | 514/586 |
| 2004/0152743 A1 | 8/2004 | Schoenafinger et al. | |
| 2005/0085519 A1 | 4/2005 | Rubin et al. | |

FOREIGN PATENT DOCUMENTS

| | | |
|---|---|---|
| EP | 1 695 966 A1 | 8/2006 |
| GB | 2 134 518 A | 8/1984 |

OTHER PUBLICATIONS

International Search Report and Written Opinion for PCT/FR2009/000442 dated Nov. 13, 2009.
Li, J. et al., *Discovering Novel Chemical Inhibitors of Human Cyclophilin A: Virtual Screening, Synthesis, and Bioassay*, Bioorganic & Medicinal Chemistry 14 (2006), pp. 2209-2224.
Montes, M. et al., *Receptor-Based Virtual Ligand Screening for the Identification of Novel CDC25 Phosphatase Inhibitors*, J. Chem. Inf. Model, 48, (2008), pp. 157-165.
Berman, David M., et al., "Medulloblastoma Growth Inhibition by Hedgehog Pathway Blockade," *Science*, 2002, vol. 297, pp. 1559-1561.
Berman, David M., et al., "Widespread requirement for Hedgehog ligand stimulation in growth of digestive tract tumours," *Nature*, 2003, vol. 425, pp. 846-851.
Karhadkar, Sunil S., et al., "Hedgehog signalling in prostate regeneration, neoplasia and metastasis," *Nature*, 2004, vol. 431, pp. 707-712.
Masdeu, Christelle, et al., "Identification and characterization of Hedgehog modulator properties after functional coupling of Smoothened to $G_{15}$," *Biochem. Biophys. Res. Comm.*, 2006, vol. 349, pp. 471-479.
Watkins, D. Nell, et al., "Hedgehog signalling within airway epithelial progenitors and in small-cell lung cancer," *Nature*, 2003, vol. 422, pp. 313-317.

* cited by examiner

*Primary Examiner* — Samira Jean-Louis
(74) *Attorney, Agent, or Firm* — Alston & Bird LLP

(57) ABSTRACT

The present invention relates to the use of acylthiourea or acylurea derivatives for the treatment of pathologies involving a tissue dysfunction associated with a deregulation of the Hedgehog protein signalling pathway, and also to novel acylthiourea or acylurea derivatives as such, to their use as a medicinal product, and to pharmaceutical compositions containing them.

19 Claims, 3 Drawing Sheets

N-ACYLTHIOUREA AND N-ACYLUREA INHIBITORS OF THE HEDGEHOG PROTEIN SIGNALLING PATHWAY

FIELD OF THE INVENTION

The present invention relates to the use of acyl-thiourea or acyl-urea derivatives for the treatment of pathologies involving a tissue dysfunction linked to deregulation of the Hedgehog protein signaling pathway, as well as to novel acyl-thiourea or acyl-urea derivatives per se, to their use as a drug, and to pharmaceutical compositions containing them.

BACKGROUND OF THE INVENTION

The Hedgehog (Hh) signaling molecule is a secreted autoproteolytic protein that activates the Hedgehog protein signaling pathway, a signaling pathway that plays a fundamental role in the morphogenesis of many tissues, in particular in the formation of the entoderm and the embryonal axis, the development of the brain and hair follicules, as well as in cell proliferation, and is probably involved in tissue maintenance and repair in the adult (For a review, see: Ingham et al., Genes Dev., 2001, 15, 3059-3087; Marti et al., Trends Neurosci., 2002, 25, 89-96; Weschler et al., Annu. Rev. Neurosci., 2001, 24, 385-428).

The Hedgehog protein and the associated transduction pathway, initially observed in *drosophila*, are conserved in vertebrates and invertebrates. A single homologue of Hh is present in *Drosophila*, while three homologues of Hh: Sonic (Shh), Indian (Ihh) and Desert (Dhh) are present in mammals. Of these three homologues, Shh has been the most widely studied because of its extended expression profile during development. Shh participates in ventralization of the neural tube by specifying the early phenotype of several types of neurons along the ventral median line (spinal cord motor neurons, dopaminergic or cholinergic neurons) and by inducing the generation of oligodendrocyte precursors from the ventral spinal cord. Further, Shh induces survival of gabaergic and dopaminergic neurons, orientates the development of serotoninergic precursors and prevents the death of dopaminergic neurons provoked by the toxin MPP. Finally, it induces proliferation of precursors of granular cells in the early post-natal cerebellum. The other members of the Hedgehog family participate respectively in the development of bone tissue (Ihh), the testicles and the peripheral nerves (Dhh). Furthermore, the results obtained with Shh are also applicable to Dhh and Ihh.

The regulatory role of the Hedgehog protein signaling pathway during embryo development has been widely studied: Hh has been associated with maintenance and repair processes in normal tissue and in the spatiotemporal regulation of proliferation and differentiation, thereby allowing developing tissues to reach their correct size with the appropriate cell types and appropriate degrees of vascularization and innervation. The essential role of the Hh signaling function is demonstrated by the dramatic consequences of defects in this signaling pathway in the human fetus, such as holoprosencephaly observed in Sonic Hedgehog mutants.

More recently, the Shh pathway has been identified in the adult brain where the active amino-terminal form of the molecule is expressed in many regions of the mature nervous system at a higher level than that encountered during the early post-natal period (Traiffort et al., Eur. J. Neurosci., 1999, 11, 3199-3214 and 2001, 14, 839-850). Although the roles of Shh in the adult have not been completely elucidated, it appears that, like other neurotrophic molecules, it is a factor that is capable of promoting survival and maintenance of the phenotype of cells of the nervous system (Reilly et al., Mol. Cell. Neurosci., 2002, 19, 88-96; Charytoniuk et al., Eur. J. Neurosci., 2002, 16, 2351-2357). Under pathological conditions, such as a model for Parkinson's disease or a model for peripheral neuropathy, Shh is capable of preserving the axonal projections of dopaminergic neurons in the striatum or of improving the time required for motor recovery consecutive upon crushing of the sciatic nerve (Tsuboi et al., Exp. Neurol., 2002, 173, 95-104; Pepinski et al., J. Pharm. Sci., 2002, 91, 371-387).

Hh proteins are synthesized in the form of immature precursors of approximately 45 kDa that undergo intramolecular cleavage catalyzed by the C-terminal region of the precursor. Said cleavage produces a 25 kDa C-terminal fragment with no known supplemental function and a 19 kDa amino-terminal fragment (denoted HhNp for N-terminal processed domain) bound at its C-terminal end to a molecule of cholesterol, sufficient for all of the known signaling activities of Hedgehog proteins.

The Hedgehog protein signaling pathway comprises three principal components: the Hh ligand, a transmembrane receptor circuit composed of the Patched (Ptc) negative regulator and the Smoothed (Smo) activator, and a cytoplasmic complex that regulates the transcriptional effectors.

The cellular response to the Hedgehog morphogen is controlled by the expression products of the Patched (Ptc) gene, a tumor suppressor gene, and the Smoothened (Smo) proto-oncogene; however, the exact mechanism for Hedgehog pathway regulation has not been completely elucidated. In mammals, there are two Patched genes coding respectively for Ptc1 and Ptc2, glycoproteins with 12 transmembrane domains, homologs of bacterial transporters. The product of the Smo gene that codes for a protein of the family of receptors coupled to G proteins, has no known endogenous ligand. In the absence of Hedgehog, Ptc will block the constitutive activity of Smo. Binding of Hedgehog to Ptc will lift this inhibition and allow signal transduction via Smo. The mechanism for regulating the activity of Smo by Ptc in mammals could involve a molecule transported by Ptc and interacting with Smo (Taipale et al., Nature, 2002, 418, 892-896). The activation of Gli transcription factors is involved in the cascade of events resulting from the activity of Smo. The type I transmembrane protein, HIP (Hedgehog Intercating Protein) constitutes another receptor for Hedgehog molecules which it binds with an affinity comparable to that of Ptc; HIP has been proposed as a negative pathway regulator (Ingham et al., cited above; Ho et al., Curr. Opin. Neurobiol., 2002, 12, 57-63; Taipale et al., Nature, 2001, 411, 349-354). Furthermore, the products of the dispatched (disp) gene, in particular DispA, may be involved in release and accumulation of Hedgehog proteins in the soluble form in the extracellular medium (Ma et al., Cell, 2002, 111, 63-75).

Dysfunctions of the Shh signaling pathway have been associated with a number of cancers, in particular following characterization of Ptc as a tumor suppressor gene. In fact, inactivating mutations of Ptc are associated with Gorlin Syndrome or basocellular naevomatosis, a dominant autosomal disease characterized by cranofacial and cerebral deformities, but primarily by a raised incidence of various tumors, more particularly basocellular carcinomas as regards the skin and medulloblastomas as regards the brain. Mice heterozygous for the Ptc gene develop tumors of the cerebellum, suggesting that a modification of the Shh pathway is at the origin of such tumors (Goodrich et al., Science, 1997, 277, 1109-1113).

Mutations of human Ptc or Smo genes are also observed in primitive neuroectodermal tumors of the central nervous system, principally medulloblastomas (30% of cases), but also in sporadic forms of basocellular carcinomas (40% and 20%, respectively for Ptc and Smo). Furthermore, mutations in Shh (H133Y) are also associated with basocellular carcinomas. Smo mutations, which principally concern two amino acids located in the seventh hydrophobic domain of the receptor (W535L and S533N), induce constitutive activation of the pathway which escapes the negative control of Ptc. In contrast, mutations of Ptc result in a reduction in the inhibition exerted thereby on Smo in the absence of Shh. In both cases, activation of the Shh pathway is the result, leading to a powerful mitogenic activity demonstrated in cultures of precursors of granular cells of the developing brain and to a blockage of the terminal step of differentiation of those neuroblasts (Traiffort et al., Eur. J; Neurosci., 1999, cited above; Charytoniuk et al., J. Physiol. Paris, 2002, 96, 9-16; Dahmane et al., Development, 1999, 126, 3089-3100; Wallace et al., Curr. Biol., 1999, 22, 103-114; Weshler-Reya et al., Neuron., 1999, 22, 103-114). Similarly, the expression of Smo carrying one of these mutations in transgenic mice results in the presence of basocellular carcinomas, demonstrating the direct implication of Smo in the development of these tumors (Xie et al., Nature, 1998, 391, 90-92).

Apart from basocellular carcinomas and medulloblastomas, other types of tumor have been associated with a defect in the Hedgehog signaling pathway; the localization of these tumors is closely correlated with the expression sites of the components of the pathway during embryonic development. Non-limiting examples that may be cited are: breast and meningiomal cancers associated with Ptc mutations, glioblastomas associated with Gli mutations, gastro-intestinal cancers, in particular primary cancers of the stomach, prostate cancers, fibromas and ovarian dermoids, rhabdomyosarcomas, small cell lung cancers, and oral squamous cell carcinomas. Recently, Shh has been associated with psoriasis.

Because of the crucial role played by the Hedgehog protein signaling pathway in many physiological processes and as a consequence of the significance of diseases linked to its dysfunction, the components of this pathway such as the Smoothened, Patched (Patched 1 and Patched 2) proteins, the Dispatched (Dispatched 1 and Dispatched 2) proteins or the HIP protein, represent targets for developing novel molecules that are capable of modulating (activating or inhibiting) this pathway and thus of positively or negatively regulating the development [proliferation, differentiation, migration, survival (apoptosis)] and/or the activity of differentiated and stem cells, in vitro and/or in vivo in the embryo or in the adult.

Such molecules can be used in the treatment of tumors associated with hyperactivation of the Hedgehog pathway: nerve tissue tumors (medulloblastomas, primitive neuroectodermal tumors, glioblastomas, meningiomas and oligodendrogliomas), cutaneous tumors (basocellular carcinomas, trichoepitheliomas), bone and muscle tissue tumors (rhabdomyosarcomas, osteosarcomas) and tumors of other tissues (kidney, bladder).

Such molecules can also be used in the treatment of neurodegenerative type diseases necessitating blockage of the Hedgehog pathway (Parkinson's disease, Huntington's chorea, Alzheimer's disease, multiple sclerosis, motor neuron disease), and diseases in which a blockage of the Hedgehog signaling pathway could be beneficial, such as diabetes.

Such molecules are also useful in the medical or surgical treatment (plastic or reparative surgery, tissue or organ transplants) of numerous acute, sub-acute or chronic, genetic or acquired pathologies—involving a tissue dysfunction linked to deregulation of the Hedgehog pathway—to induce the formation, regeneration, repair and/or to increase the activity of tissues; non-limiting examples are: nerve tissue [central nervous system (brain) and peripheral nervous system (sensory, motor, sympathetic neurons)], bone, cartilage, testicles, liver, spleen, intestine, pancreas, kidneys, smooth and skeletal muscles, the heart, lungs, skin and hair system, the mucous membranes, blood cells and cells of the immune system. Non-limiting examples of such pathologies that may in particular be cited are neuropathies and associated neuromuscular diseases, diabetes, alopecia, burns, ulcers (skin and mucous membranes) and problems with spermatogenesis.

Various molecules that are capable of modulating the activity of the Hedgehog pathway have been identified:

Hedgehog proteins and derivative polypeptides (fragments, variants . . . ), in particular Hedgehog proteins antagonists (International application PCT WO 01/98344 in the name of BIOGEN); because of their size, such proteins and polypeptide derivatives cannot pass through the hematoencephalic barrier and thus cannot be administered systemically, in particular for the treatment of cerebral tumors linked to hyperactivation of the Hedgehog protein signaling pathway. Furthermore, such molecules are difficult to produce and to purify and have poor stability;

heterocyclic organic molecules (International application PCT WO 01/74344 in the name of CURIS and Chen et al., PNAS, 2002, 99, 14071-14076);

nitrogen-containing heterocyclic molecules (International applications PCT WO 01/19800, WO 01/26644 and WO 02/30421 in the name of CURIS and Kamenetsky et al., J. Biol., 2002, 1, 1-19); and plant steroids derived from *Veratrum* spp (jervine, cyclopamine and cycloposine) and from *Solanum* spp. (solanidine), substituted in position 16, 17 or 18 with an amine or an amine derivative, and cholesterol: American patent U.S. Pat. No. 6,432,970 and International applications PCT WO 99/52534 and WO 01/27135 in the name of JOHNS HOPKINS UNIVERSITY SCHOOL OF MEDICINE; American patent U.S. Pat. No. 6, 291, 516 in the name of CURIS; International application PCT WO 00/41545 in the name of ONTOGENY; International application PCT WO 02/30462 in the name of CURIS; Talpale et al., Nature, 2000, 406, 1005-1009; Berman et al., Science, 2002, 297, 1559-1561. However, cyclopamine is a teratogenic agent at the origin of holoprosencephaly and cyclopia in the embryo in mammals and the absence of toxicity to mammals of other compounds derived from plant steroids has not yet been demonstrated;

mifepristone (17β-hydroxy 11β-(4-dimethylamino phenyl) 17α-(prop-1-ynyl)estra-4,9-dien-3-one), also denoted RU-486 or RU-38486 (French patent FR 03 00646 in the name of CNRS), for which an inhibiting activity of the activity of the Hedgehog protein signaling pathway has been demonstrated.

It appears from the foregoing that there is currently no effective molecule for the treatment of pathologies necessitating an inhibition of the activity of the Hedgehog protein signaling pathway for which an absence of toxicity has been established by clinical trials in man.

As a consequence, the inventors set themselves the target of providing novel compounds that are inhibitors of the Hedgehog protein signaling pathway that are more practical, and are in particular simple to synthesize and potentially useful in human therapy.

SUMMARY OF THE INVENTION

This aim is achieved by providing the compounds with formula (I) that are described below to the extent that these molecules have the advantage of comprising functions of the acyl-thiourea or acyl-urea type which are obtained from readily available substances. Furthermore, the thioureas are transformed into ureas by a simple oxidation step; thus, it is easy to obtain the series of compounds with formula (I).

In consequence, the present invention concerns the use, in the manufacture of a drug for the treatment of tumors associated with a hyperactivation of the Hedgehog protein signaling pathway or of pathologies of the neuro-degenerative type, of compounds with the following formula (I):

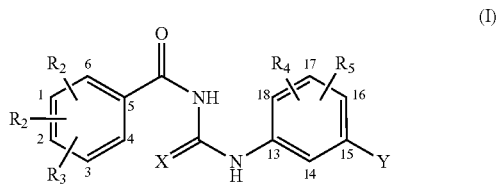

wherein:

$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, a substituted alkoxy group, or a fused heterocycle obtained from two adjacent radicals $R_1$, $R_2$ and $R_3$, which can form a fused heterocycle together with the carbon atoms of the phenyl cycle to which they are bonded;

X represents a sulfur or oxygen atom;

Y represents a mono- or polycyclic heteroaryl group, which is substituted or non-substituted, a —NH—(C=O)—$R_6$, —(C=O)—NH—$R_6$ or —NH—(C=O)—NH—$R_6$ group wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;

$R_4$ and $R_5$, which are identical or different and independent of each other, represent a hydrogen or a halogen atom, or an alkoxy, alkylthio, alkyl, perfluoroalkyl, nitrile or nitro group.

Preferably:

$R_4$ and/or $R_5$ represent a nitro group;

two adjacent groups $R_1$, $R_2$ and $R_3$ form a fused heterocycle jointly with the carbon atoms of the phenyl cycle to which they are bonded, such as, for example, a benzodioxole, an oxindole, a benzoxazolone or a quinoline;

when Y represents a —NH—(C=O)—$R_6$ group.

Advantageously, when Y represents a substituted or non-substituted heterocycle, said heterocycle is a polycyclic heterocycle. Still more preferably, said polycyclic heterocycle is selected from indole, benzoimidazole, imidazopyridine and imidazothiazole groups.

DETAILED DESCRIPTION OF THE INVENTION

Figure 1:
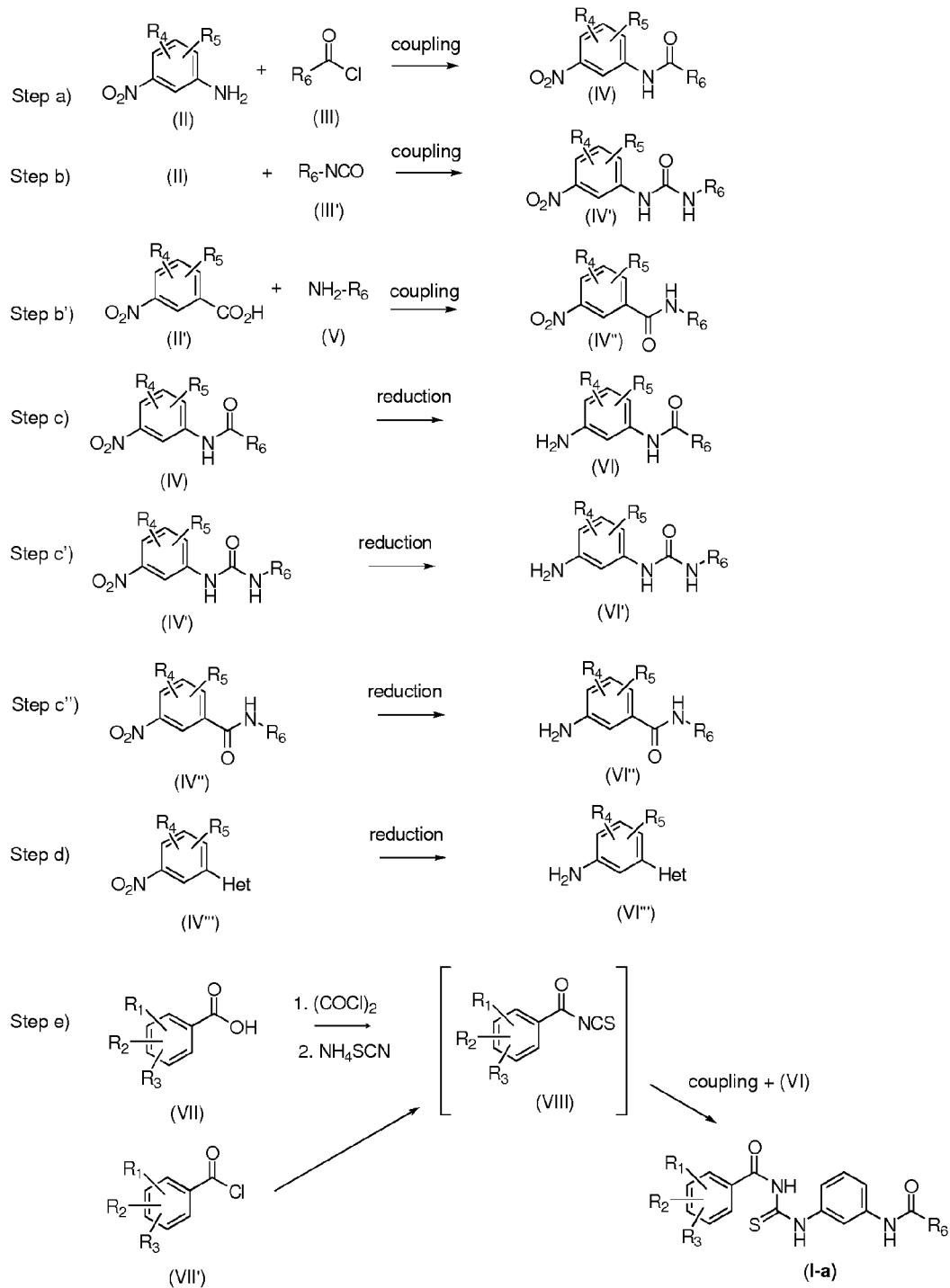
FIG. 1 shows a general synthesis scheme for compounds within formula (I)
Figure 1:
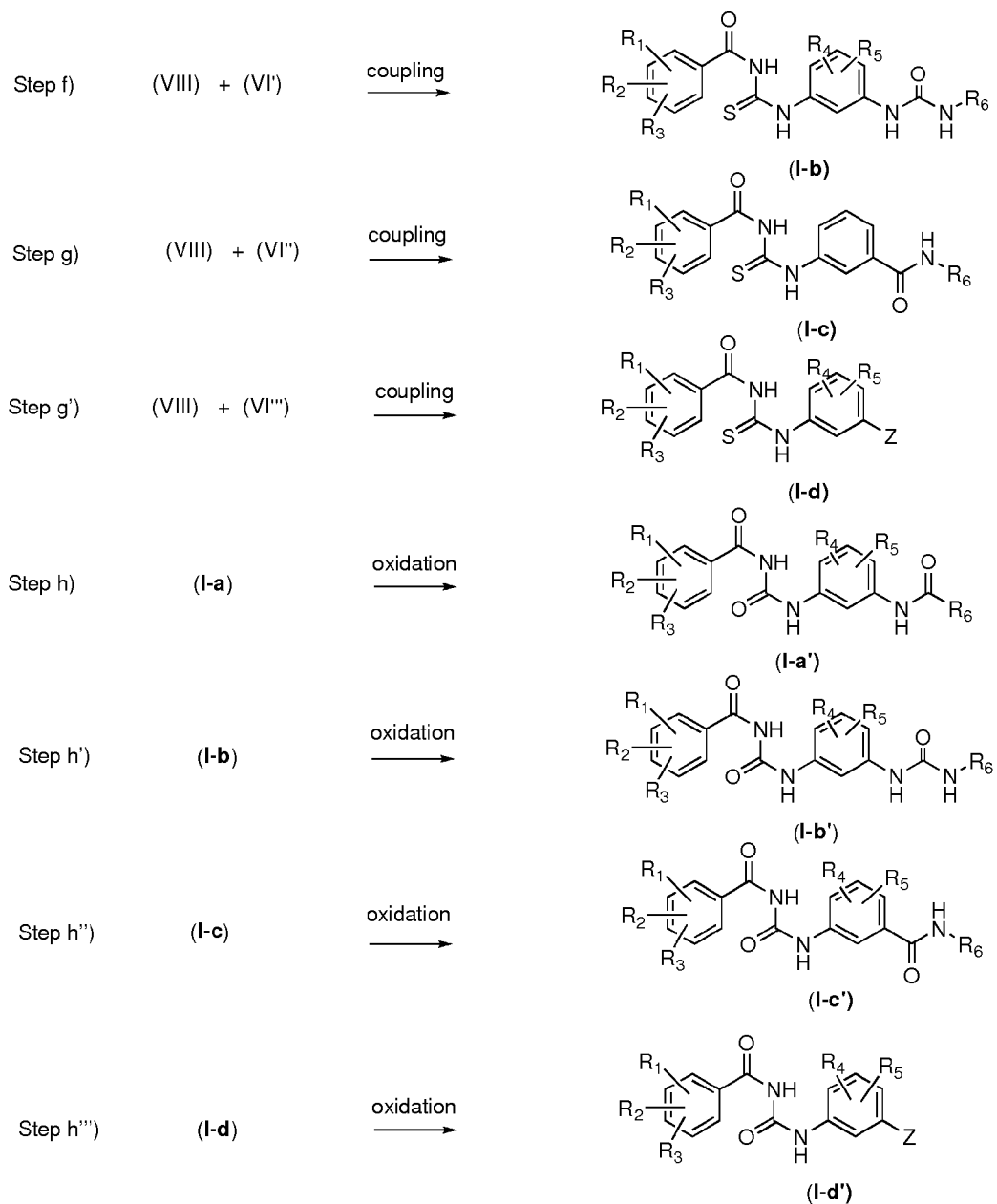

As will be demonstrated in the examples that illustrate the present invention, the compounds with formula (I) as claimed in the invention have an activity in inhibiting the Hedgehog protein signaling pathway and are thus useful in the treatment of tumors associated with a hyperactivation of the Hedgehog protein signaling pathway or of pathologies of the neurodegenerative type.

The compounds with formula (I) as claimed in the present invention can be divided into sub-units A, B, C, (or C' or C") and D (or D' or D") and represented by the following formulas (I-a), (I-a'), (I-b), (I-b'), (I-c), (I-c'), (I-d) and (I-d'):

wherein radicals $R_1$ to $R_6$ have the meanings given hereinabove, and the group Z represents a substituted or non-substituted mono- or polycyclic heteroaryl group.

In these formulas, the sub-unit A corresponds to an acyl-aryl portion, the sub-unit B corresponds to a thiourea (X=S) or urea (X=O) portion, the sub-unit C corresponds to a 1,3-diaminoaryl group, the sub-unit C' corresponds to a 1,3-aminobenzoyl group, the sub-unit C" corresponds to an aminophenyl group, the sub-unit D corresponds to an alkyloyl, aroyl or heteroaroyl residue, the sub-unit D' corresponds to an alkylamino, arylamino or heteroarylamino residue, and the sub-unit D" corresponds to a substituted or non-substituted mono- or polycyclic heteroaryl residue, directly attached to the radical C".

The following terms have the following meanings in the context of the present invention:

alkyl: a linear or branched saturated aliphatic hydrocarbon group containing 1 to 5 carbon atoms, preferably 1 or 2 carbon atoms. The term "branched" means that at least one lower alkyl group such as methyl or ethyl is carried by a linear alkyl chain. The term "lower" alkyl means an alkyl containing 1 or 2 carbon atoms; the term "higher alkyl" means a linear or branched alkyl group containing 3 to 5 carbon atoms. Examples of alkyl groups that may be mentioned are methyl, ethyl, n-propyl, i-propyl, n-butyl, t-butyl and n-pentyl;

halogen atom: denotes bromine, chlorine, iodine or fluorine, the designations bromine, chlorine and fluorine being preferred;

perfluoroalkyl: denotes an alkyl group as hereinbefore defined wherein all of the hydrogen atoms have been replaced with fluorine atoms. Preferred perfluoroalkyl groups are trifluoromethyl and perfluoroethyl;

alkoxy: denotes an O-alkyl group wherein the alkyl group may have the meaning indicated hereinabove. Examples of alkoxy groups that may in particular be cited are methoxy, ethoxy, n-propoxy, iso-propoxy, n-butoxy and pentoxy groups;

alkylthio: denotes an S-alkyl group wherein the alkyl group may have the meaning indicated hereinabove. Examples of alkylthio groups that may in particular be cited are methylthio, ethylthio, iso-propylthio, butylthio and pentylthio groups;

aryl group: denotes any functional group or substituent derived from at least one aromatic ring; an aromatic ring corresponds to any planar mono- or polycyclic group comprising a delocalized π system in which each atom of the ring has a p orbital, said p orbitals overlapping each other; examples of such aryl groups that may be mentioned are phenyl, benzylcyclobutene, pentalene, naphthalene, benzylphenyl and anthracene groups;

heteroaryl group: denotes any functional group or substituent derived from at least one aromatic ring as hereinbefore defined and containing at least one heteroatom selected from P, S, O and N; examples of heteroaryl groups that may be mentioned are furan, pyridine, pyrrole, thiophene, imidazole, pyrazole, oxazole, isoxazole, thiazole, pyridine, imidazopyridine, imidazothiazole, pyrazine, pyrimidine, pyridazine, benzofuran, isobenzofuran, indole, isoindole, benzothiophene, benzo[c]thiophene, benzimidazole, indazole, benzoxazole, benzisoxazole, benzothiazole, quinoline, isoquinoline, quinoxaline, quinazoline, cinnoline, purine and acridine groups;

saturated or unsaturated mono- or polycyclic hydrocarbon group: denotes any functional group or substituent derived from a non-aromatic cycle comprising at least 3 carbon atoms which may optionally comprise one or more heteroatoms selected from P, S, O and N. Particular examples of such groups that may be cited include cyclopropyl, cyclobutyl, cyclopentyl and cyclohexyl; the cyclohexyl group is preferred.

In a preferred embodiment of the invention, the compounds with formula (I) are selected from those wherein:

$R_1$, $R_2$, and $R_3$, which are identical or different, represent a hydrogen atom or a methyloxy or ethyloxy radical;

X represents a sulfur or oxygen atom;

$R_4$ and $R_5$, which are identical or different, are selected from hydrogen, chlorine, bromine, fluorine, methyl and methoxy; and Y represents a mono- or polycyclic heteroaryl group, which is substituted or non-substituted, a —NH—(C=O)—$R_6$, —(C=O)—NH—$R_6$ or —NH—(C=O)—NH—$R_6$ group wherein $R_6$ represents a group selected from phenyl groups; phenyl substituted with a methoxy or dimethylamino radical, with a chlorine atom, with a phenyl group, or with a benzyl group; or a cyclohexyl, isopropyl, pyridinyl, naphthyl, furfuryl and thiophene group.

Non-limiting examples of compounds with formula (I) that may be cited are:

N-[[[3-(4-methoxy-benzoylamino)phenyl]amino]thioxomethyl]-3,4,5-methoxy-benzamide (I-a) with the following formula:

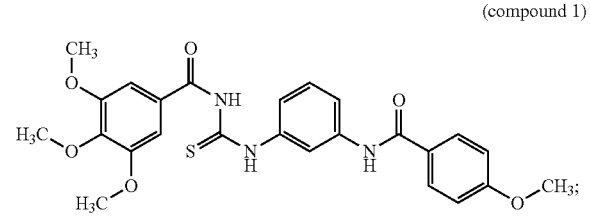 [SMILES: COc1ccc(C(=O)Nc2cccc(NC(=S)NC(=O)c3cc(OC)c(OC)c(OC)c3)c2)cc1]

(compound 1)

N-[[[3-(2-chloro-benzoylamino)phenyl]amino]thioxomethyl]-3,4,5-methoxy-benzamide (I-a) with the following formula:

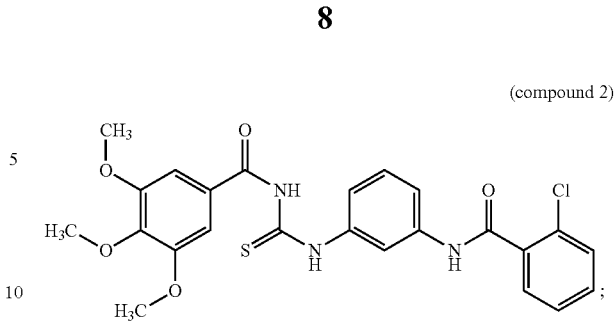

(compound 2)

N-[[[3-(3-methoxy-benzoylamino)phenyl]amino]thioxomethyl]-3,4,5-methoxy-benzamide (I-a) with the following formula:

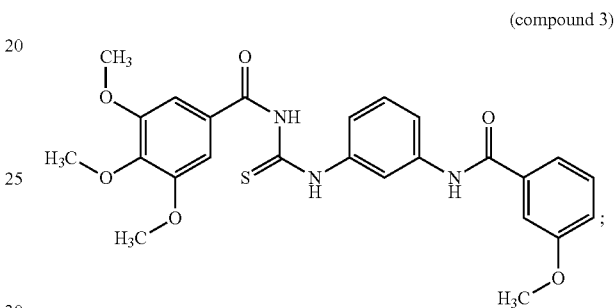

(compound 3)

N-[[[3-(2-methoxy-benzoylamino)phenyl]amino]thioxomethyl]-3,4,5-methoxy-benzamide (I-a) with the following formula:

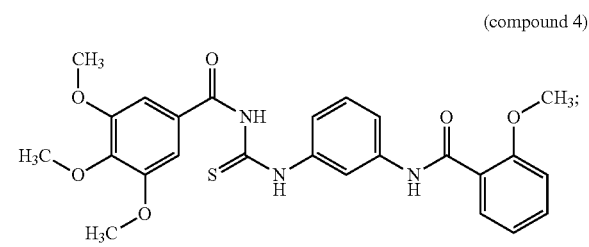 [SMILES: COc1ccccc1C(=O)Nc1cccc(NC(=S)NC(=O)c2cc(OC)c(OC)c(OC)c2)c1]

(compound 4)

N-[[[3-(4-phenyl-benzoylamino)phenyl]amino]thioxomethyl]-3,4,5-methoxy-benzamide (I-a) with the following formula:

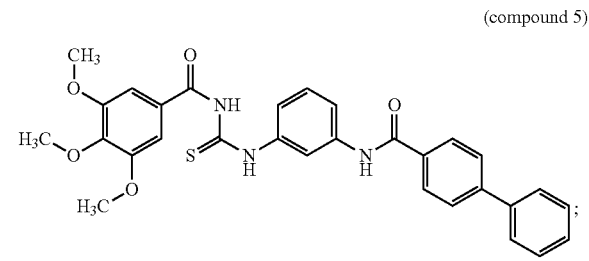 [SMILES: COc1cc(C(=O)NC(=S)Nc2cccc(NC(=O)c3ccc(-c4ccccc4)cc3)c2)cc(OC)c1OC]

(compound 5)

N-[[[3-(4-methoxy-benzoylamino)phenyl]amino]oxomethyl]-3,4,5-methoxy-benzamide (I-a') with the following formula:

(compound 6)

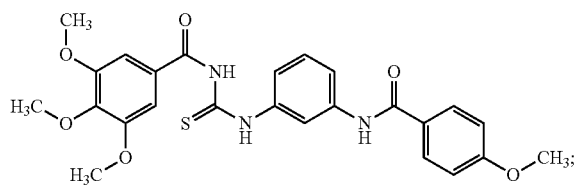

N-[[[3-(4-phenyl-benzoylamino)phenyl]amino]oxomethyl]-3,4,5-methoxy-benzamide (I-a') with the following formula:

(compound 7)

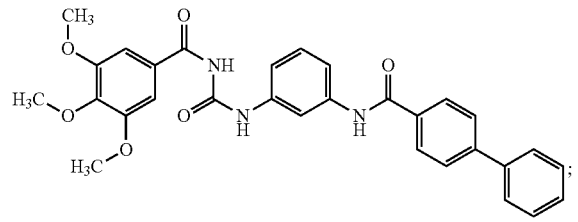

N-[[[3-(-cyclohexylcarboxylamino)phenyl]amino]thioxomethyl]-3,4,5-methoxy-benzamide (I-a) with the following formula:

(compound 8)

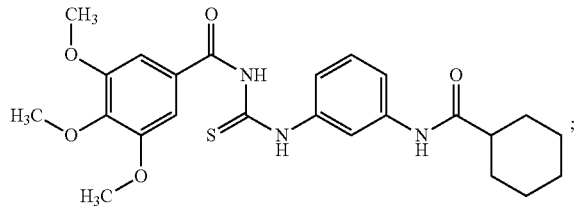

N-[[[3-(2-naphthoylamino)phenyl]amino]thioxomethyl]-3,4,5-methoxy-benzamide (I-a) with the following formula:

(compound 9)

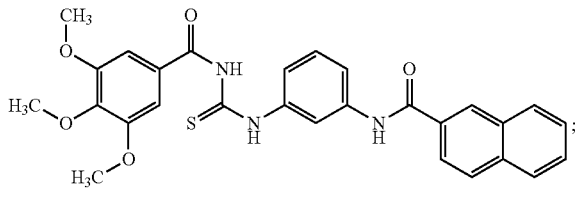

N-[[[3-(isopropoylcarboxylamino)phenyl]amino]thioxomethyl]-3,4,5-methoxy-benzamide (I-a) with the following formula:

(compound 10)

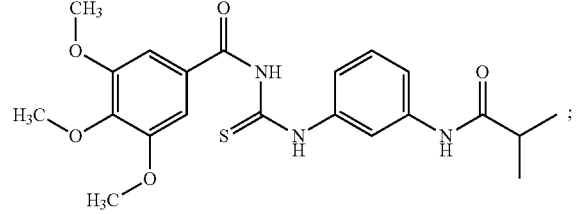

N-[[[3-(4-pyridocarboxylamino)phenyl]amino]thioxomethyl]-3,4,5-methoxy-benzamide (I-a) with the following formula:

(compound 11)

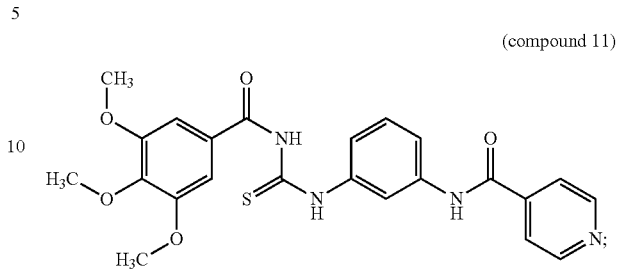

N-[[[3-(1-naphthoylamino)phenyl]amino]thioxomethyl]-3,4,5-methoxy-benzamide (I-a) with the following formula:

(compound 12)

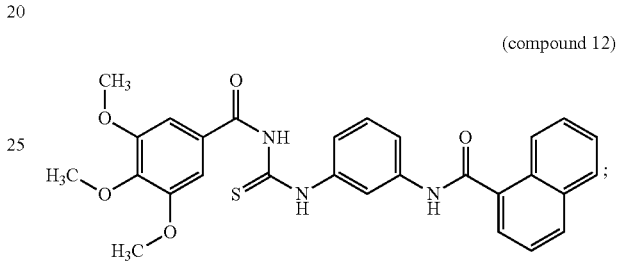

N-[[[3-(4-chloro-benzoylamino)phenyl]amino]thioxomethyl]-3,4,5-methoxy-benzamide (I-a) with the following formula:

(compound 13)

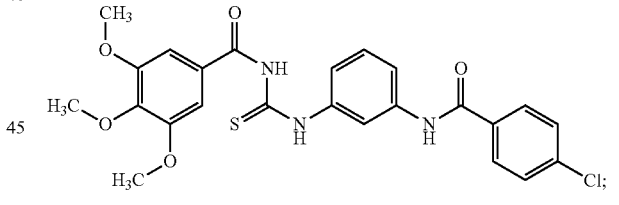

N-[[[3-(2-furoylamino)phenyl]amino]thioxomethyl]-3,4,5-methoxy-benzamide (I-a) with the following formula:

(compound 14)

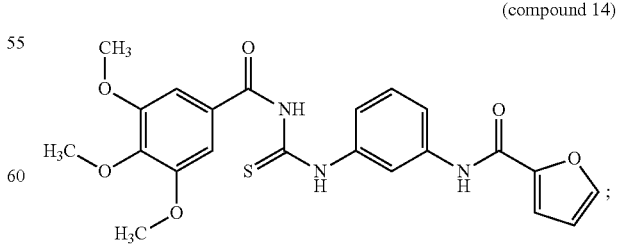

N-[[[3-(2-thiophenoylamino)phenyl]amino]thioxomethyl]-3,4,5-methoxy-benzamide (I-a) with the following formula:

(compound 15)

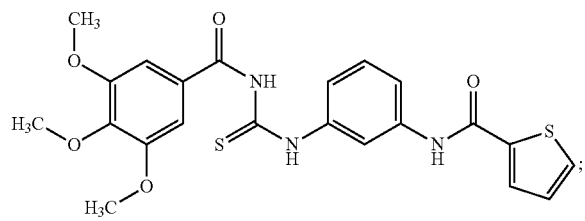

N-[[[3-(2-naphthoylamino)phenyl]amino]oxomethyl]-3,4,5-methoxy-benzamide (I-a') with the following formula:

(compound 16)

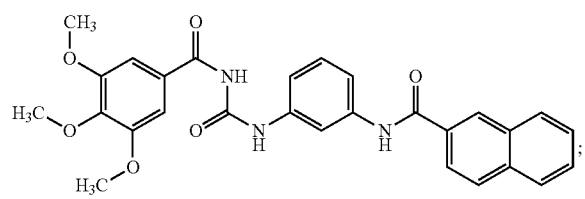

N-[[[3-(isopropoylcarboxylamino))phenyl]amino]oxomethyl]-3,4,5-methoxy-benzamide (I-a') with the following formula:

(compound 17)

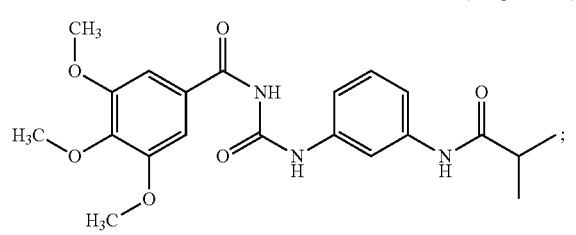

N-[[[3-(benzoylamino)phenyl]amino]thioxomethyl]-3,5-methoxy-benzamide (I-a) with the following formula:

(compound 18)

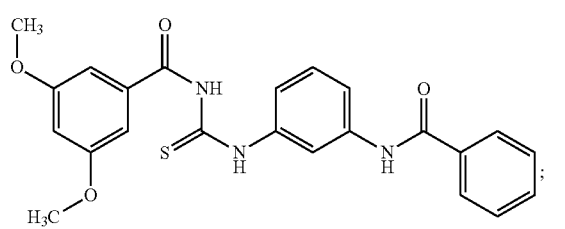

N-[[[3-(benzoylamino)phenyl]amino]thioxomethyl]-3,5-methoxy-4-ethoxy-benzamide (I-a) with the following formula:

(compound 19)

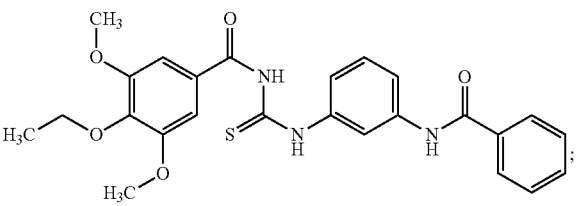

N-[[[3-(benzoylamino)phenyl]amino]thioxomethyl]-3,4-ethoxy-5-methoxy-benzamide (I-a) with the following formula:

(compound 20)

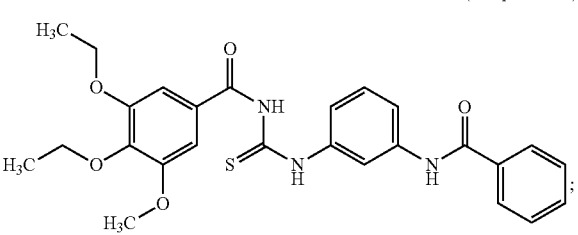

N-[[[3-(benzoylamino)phenyl]amino]thioxomethyl]-3,4-methylenedioxy-5-methoxy-benzamide (I-a) with the following formula:

(compound 21)

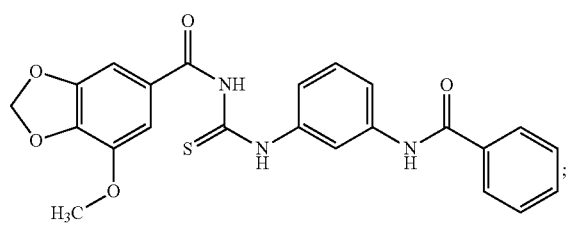

N-[[[3-(benzoylamino)phenyl]amino]thioxomethyl]-2,4-methoxy-benzamide (I-a) with the following formula:

(compound 22)

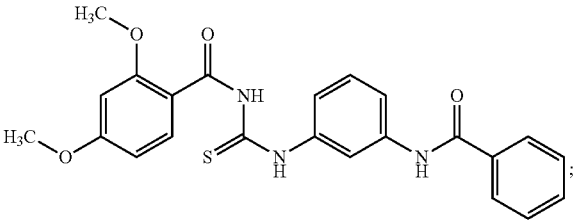

N-[[[3-(benzoylamino)phenyl]amino]thioxomethyl]-3,4,5-ethoxy-benzamide (I-a) with the following formula:

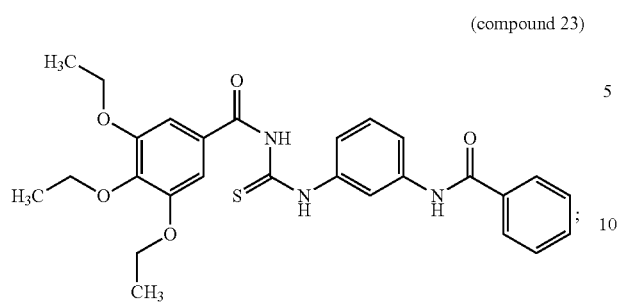

(compound 23)

N-[[[4-fluoro-3-(benzoylamino)phenyl]amino]thioxomethyl]-3,4,5-methoxy-benzamide (I-a) with the following formula:

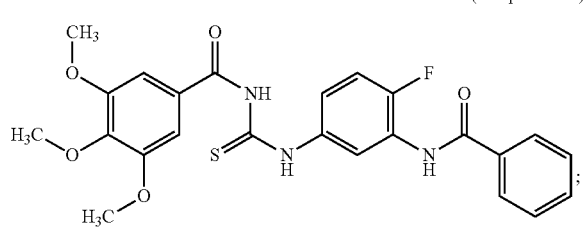

(compound 24)

N-[[[4-chloro-3-(phenylamino)carbonyl]amino]thioxomethyl]-3,4,5-methoxy-benzamide (I-b) with the following formula:

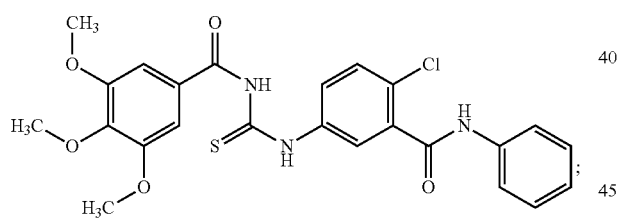

(compound 25)

N-[[[4-methoxy-3-(benzoylamino)phenyl]amino]thioxomethyl]-3,4,5-methoxy-benzamide (I-a) with the following formula:

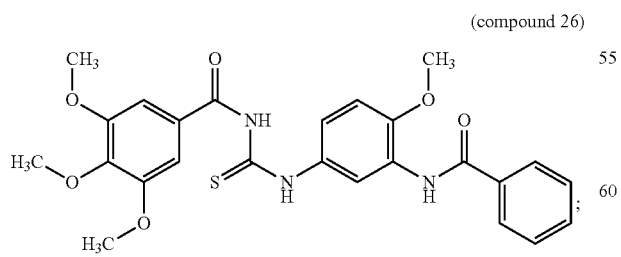

(compound 26)

N-[[[4-methyl-3-(benzoylamino)phenyl]amino]thioxomethyl]-3,4,5-methoxy-benzamide (I-a) with the following formula:

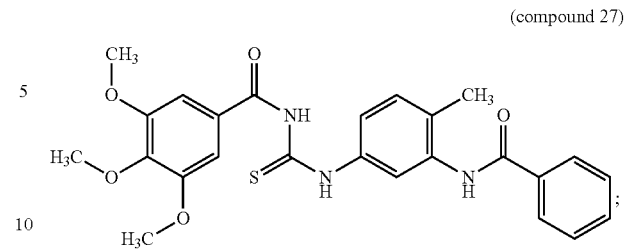

(compound 27)

N-[[[3-(benzoylamino)phenyl]amino]thioxomethyl]-3,4-ethylenedioxo-benzamide (I-a) with the following formula:

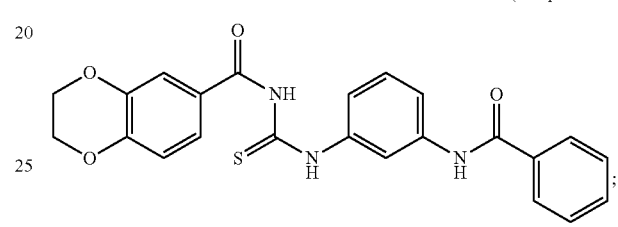

(compound 28)

N-[[[3-(benzoylamino)phenyl]amino]oxomethyl]-3,4,5-ethoxy-benzamide (I-a') with the following formula:

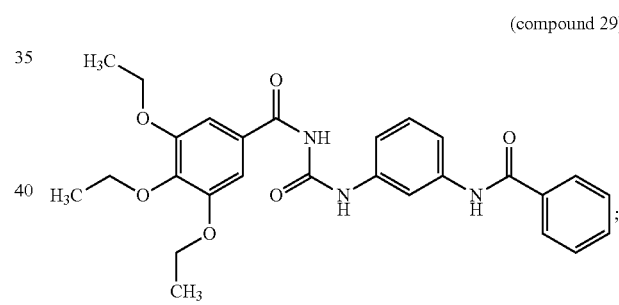

(compound 29)

N-[[[3-(benzoylamino)phenyl]amino]oxomethyl]-3,4-methylenedioxy-5-methoxy-benzamide (I-a') with the following formula:

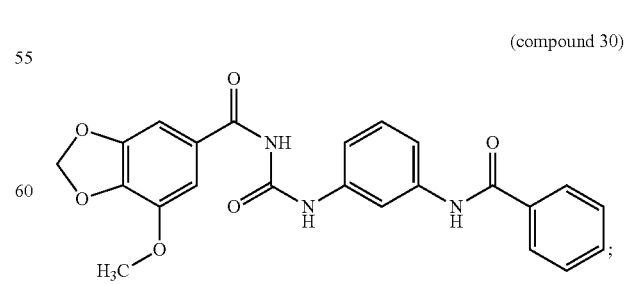

(compound 30)

N-[[[3-(Benzoylamino)phenyl]amino]oxomethyl]-3,4,5-methoxy-benzamide (I-a') with the following formula:

(compound 31)

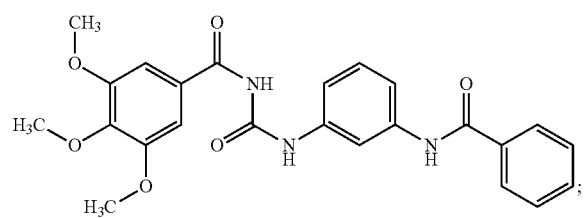

N-[[[3-methyl-3-(benzoylamino)phenyl]amino]thioxomethyl]-3,4,5-methoxy-benzamide (I-a) with the following formula:

(compound 32)

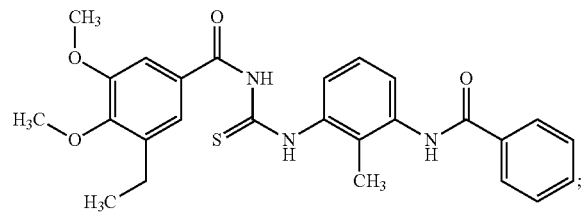

N-[[[4-chloro-3-(benzoylamino)phenyl]amino]oxomethyl]-3,4,5-methoxy-benzamide (I-a') with the following formula:

(compound 33)

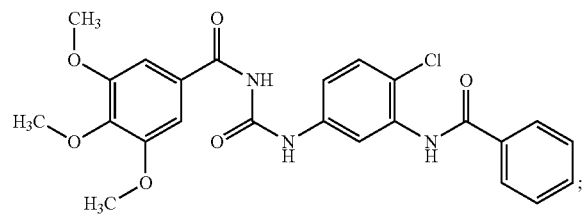

N-[[[4-chloro-3-(benzoylamino)phenyl]amino]thioxomethyl]-3,4,5-methoxy-benzamide (I-a) with the following formula:

(compound 34)

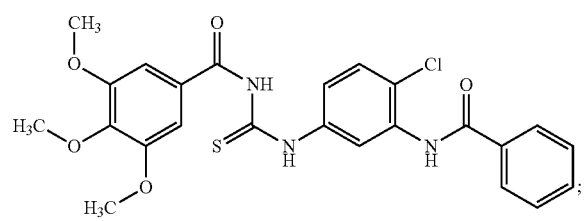

N-[[[5-chloro-3-(benzoylamino)phenyl]amino]thioxomethyl]-3,4,5-methoxy-benzamide (I-a) with the following formula:

(compound 35)

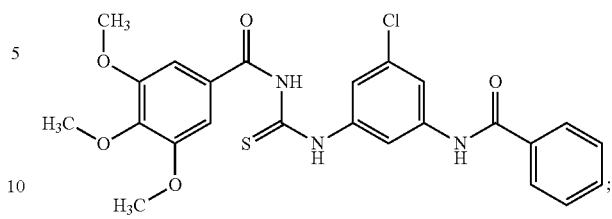

N-[[[5-fluoro-3-(benzoylamino)phenyl]amino]thioxomethyl]-3,4,5-methoxy-benzamide (I-a) with the following formula:

(compound 36)

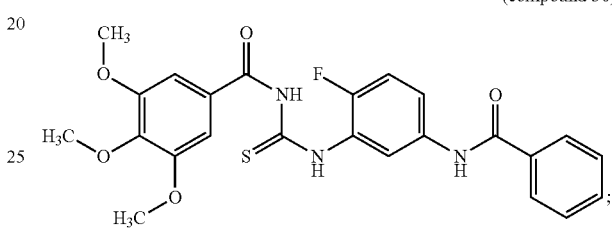

N-[[[4-chloro-3-(4-Phenyl-benzoylamino)phenyl]amino]oxomethyl]-3,4,5-methoxy-benzamide (I-a') with the following formula:

(compound 37)

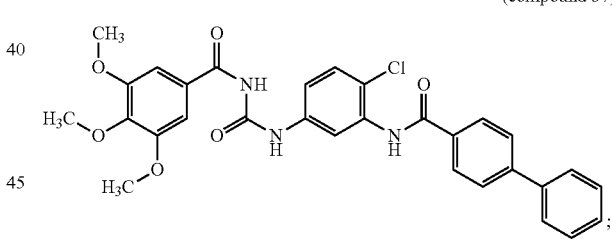

N-[[[3-(benzoylamino)phenyl]amino]thioxomethyl]-3,4,5-methoxy-benzamide (I-a) with the following formula:

(compound 38)

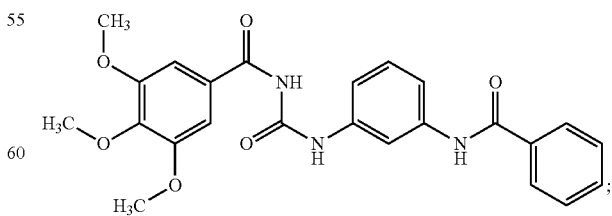

N-[[[4-chloro-3-(4-dimethylamino-phenylamino)carbonyl]thioxomethyl]-3,4,5-methoxy-benzamide (I-b) with the following formula:

(compound 39)

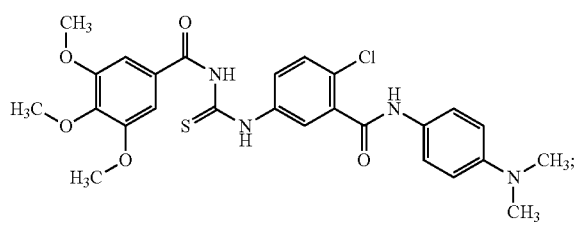

N-[[[4-chloro-3-(4-methoxy-phenylamino)carbonyl]thioxomethyl]-3,4,5-methoxy-benzamide (I-b) with the following formula:

(compound 40)

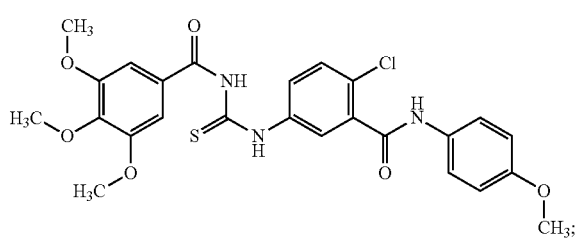

N-[[[5-bromo-3-(phenylamino)carbonyl]thioxomethyl]-3,4,5-methoxy-benzamide (I-b) with the following formula:

(compound 41)

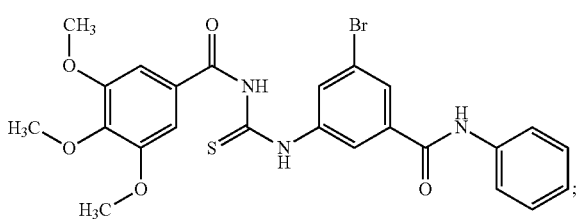

N-[[[4-chloro-3-(4-methoxy-phenylamino)carbonyl]oxomethyl]-3,4,5-methoxy-benzamide (I-b') with the following formula:

(compound 42)

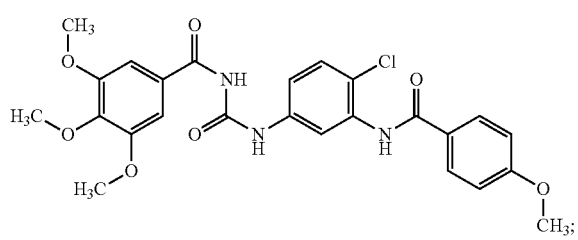

N-[[[4-chloro-3-(4-chloro-phenylamino)]carbonyl]phenylamino]thioxomethyl]-3,4,5-methoxy-benzamide (I-b) with the following formula:

(compound 43)

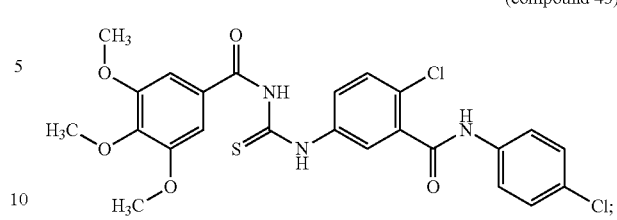

N-[[[4-chloro-3-(phenylamino)carbonyl]oxomethyl]-3,4,5-methoxy-benzamide (I-b') with the following formula:

(compound 44)

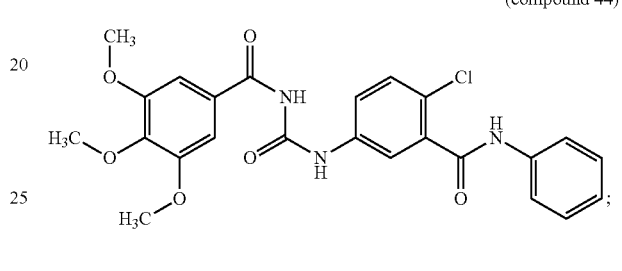

N-[[[2-methyl-3-(benzoylamino)phenyl]amino]oxomethyl]-3,4,5-methoxy-benzamide (I-a') with the following formula:

(compound 45)

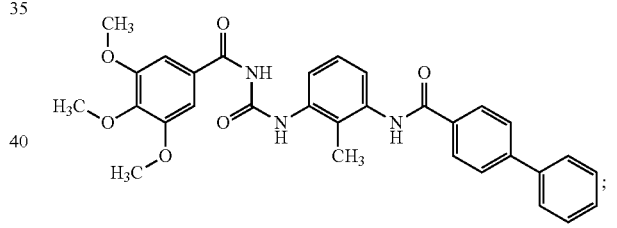

N-[[[2-methyl-3-(benzoylamino)phenyl]amino]thioxomethyl]-3,4,5-methoxy-benzamide (I-a) with the following formula:

(compound 46)

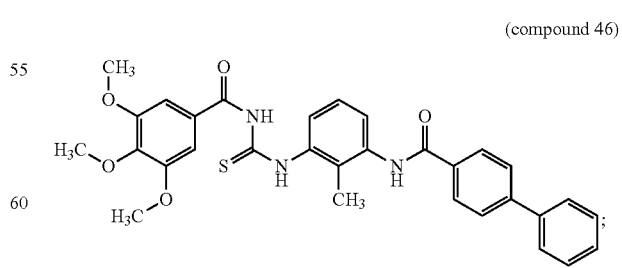

N-[[[-3-(4-chloro-benzoylamino)phenyl]amino]oxomethyl]-3,4,5-methoxy-benzamide (I-a') with the following formula:

(compound 47)

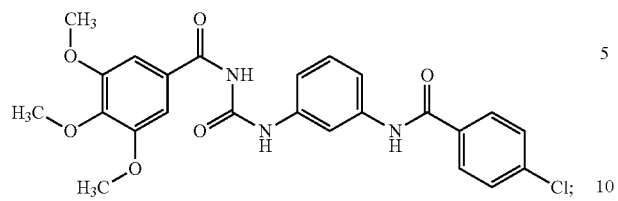

N-[[[-3-(benzoylamino)phenyl]amino]oxomethyl]-2,4,5-methoxy-benzamide (I-a') with the following formula:

(compound 48)

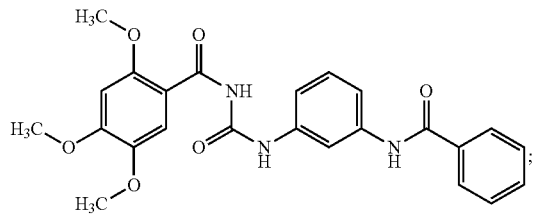

N-[[[-3-(benzoylamino)phenyl]amino]oxomethyl]-4-methoxy-benzamide (I-a') with the following formula:

(compound 49)

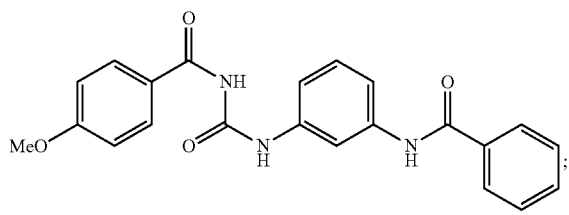

N-[[[-3-(benzoylamino)phenyl]amino]oxomethyl]-benzamide (I-a') with the following formula:

(compound 50)

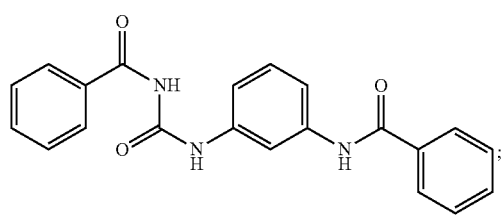

3,4,5-trimethoxy-N-(3-(3-phenylureido)phenylcarbamothioyl)benzamide (I-b) with the following formula:

(compound 51)

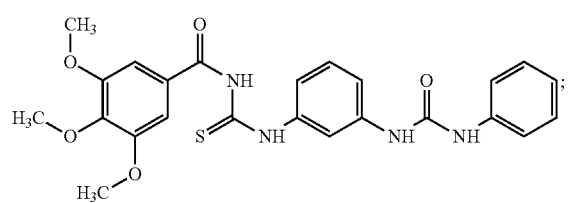

N-(3-(3-biphenyl-4-ylureido)phenylcarbamothioyl)-3,4,5-trimethoxybenzamide (I-b) with formula:

(compound 52)

N-(3-(1H-indol-2-yl)phenylcarbamoyl)-3,4,5-trimethoxybenzamide (I-d') with formula:

(compound 53)

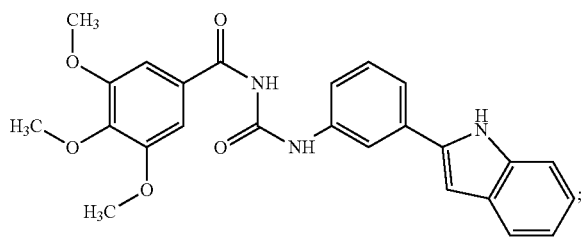

N-(3-(1H-indol-2-yl)phenylcarbamothioyl)-3,4,5-trimethoxybenzamide (I-d) with formula:

(compound 54)

N-(3-(imidazo[1,2-a]pyridin-2-yl)phenylcarbamothioyl)-3,4,5-trimethoxybenzamide (I-d) with formula:

(compound 55)

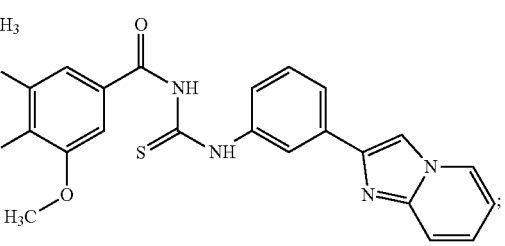

N-(3-(1H-benzo[d]imidazol-2-yl)-4-methylphenylcarbamothioyl)-3,4,5-trimethoxybenzamide (I-d) with formula:

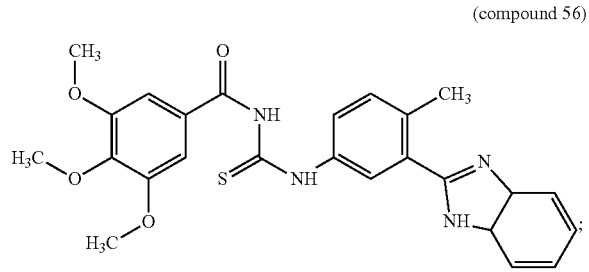 [SMILES: COc1cc(C(=O)NC(=S)Nc2ccc(C)c(C3=NC4C=CC=CC4N3)c2)cc(OC)c1OC]

N-(3-(1H-indol-1-yl)phenylcarbamothioyl)-3,4,5-trimethoxybenzamide (I-d) with formula:

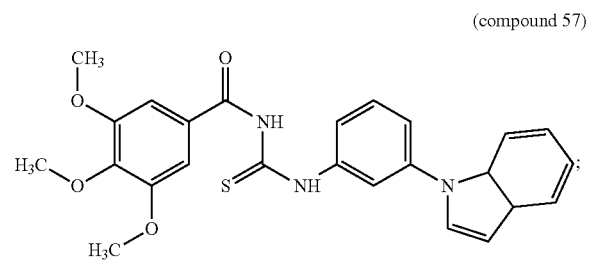 [SMILES: COc1cc(C(=O)NC(=S)Nc2cccc(N3C=CC4C=CC=CC43)c2)cc(OC)c1OC]

N-(3-(imidazo[2,1-b]thiazol-6-yl)phenylcarbamothioyl)-3,4,5-trimethoxybenzamide (I-d), with formula:

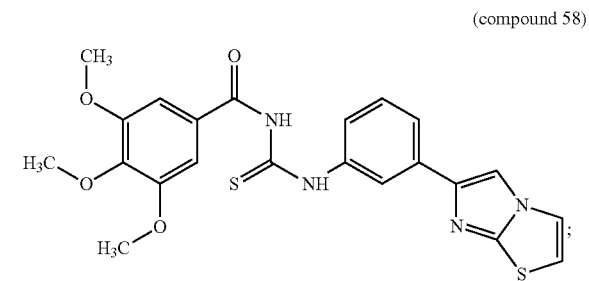 [SMILES: COc1cc(C(=O)NC(=S)Nc2cccc(-c3cn4ccsc4n3)c2)cc(OC)c1OC]

and
N-(3-(3-biphenyl-4-ylureido)phenylcarbamoyl)-3,4,5-trimethoxybenzamide (I-b') with formula:

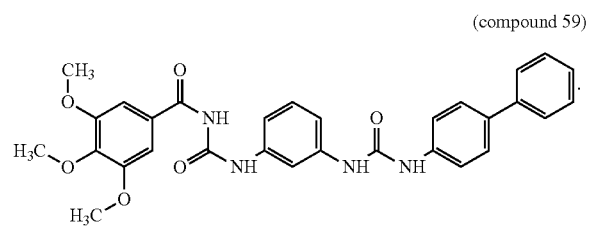 [SMILES: COc1cc(C(=O)NC(=O)Nc2cccc(NC(=O)Nc3ccc(-c4ccccc4)cc3)c2)cc(OC)c1OC]

Of these compounds, the following compounds are particularly preferred to the extent that they inhibit the activity of the Hedgehog protein signaling pathway with an inhibition of 80% or more, said inhibition being measured after activation of the Hedgehog protein signaling pathway with a synthetic chlorobenzothiophene type activator compound termed SAG (CAS No: 364590-63-6) using the method described by Chen et al., (Proc. Natl. Acad. Sci. USA, 2002, 99, 14071):

N-[[[3-(4-methoxy-benzoylamino)phenyl]amino]thioxomethyl]-3,4,5-methoxy-benzamide (I-a) (compound 1);
N-[[[3-(2-chloro-benzoylamino)phenyl]amino]thioxomethyl]-3,4,5-methoxy-benzamide (I-a) (compound 2);
N-[[[3-(3-methoxy-benzoylamino)phenyl]amino]thioxomethyl]-3,4,5-methoxy-benzamide (I-a) (compound 3);
N-[[[3-(2-methoxy-benzoylamino)phenyl]amino]thioxomethyl]-3,4,5-methoxy-benzamide (I-a) (compound 4);
N-[[[3-(4-methoxy-benzoylamino)phenyl]amino]oxomethyl]-3,4,5-methoxy-benzamide (I-a') (compound 6);
N-[[[3-(4-pyridocarboxylamino)phenyl]amino]thioxomethyl]-3,4,5-methoxy-benzamide (I-a) (compound 11);
N-[[[3-(4-chloro-benzoylamino)phenyl]amino]thioxomethyl]-3,4,5-methoxy-benzamide (I-a) (compound 13);
N-[[[3-(isopropoylcarboxylamino)phenyl]amino]oxomethyl]-3,4,5-methoxy-benzamide (I-a') (compound 17);
N-[[[3-(benzoylamino)phenyl]amino]thioxomethyl]-3,5-methoxy-benzamide (I-a) (compound 18);
N-[[[3-(benzoylamino)phenyl]amino]thioxomethyl]-3,5-methoxy-4-ethoxy-benzamide (I-a) (compound 19);
N-[[[3-(benzoylamino)phenyl]amino]thioxomethyl]-3,4-ethoxy-5-methoxy-benzamide (I-a) (compound 20);
N-[[[3-(benzoylamino)phenyl]amino]thioxomethyl]-3,4-methylenedioxy-5-methoxy-benzamide (I-a) (compound 21);
N-[[[3-(benzoylamino)phenyl]amino]thioxomethyl]-3,4,5-ethoxy-benzamide (I-a) (compound 23);
N-[[[4-fluoro-3-(benzoylamino)phenyl]amino]thioxomethyl]-3,4,5-methoxy-benzamide (I-a) (compound 24);
N-[[[4-chloro-3-(phenylamino)carbonyl]amino]thioxomethyl]-3,4,5-methoxy-benzamide (I-b) (compound 25);
N-[[[3-(benzoylamino)phenyl]amino]oxomethyl]-3,4,5-methoxy-benzamide (I-a') (compound 31);
N-[[[4-chloro-3-(benzoylamino)phenyl]amino]thioxomethyl]-3,4,5-methoxy-benzamide (I-a) (compound 34);
N-[[[3-(benzoylamino)phenyl]amino]thioxomethyl]-3,4,5-methoxy-benzamide (I-a) (compound 38);
N-[[[4-chloro-3-(4-dimethylamino-phenylamino)carbonyl]thioxomethyl]-3,4,5-methoxy-benzamide (I-b) (compound 39);
N-[[[4-chloro-3-(4-chloro-phenylamino)]carbonyl]phenylamino]thioxomethyl]-3,4,5-methoxy-benzamide (I-b) (compound 43);
N-[[[2-methyl-3-(benzoylamino)phenyl]amino]oxomethyl]-3,4,5-methoxy-benzamide (I-a') (compound 45);
N-[[[-3-(4-chloro-benzoylamino)phenyl]amino]oxomethyl]-3,4,5-methoxy-benzamide (I-a') (compound 47);
3,4,5-trimethoxy-N-(3-(3-phenylureido)phenylcarbamothioyl)benzamide (I-b) (compound 51),
N-(3-(3-biphenyl-4-ylureido)phenylcarbamothioyl)-3,4,5-trimethoxybenzamide (I-b) (compound 52);
N-(3-(1H-indol-2-yl)phenylcarbamoyl)-3,4,5-trimethoxybenzamide (I-d') (compound 53);
N-(3-(1H-indol-2-yl)phenylcarbamothioyl)-3,4,5-trimethoxybenzamide (I-d) (compound 54);
N-(3-(imidazo[1,2-a]pyridin-2-yl)phenylcarbamothioyl)-3,4,5-trimethoxybenzamide (I-d) (compound 55);
N-(3-(1H-indol-1-yl)phenylcarbamothioyl)-3,4,5-trimethoxybenzamide (compound 57);
N-(3-(imidazo[2,1-b]thiazol-6-yl)phenylcarbamothioyl)-3,4,5-trimethoxybenzamide (I-d) (compound 58); and
N-(3-(3-biphenyl-4-ylureido)phenylcarbamoyl)-3,4,5-trimethoxybenzamide (I-b') (compound 59).

The compounds with formula (I) as claimed in the invention can easily be prepared, generally in three or four steps, using synthesis methods analogous to conventional methods that are known to the skilled person.

The general synthesis scheme for compounds with formula (I) as claimed in the invention, in their four variations (I-a) or (I-a'), (I-b) or (I-b'), (I-c) or (I-c'), (I-d) or (I-d'), can be represented as shown in the accompanying FIG. 1.

In accordance with the synthesis scheme shown in the accompanying FIG. 1, in a step a), for obtaining compounds with the following formula (I-a) or (I-a'), a commercially available 3-nitroaniline with formula (II), wherein the radicals $R_4$ and $R_5$ have the meanings given above, is condensed with an acid chloride with formula (III), wherein $R_6$ has the meaning given hereinabove, for example using the Schotten-Baumann method, in order to obtain the corresponding amide compound with formula (IV). Step b) can be used to couple a commercially available 3-nitroaniline with formula (II), wherein the radicals $R_4$ and $R_5$ have the meanings given above, with a commercially available isocyanate (III'), in order to obtain a nitrourea with formula (IV') which can produce compounds (I-b) and (I-b'). Step b') consists in condensing a commercially available 3-nitrobenzoic acid with formula (II') with an amine with formula (V), wherein $R_4$, $R_5$ and $R_6$ have the meanings given above, in order to obtain the nitroamide compound with formula (IV").

Other conventional methods that are well known to the skilled person for forming an amide linkage may also be employed in order to carry out these condensation steps a), b) and b').

In steps c), c'), c") and d), the nitro group of the compounds with formula (IV), (IV') or (IV") is reduced to an amine in order respectively to obtain the anilines with formulas (VI), (VI') or (VI"). The 3-nitroaromatic compound (IV''') obtained during step d) has a mono- or polycyclic heteroaryl group Z, which is substituted or non-substituted, and radicals $R_4$ and $R_5$ having the meanings given hereinabove, are obtained using methods that are known to the skilled person (Yang et al., Angew. Chem. Int. Ed. 2008, 47, 1473; Burkholder et al., Tetrahedron Lett. 2001, 42, 3077; Zhang et al., J. Org. Chem., 2005, 70, 5164; Aggarwal et al., Synth. Comm. 2006, 36, 875; Rubin et al., International application PCT WO 2006/050506 in the name of CURIS), before undergoing a reduction in order to obtain the corresponding anilines (VI'''). This reduction step may be carried out in a reducing medium, for example by the action of a reducing agent such as lead dichloride or tin dichloride, or by hydrogenation using microwave activation, for example. Other hydrogenation methods may also be used depending on the nature of the substituents $R_4$ and $R_5$ that may be present on the phenyl ring. In this regard, when $R_4$ and/or $R_5$ represent a halogen atom such as chlorine, bromine or iodine, the reduction step is preferably carried out by the action of tin dichloride. In all other cases, it is preferable to carry out catalytic hydrogenation in the presence of Pd/C or Raney Nickel.

During steps e) and f), an acylisothiocyanate with formula (VIII) is prepared wherein the radicals $R_1$ to $R_3$ have the meaning given hereinabove for the compounds with formula (I), from a benzoic acid with formula (VII) or from a benzoic acid chloride with the corresponding formula (VII'), for example in a solvent medium under reflux (acetonitrile or acetone) in the presence, for example, of phosgene and ammonium thiocyanate. The compound with formula (VIII), a benzoylisothiocyanate, thus obtained is then coupled to a compound with formula (VI) or with formula (VI') in order to produce the corresponding compounds with formula (I) wherein X=S (acylthioureas), i.e. compounds with formulas (I-a) and (I-b). The same benzoylisocyanate (VIII) is condensed under reflux in a solvent, during steps g) and g'), with the anilines (VI") and (VI'''), to produce compounds with formula (I-c) and (I-d). Generally, the compounds with formulas (I-a) and (I-b) are obtained in the solid form and are then purified in conventional manner by re-crystallizing from an alcohol (Rasmussen, C. R. et al., Synthesis, 1988, 456-459).

When a compound with formula (I) is to be obtained wherein X=O, then in a step h), h'), h") or h'''), oxidation of a compound respectively with formula (I-a), (I-b), (I-c) or (I-d) is carried out to obtain a compound with formula (I-a'), (I-b'), (I-c') or (I-d'). This oxidation step may be carried out using methods that are well known to the skilled person, using, for example (Cu(I)) in an alkaline medium as the oxidizing agent (Narasimhamurthy, K. A et al., Tetrahedron Lett., 1982, 27, 3911) or other oxidizing agents such as iodic acid ($HIO_3$) supported on a resin (Yang, G et al., Green Chemistry, 2003, 5, 441-442). During the oxidation step, activation by microwave irradiation may be carried out in order to improve the oxidation.

The compounds with formulas (I-a'), (I-b'), (I-c') or (I-d') are also obtained in the form of solids that may then be purified by re-crystallization from an alcohol.

In a further aspect, the invention concerns acylthio-urea or acyl-urea derivatives that are novel per se, encompassed by formula (I) defined hereinabove, satisfying the following formula (I') (the compounds with formula (I') being a sub-family of the compounds with the following formula (I)):

wherein:

$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, a substituted alkoxy group, or a fused hererocycle obtained from two adjacent radicals $R_1$, $R_2$ and $R_3$ which can form a fused heterocycle together with the carbon atoms of the phenyl cycle to which they are bonded;

X represents a sulfur or oxygen atom;

Y represents a mono- or polycyclic heteroaryl group, which is substituted or non-substituted, a —NH—(C=O)—$R_6$ or —NH—(C=O)—NH—$R_6$ group wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;

$R_4$ and $R_5$, which are identical or different and independent of each other, represent a hydrogen or a halogen atom, or an alkoxy, alkylthio, alkyl, perfluoroalkyl, nitrile or nitro group;

it being understood that when Y represents a —NH—(C=O)—$R_6$ group or a —NH—(C=O)—NH—$R_6$ group, X represents a sulfur atom.

The compounds with formula (I') as claimed in the invention have the property of inhibiting the Hedgehog protein signaling pathway and can thus be used, as active principle, for the preparation of a pharmaceutical composition for the treatment of pathologies associated with a hyperactivation of the Hedgehog protein signaling pathway or wherein an inhibition of this pathway is of therapeutic interest.

In consequence, the present invention also concerns compounds with formula (I') as defined above for use as a drug, in particular:

i) as a drug intended for the treatment of tumors associated with a hyperactivation of the Hedgehog protein signaling pathway; such tumors are in particular nerve tissue tumors (medulloblastomas, primitive neuroectodermal tumors, glioblastomas, meningiomas and oligodendrogliomas), cutaneous tumors (basocellular carcinomas, trichoepitheliomas), bone and muscle tissue tumors (rhabdomyosarcomas, osteosarcomas) and tumors of other tissues (kidney, bladder).

ii) as a drug intended for the treatment of pathologies necessitating a blockage of the Hedgehog pathway, in particular pathologies of the neuro-degenerative type such as Parkinson's disease, Huntington's chorea, Alzheimer's disease, multiple sclerosis and motor neuron disease or other pathologies wherein blockage of the Hedgehog signaling pathway could be beneficial, such as diabetes.

The posology employed will depend on the function of the disorder to be treated, the route and frequency of administration, and on the nature and weight of the species to be treated (human or animal); it may, for example, be from 1 mg to 2 g per day in the adult for oral administration.

In a further aspect, the present invention is a pharmaceutical composition, characterized in that it comprises, as an active principle, at least one compound with formula (I') as defined above, and at least one pharmaceutically acceptable excipient.

In pharmaceutical compositions as claimed in the invention, the compound or compounds with formula (I') are preferably used in a quantity allowing unitary doses in the range approximately 1 mg to 2 g to be administered.

The skilled person will select one or more pharmaceutically acceptable excipients as a function of the mode of administration of the pharmaceutical composition. Clearly, the skilled person will take care at that time that the excipient or excipients used will be compatible with the intrinsic properties of the composition of the present invention.

Furthermore, the form of the drug or the pharmaceutical composition (for example, a solution, a suspension, an emulsion, tablets, gelules, suppositories, etc. . . . ) will depend on the selected mode of administration.

Thus, in the context of the present invention, the drug or the pharmaceutical composition may be administered using any appropriate mode, for example orally, anally, locally, systemically, intravenously, intramuscularly, or via the mucosae, or using a patch, or again in an encapsulated form in or immobilized on liposomes, microparticles, microcapsules and the like.

Non-limiting examples of suitable excipients for oral administration that may be cited are talc, lactose, starch and its derivatives, cellulose and its derivatives, polyethylene glycols, acrylic acid polymers, gelatin, magnesium stearate, animal, vegetable or synthetic fats, paraffin derivatives, glycols, stabilizers, preservatives, anti-oxidants, wetting agents, anti-caking agents, dispersing agents, emulsifying agents, taste modifying agents, penetration agents, solubilizing agents, etc.

Techniques for formulating and administering the drugs and pharmaceutical compositions are well known in the art under consideration here; in particular, the skilled person can consult the latest edition of Remington's Pharmaceutical Sciences.

Figure 2:
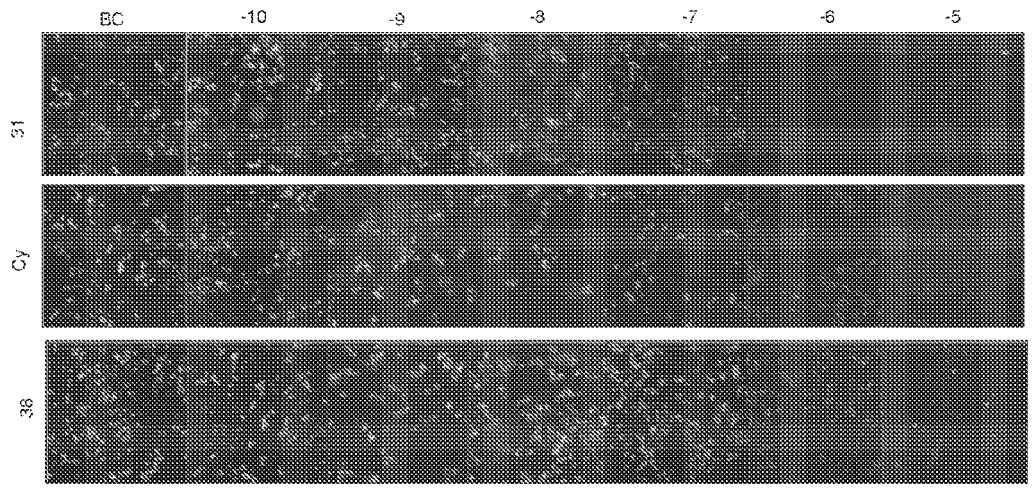
FIG. 2 are photographic images taken with a fluorescence microscope that show inhibition of Bodipycyclopamine binding of compounds of the invention.
Figure 3:
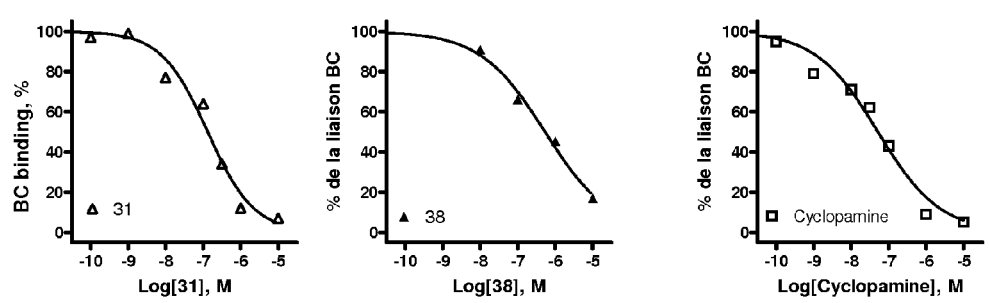
FIG. 3 shows dose-response curves obtained for compounds in accordance with the present invention, and for Cyclopamine (Cy), on Bodipycyclopamine binding.

In addition to the above considerations, the invention also encompasses other considerations that will become apparent from the following description made with reference to the examples of the synthesis of the compounds of the invention, to an example of producing the compounds of the invention, and to the accompanying drawings in which:

FIG. 1 shows the general synthesis scheme for the compounds of the invention;

FIG. 2 shows, using photographs taken with a fluorescence microscope (DMRXA2, Leica; openlab 3.1.2 software from Improvision), inhibition of Bodipycyclopamine binding of compounds 31 and 38 of the invention, as well as that with Cyclopamine (Cy), a reference antagonist for the Smoothened receptor, and FIG. 3 shows dose-response curves obtained for compounds 31 and 38 of the invention, and for Cyclopamine (Cy), on Bodipycyclopamine binding.

EXAMPLE 1

Synthesis of Various Compounds with Formula (I)

In these examples, the reactions were carried out in an inert gas atmosphere (nitrogen) using Schlenk (standard) methods. The solvents were dried using standard methods and distilled under nitrogen before use. All of the reagents were commercially available and used as they were, with no prior purification.

The mass spectrographs (ESI+) were recorded on a LC/MSD spectrometer marketed with reference Agilent® 1100. The nuclear magnetic spectra (NMR) were recorded using a Bruker® AC200 apparatus at 200 MHz ($^1$H) or on a Bruker® AC400 apparatus at 400 MHz ($^1$H) or at 100 MH$_z$ ($^{13}$C).

1) Synthesis of Intermediates with Formula (IV)

The intermediates with formula (IV) as defined hereinabove were all synthesized in accordance with the principle specifically detailed hereinbelow for 4-methoxy-N-(3-nitrophenyl)benzamide with the following formula (IV-1):

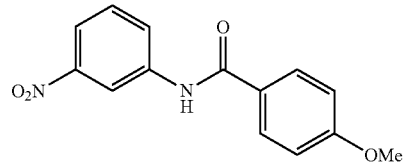

(IV-1)

0.88 g (1.21 mL, 8.69 mmol) of triethylamine was added dropwise to a solution of 3-nitroaniline (1 g, 7.24 mmol) in 10 mL of anhydrous dichloromethane (DCM). 5 mL of a solution of 4-methoxybenzoyl chloride (1.48 g, 1.19 mL, 8.69 mmol) in anhydrous DCM was added to the resulting solution, dropwise and over 5 minutes over an ice bath. The reaction medium was mixed at ambient temperature for 150 minutes; the reaction was monitored by thin layer chromatography (TLC) using a petroleum ether/ethyl acetate (AcOEt) 1/2 (v/v) mixture as the eluent. After the 3-nitroaniline had disappeared, the solution was poured into 5 mL of 1N hydrochloric acid (HCl). The resulting precipitate was washed with water and crystallized from methanol. 1.45 g of the anticipated compound with formula (IV-1) was obtained in the form of a brown solid (yield 74%).

[ES/MS] m/z 273 [M+1]$^+$, 295 [M+Na]$^+$ $^1$H-NMR 400 MHz (CDCl$_3$) δ (ppm): 8.45 (s, 1H); 8.07 (d, =8.4 Hz, 2H); 7.96 (dd, J1=8 Hz, J2=1.2 Hz, 1H); 7.85 (d, J=8.8 Hz, 2H); 7.51 (t, J=8 Hz, 1H); 6.97 (d, J=8.4 Hz, 2H); 3.86 (s, 3H).

The analyses obtained for the other compounds with formula (IV), synthesized by analogy using the method detailed hereinabove for the compound (IV-1), are given below:

Compound (IV-3):
3-methoxy-N-(3-nitrophenyl)benzamide

Brown solid, yield 71%.

[ES/MS] m/z 273 [M+1]$^+$, 295 [M+Na]$^+$ $^1$H-NMR 400 MHz (CDCl$_3$) δ (ppm): 8.48 (s, 1H); 8.28 (s, 1H); 8.05 (d, J=8 Hz, 1H); 7.95 (d, J=7.6 Hz, 1H); 7.49 (t, J=8 Hz, 1H); 7.41-7.35 (m, 4H); 3.83 (s, 3H).

Compound (IV-4):
2-Methoxy-N-(3-nitrophenyl)benzamide

Pale yellow solid, yield 75%
[ES/MS] m/z 273 [M+1]$^+$, 295 [M+Na]$^+$
$^1$H-NMR 400 MHz (CDCl$_3$) δ (ppm): 8.46 (s, 1H); 8.27 (dd, J1=8 Hz, J2=1.6 Hz, 1H); 8.11 (dd, J1=8 Hz, J2=1.6 Hz, 1H); 7.94 (dd, J1=8.8 Hz, J2=1.6 Hz, 1H); 7.54-7.47 (m, 3H); 7.14 (t, J=7.6 Hz, 1H); 7.04 (d, J=8.4 Hz, 1H); 4.08 (s, 3H).

Compound (IV-13):
4-chloro-N-(3-nitrophenyl)benzamide

Yellow solid, yield 94%.
[ES/MS] m/z 299 [M+Na]$^+$
$^1$H-NMR 400 MHz (CDCl$_3$) δ (ppm): 8.48 (s, 1H); 8.07 (d, J=8.4 Hz, 1H); 7.99 (d, J=8 Hz, 1H); 7.83 (d, J=8 Hz, 2H); 7.55-7.41 (m, 4H).

Compound (IV-32):
N-(2-methyl-3-nitrophenyl)benzamide

Yield 70%, melting point=132° C.
$^1$H-NMR 200 MHz (DMSO, d6) δ (ppm): 10.49 (s, 1 H); 8.20 (d, J=8 Hz, 2H); 8.03-7.67 (m, 6H); 2.50 (s, 3H).

2) Synthesis of Intermediates with Formula (VI)

The intermediates with formula (VI) as described above were all synthesized from corresponding compounds with formula (IV) using the specific principle detailed hereinbelow for 4-methoxy-N-(3-aminophenyl)benzamide with the following formula (VI-1):

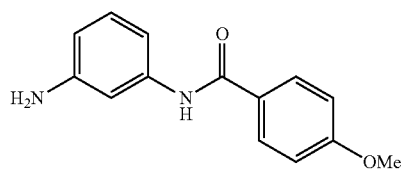

200 mg (0.74 mmol) of 4-methoxy-N-(3-nitrophenyl)benzamide (200 mg) was dissolved in 4 mL of anhydrous methanol in a microwave tube. 185 mg (2.94 mmol) of ammonium formate and 18.5 mg of Pd/C, in an amount of 10% as a catalyst, were then added to the solution obtained. The reaction medium was then irradiated in a microwave oven for 4 minutes at 80° C. Two cycles were carried out at a power of 50 W while monitoring the reaction by TLC using a petroleum ether/AcOEt mixture (1/2: v/v) as the eluent.

After elimination of the catalyst by filtration, and extensive washing with water then with methanol, the solution was evaporated off under vacuum. The residue was taken up in a mixture composed of saturated sodium carbonate (Na$_2$CO$_3$) and ethyl acetate. The organic phase was washed with a solution of saturated sodium chloride and dried over sodium sulfate sodium Na$_2$SO$_4$.

After eliminating the solvent under vacuum, 376 mg of the anticipated 4-methoxy-N-(3-nitrophenyl)benzamide with formula (VI-1) was obtained in the form of a solid (yield 75%). The product was then engaged in the subsequent reactions with no supplemental purification.

[ES/MS] m/z 243 [M+1]$^+$, 265 [M+Na]$^+$
$^1$H-NMR 400 MHz (CDCl$_3$) δ (ppm): 7.79 (d, J=8.4 Hz, 2H); 7.68 (s, 1H); 7.28 (s, 1H); 7.08 (t, J=8 Hz, 1H); 6.93 (d, J=8.4 Hz, 2H); 6.75 (d, J=8 Hz, 1H); 6.43 (d, J=8 Hz, 1H); 3.84 (s, 3H).

The analyses obtained for the other compounds with formula (VI), synthesized by analogy using the method detailed hereinabove for the compound (VI-1), are given below:

Compound (VI-3):
3-methoxy-N-(3-aminophenyl)benzamide

Brown solid, yield 86%.
[ES/MS] m/z 243 [M+1]$^+$, 265 [M+Na]$^+$, 507 [2M+Na]$^+$
$^1$H-NMR 400 MHz (CDCl$_3$) δ (ppm): 7.68 (s, 1H); 7.40-7.35 (m, 3H); 7.29 (s, 1H); 7.12-7.04 (m, 2H); 6.76 (d, J=7.6 Hz, 1H); 6.46 (dd, J1=8.4 Hz, J2=2 Hz, 1H); 3.85 (s, 3H).

Compound (VI-4):
2-methoxy-N-(3-aminophenyl)benzamide

Brown solid, yield 70%.
[ES/MS] m/z 243 [M+1]$^+$, 265 [M+Na]$^+$, 507 [2M+Na]$^+$

Compound (VI-5):
N-(3-aminophenyl)biphenyl-4-carboxamide

Brown solid, yield 98%.
[ES/MS] m/z 289 [M+1]$^+$, 312 [M+Na]$^+$, 599 [2M+Na]$^+$
$^1$H-NMR 400 MHz (CDCl$_3$) δ (ppm): 7.92 (d, J=8 Hz, 2H); 7.70-7.60 (m, 5H); 7.48-7.33 (m, 4H); 7.12 (t, J=8 Hz, 1H); 6.78 (d, J=8 Hz, 1H); 6.47 (dd, J1=8 Hz, J2=1.6 Hz, 1H).

3) Synthesis of Chlorinated Intermediates with Formula (VI)

The chlorinated intermediates with formula (VI) as described above were all synthesized from the corresponding chlorinated compounds with formula (IV) in accordance with the specific principle detailed hereinbelow for 4-chloro-N-(3-aminophenyl)benzamide with the following formula (VI-2):

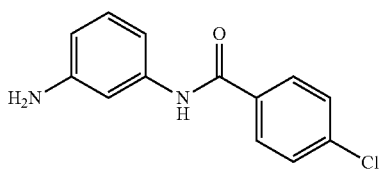

500 mg (1.81 mmol) of 4-chloro-N-(3-nitrophenyl)benzamide was dissolved in 50 mL of anhydrous ethanol. When dissolution was complete, 0.3 mL (3.62 mmol) of concentrated HCl and 1 g (5.43 mmol) of SnCl$_2$ were added. The reaction mixture was then heated to 60° C. for 5 hours, monitoring the formation of the anticipated product by TLC using a petroleum ether/AcOEt (1/2, v/v) mixture as the eluent. When the reaction had finished, a saturated solution of NaHCO$_3$ was added to the reaction medium. After elimination of the ethanol under vacuum, the reaction medium was extracted with ethyl acetate. After filtration, the organic phases were dried over Na$_2$SO$_4$. 440 mg of the compound with formula (VI-2) (yield 94%) was obtained in the form of a brown solid. This compound was then engaged in the subsequent synthesis steps with no supplemental purification.

[ES/MS] m/z 247 [M+1]+, 269 [M+Na]+

The analysis obtained for another compound with formula (VI), synthesized by analogy using the method detailed hereinabove for the compound (VI-2), is given below:

Compound (VI-13):
4-chloro-N-(3-aminophenyl)benzamide

Brown solid, yield 94%.
[ES/MS] m/z 247 [M+1]+, 269 [M+Na]+

4) Synthesis of Compounds with Formula (I-a)

The compounds with formula (I-a) as described above were all synthesized from the corresponding compounds with formula (VII') and (VI) in accordance with the specific principle detailed below for a compound with particular formula (I-a), N-[[[3-(4-methoxy-benzoylamino)phenyl]amino]thioxomethyl]-3,4,5-methoxy-benzamide with the following formula:

(compound 1)

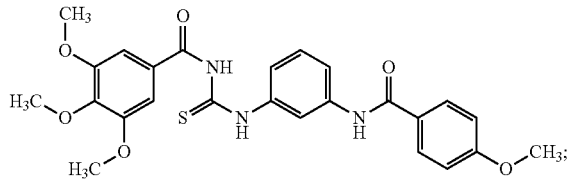

125 mg (1.63 mmol) of ammonium thiocyanate was dissolved in 4 mL of anhydrous acetone. After mixing, 330 mg (1.36 mmol) of 3,4,5-trimethoxybenzoyl chloride (compound with formula (VII')) was added to this solution, and the reaction mixture was heated under reflux for 20 minutes. After the solution had become clear, 314 mg (1.35 mmol) of 4-methoxy-N-(3-aminophenyl)benzamide (compound with formula (VI-1) as prepared hereinabove) was added, and the reaction medium was heated under reflux for 60 minutes. The reaction was monitored by TLC using a petroleum ether/AcOEt (1/4: v/v) mixture as the eluent. After the starting compound with formula (VI-1) had completely disappeared, the reaction medium was poured into a beaker containing ice. A precipitate was formed. The precipitate was then filtered and re-crystallized from methanol to produce 357 mg of the anticipated compound (1) in the form of a bright yellow solid (yield 53%).

[ES/MS] m/z 496 [M+1]+, 518 [M+Na]+, 1013 [2M+Na]+
$^1$H-NMR 400 MHz (CDCl$_3$) δ (ppm): 8.97 (s, 1H); 8.19 (s, 1H); 7.83 (d, J=8 Hz, 2H); 7.77 (s, 1H); 7.65-7.55 (m, 1H); 7.40-7.39 (m, 2H); 7.07 (s, 2H); 6.97 (d, J=8.8 Hz, 2H); 3.93 (s, 9H); 3.86 (s, 3H).

Other compounds with formula (I-a) were then synthesized from the corresponding intermediates:

Compound (2): N-[[[3-(2-chloro-benzoylamino)phenyl]amino]thioxomethyl]-3,4,5-methoxy-benzamide Bright yellow solid, yield 70%.
[ES/MS] m/z 501 [M+1]+, 521 [M+Na]+, 1022 [2M+Na]+
$^1$H-NMR 400 MHz (CDCl$_3$) δ (ppm): 8.96 (s, 1H); 8.17 (s, 1H); 7.92 (s, 1H); 7.68 (d, J=8 Hz, 1H); 7.60 (d, J=8 Hz, 1H); 7.47-7.40 (m, 5H); 7.06 (s, 2H); 3.93 (s, 9H).

Compound (3) N-[[[3-(3-methoxy-benzoylamino)phenyl]amino]thioxomethyl]-3,4,5-methoxy-benzamide Pale yellow solid, yield 70%.
[ES/MS] m/z 496 [M+1]+, 518 [M+Na]+, 1013 [2M+Na]+
$^1$H-NMR 400 MHz (CDCl$_3$) δ (ppm): 9.00 (s, 1H); 8.20 (s, 1H); 7.88 (s, 1H); 7.59 (bd, 1H); 7.43-7.37 (m, 5H); 7.07 (s, 3H); 3.93 (s, 9H); 3.86 (s, 3H).

Compound (4): N-[[[3-(2-methoxy-benzoylamino)phenyl]amino]thioxomethyl]-3,4,5-methoxy-benzamide Brown solid, yield 71%.
[ES/MS] m/z 496 [M+1]+, 518 [M+Na]+, 1013 [2M+Na]+
$^1$H-NMR 400 MHz (CDCl$_3$) δ (ppm): 9.88 (s, 1H); 9.02 (s, 1H); 8.27 (d, J=7.6 Hz, 1H); 8.16 (s, 1H); 7.60 (d, J=8 Hz, 1H); 7.49-7.40 (m, 2H); 7.39 (t, J=8.4 Hz, 1H); 7.13-7.02 (m, 4H); 4.06 (s, 3H); 3.93 (s, 9H).

Compound (13): N-[[[3-(4-chloro-benzoylamino)phenyl]amino]thioxomethyl]-3,4,5-methoxy-benzamide White solid, yield 70%.
[ES/MS] m/z 521 [M+Na]+
$^1$H-NMR 400 MHz (CDCl$_3$) δ (ppm): 8.97 (s, 1H); 8.21 (s, 1H); 7.84-7.80 (m, 3H); 7.58 (bd, 1H); 7.47-7.41 (m, 4H); 7.06 (s, 2H); 3.93 (s, 9H).

The other compounds of type (I-b), (I-c) and (I-d) were obtained in an analogous manner.

5) Synthesis of Compounds with Formula (I-a')

The various compounds with formula (I-a') were obtained by oxidation of the corresponding compounds with formula (I-a).

The preparation of N-[[[3-(4-methoxy-benzoylamino)phenyl]amino]oxomethyl]-3,4,5-methoxy-benzamide (compound (6)) from compound (1) will now be described in detail.

100 mg (0.20 mmol) of compound (1) as prepared hereinabove was suspended in 2 mL of acetonitrile (MeCN). This suspension was added dropwise to 2 mL of a solution of copper chloride (20 mg, 0.2 mmol) in acetonitrile that had previously been prepared in a microwave tube. 80 μl (0.2 mmol) of a 2.5 M sodium hydroxide solution was then added to the mixture obtained.

The tube was then placed in a microwave oven and underwent two successive cycles of irradiation under the following regimen:
  pressure: 350 K Pa,
  power: 200 W,
  temperature 120° C.,
  adjustment time for the parameter set: 1 min.,
  hold time for parameters: 6 min.

At the end of the reaction, the crude product obtained was diluted with dichloromethane, and the organic phase (colored blue) was washed with a 30% (v/v) aqueous ammoniacal solution until the blue color in the aqueous phase disappeared. The organic phase was then dried, filtered and evaporated under vacuum to produce a crude product that was purified by "flash" chromatography using a petroleum ether/ethyl acetate mixture in a proportion that changed gradually from 95/5 to 1/1. 80 mg of the anticipated compound (6) was obtained in the form of a brown solid, with a yield of 72%.

[ES/MS] m/z 521 [M+Na]$^+$ $^1$H-NMR 400 MHz (CDCl$_3$) δ (ppm): 8.77 (s, 1H); 8.18 (s, 1H); 7.80 (d, J=8 Hz, 2H); 7.71 (s, 1H); 7.65-7.50 (m, 1H); 7.40-7.30 (m, 2H); 7.00 (s, 2H); 6.90 (d, J=8 Hz, 2H); 3.90 (s, 9H); 3.85 (s, 3H).

The other compounds of type (I-b'), (I-c') and (I-d') were obtained in analogous manner.

Physical Parameters of Compounds with Formula (I) as Claimed in the Invention:

Compound (1): N-[[[3-(4-methoxy-benzoylamino)phenyl]amino]thioxomethyl]-3,4,5-methoxy-benzamide (C$_{25}$H$_{25}$N$_3$O$_6$S):
Molecular Weight (MW)=495; [ES/MS] m/z 518 [M+Na]$^+$; melting point (mp)=147° C.

Compound (2): N-[[[3-(2-chloro-benzoylamino)phenyl]amino]thioxomethyl]-3,4,5-methoxy-benzamide (C$_{24}$H$_{22}$ClN$_3$O$_5$):
MW=499; [ES/MS] m/z 522 [M+Na]$^+$; mp=178° C.

Compound (3): N-[[[3-(3-methoxy-benzoylamino)phenyl]amino]thioxomethyl]-3,4,5-methoxy-benzamide (C$_{25}$H$_{25}$N$_3$O$_6$S):
MW=495; [ES/MS] m/z 518 [M+Na]$^+$; mp=121° C.

Compound (4): N-[[[3-(2-methoxy-benzoylamino)phenyl]amino]thioxomethyl]-3,4,5-methoxy-benzamide (C$_{25}$H$_{25}$N$_3$O$_6$S):
MW=495; [ES/MS] m/z 518 [M+Na]$^+$; mp=137° C.

Compound (5): N-[[[3-(4-phenyl-benzoylamino)phenyl]amino]thioxomethyl]-3,4,5-methoxy-benzamide (C$_{30}$H$_{27}$N$_3$O$_5$S):
MW=541; [ES/MS] m/z 542 [M+H]$^+$ 564 [M+Na]$^+$; mp=144° C.

Compound (6): N-[[[3-(4-methoxy-benzoylamino)phenyl]amino]oxomethyl]-3,4,5-methoxy-benzamide (C$_{25}$H$_{25}$N$_3$O$_6$S):
MW=479; [ES/MS] m/z 502 [M+Na]$^+$; mp=167° C.

Compound (7): N-[[[3-(4-phenyl-benzoylamino)phenyl]amino]oxomethyl]-3,4,5-methoxy-benzamide (C$_{30}$H$_{27}$N$_3$O$_6$):
MW=525; [ES/MS] m/z 548 [M+Na]$^+$; mp=180° C. (with decomposition).

Compound (8): N-[[[3-(-cyclohexylcarboxylamino)phenyl]amino]thioxomethyl]-3,4,5-methoxy-benzamide (C$_{24}$H$_{29}$N$_3$O$_5$S):
MW=471; [ES/MS] m/z 494 [M+Na]$^+$; mp=67° C.

Compound (9): N-[[[3-(2-naphthoylamino)phenyl]amino]thioxomethyl]-3,4,5-methoxy-benzamide (C$_{28}$H$_{25}$N$_3$O$_5$S):
MW=515; [ES/MS] m/z 538 [M+Na]$^+$; mp=140° C.

Compound (10): N-[[[3-(isopropoylcarboxylamino)phenyl]amino]thioxomethyl]-3,4,5-methoxy-benzamide (C21H$_{25}$N$_3$O$_5$S):
MW=431; [ES/MS] m/z 454 [M+Na]$^+$; mp=102° C. (with decomposition).

Compound (11): N-[[[3-(4-pyridocarboxylamino)phenyl]amino]thioxomethyl]-3,4,5-methoxy-benzamide (C$_{23}$H$_{22}$N$_4$O$_5$S):
MW=466; [ES/MS] 467[M+H]$^+$ m/z 489 [M+Na]$^+$; mp=187° C. (with decomposition).

Compound (12): N-[[[3-(1-naphthoylamino)phenyl]amino]thioxomethyl]-3,4,5-methoxy-benzamide (C$_{28}$H$_{25}$N$_3$O$_5$S):
MW=515; [ES/MS] m/z 538 [M+Na]$^+$; mp=139° C.

Compound (13): N-[[[3-(4-chloro-benzoylamino)phenyl]amino]thioxomethyl]-3,4,5-methoxy-benzamide (C$_{24}$H$_{22}$ClN$_3$OS):
MW=499; [ES/MS] m/z 522 [M+Na]$^+$; mp=151° C.

Compound (14): N-[[[3-(2-furoylamino)phenyl]amino]thioxomethyl]-3,4,5-methoxy-benzamide (C$_{22}$H$_{21}$N$_3$O$_6$S):
MW=455; [ES/MS] m/z 456 [M+H]$^+$ 478 [M+Na]$^+$; mp=94° C.

Compound (15): N-[[[3-(2-thiophenoylamino)phenyl]amino]thioxomethyl]-3,4,5-methoxy-benzamide (C$_{22}$H$_{21}$N$_3$O$_5$S$_2$):
MW=471; [ES/MS] m/z 472[M+H]$^+$ 494 [M+Na]$^+$; mp=>150° C. (with decomposition).

Compound (16): N-[[[3-(2-naphthoylamino)phenyl]amino]oxomethyl]-3,4,5-methoxy-benzamide (C$_{28}$H$_{25}$N$_3$O$_6$):
MW=499; [ES/MS] m/z 522 [M+Na]$^+$; mp=188° C.

Compound (17): N-[[[3-(isopropoylcarboxylamino))phenyl]amino]oxomethyl]-3,4,5-methoxy-benzamide (C$_{21}$H$_{25}$N$_3$O$_6$):
MW=415; [ES/MS] m/z 438 [M+Na]$^+$.

Compound (18): N-[[[3-(benzoylamino)phenyl]amino]thioxomethyl]-3,5-methoxy-benzamide (C$_{23}$H$_{21}$N$_3$O$_4$S):
MW=435; [ES/MS] m/z 436 [M+1]$^+$; mp=194° C.

Compound (19): N-[[[3-(benzoylamino)phenyl]amino]thioxomethyl]-3,5-methoxy-4-ethoxy-benzamide (C$_{25}$H$_{25}$N$_3$O$_5$S):
MW=479; [ES/MS] m/z 480 [M+1]$^+$; mp=192° C.

Compound (20): N-[[[3-(benzoylamino)phenyl]amino]thioxomethyl]-3,4-ethoxy-5-methoxy-benzamide (C$_{26}$H$_{27}$N$_3$O$_5$S):
MW=493; [ES/MS] m/z 494 [M+1]$^+$; mp=172° C.

Compound (21): N-[[[3-(benzoylamino)phenyl]amino]thioxomethyl]-3,4-methylenedioxy-5-methoxy-benzamide (C$_{23}$H$_{19}$N$_3$O$_5$S):
MW=449; [ES/MS] m/z 450 [M+1]$^+$; mp=206° C.

Compound (22): N-[[[3-(benzoylamino)phenyl]amino]thioxomethyl]-2,4-methoxy-benzamide (C$_{23}$H$_{21}$N$_3$O$_4$S):
MW=435; [ES/MS] m/z 436 [M+1]$^+$; mp 210° C.

Compound (23): N-[[[3-(benzoylamino)phenyl]amino]thioxomethyl]-3,4,5-ethoxy-benzamide (C$_{27}$H$_{29}$N$_3$O$_5$S):
MW=507; [ES/MS] m/z 508 [M+1]$^+$; mp=176° C.

Compound (24): N-[[[4-fluoro-3-(benzoylamino)phenyl]amino]thioxomethyl]-3,4,5-methoxy-benzamide (C$_{24}$H$_{22}$FN$_3$O$_5$S):
MW=483; [ES/MS] m/z 484 [M+1]$^+$; mp=178° C.

Compound (25): N-[[[4-chloro-3-(phenylamino)carbonyl]amino]thioxomethyl]-3,4,5-methoxy-benzamide (C$_{24}$H$_{22}$N$_3$O$_5$S):
MW=499; [ES/MS] m/z 500 [M+1]$^+$; mp=174° C.

Compound (26): N-[[[4-methoxy-3-(benzoylamino)phenyl]amino]thioxomethyl]-3,4,5-methoxy-benzamide (C$_{25}$H$_{25}$N$_3$O$_6$S):
MW=495; [ES/MS] m/z 496 [M+1]$^+$; mp=186° C.

Compound (27): N-[[[4-methyl-3-(benzoylamino)phenyl]amino]thioxomethyl]-3,4,5-Methoxy-benzamide (C$_{25}$H$_{25}$N$_3$O$_5$S):
MW=479; [ES/MS] m/z 480 [M+1]$^+$; mp=190° C.

Compound (28): N-[[[3-(benzoylamino)phenyl]amino]thioxomethyl]-3,4-ethylenedioxo-benzamide (C$_{23}$H$_{19}$N$_3$O$_4$S):
MW=433; [ES/MS] m/z 434 [M+1]$^+$; mp=206° C.

Compound (29): N-[[[3-(benzoylamino)phenyl]amino]oxomethyl]-3,4,5-ethoxy-benzamide (C$_{27}$H$_{29}$N$_3$O$_6$):
MW=435; [ES/MS] m/z 436 [M+1]$^+$; mp=220° C.

Compound (30): N-[[[3-(benzoylamino)phenyl]amino]oxomethyl]-3,4-methylenedioxy-5-methoxy-benzamide (C$_{23}$H$_{19}$N$_3$O$_6$):
MW=433; [ES/MS] m/z 434 [M+1]$^+$; mp=252° C.

Compound (31): N-[[[3-(benzoylamino)phenyl]amino]oxomethyl]-3,4,5-methoxy-benzamide ($C_{24}H_{23}N_3O_6$): MW=449; [ES/MS] m/z 450 [M+1]$^+$; mp=216° C.

Compound (32): N-[[[3-methyl-3-(benzoylamino)phenyl]amino]thioxomethyl]-3,4,5-methoxy-benzamide ($C_{25}H_{25}N_3O_5S$): MW=479; [ES/MS] m/z 480 [M+1]$^+$; mp=207° C.

Compound (33): N-[[[4-chloro-3-(benzoylamino)phenyl]amino]oxomethyl]-3,4,5-methoxy-benzamide ($C_{24}H_{22}ClN_3O_6$): MW=483; [ES/MS] m/z 484 [M+1]$^+$; mp=244° C.

Compound (34): N-[[[4-chloro-3-(benzoylamino)phenyl]amino]thioxomethyl]-3,4,5-methoxy-benzamide ($C_{24}H_{22}ClN_3O_6S$): MW=499; [ES/MS] m/z 500 [M+1]$^+$; mp=174° C.

Compound (35): N-[[[5-chloro-3-(benzoylamino)phenyl]amino]thioxomethyl]-3,4,5-methoxy-benzamide ($C_{24}H_{22}ClN_3O_6S$): MW=499; [ES/MS] m/z 500 [M+1]$^+$; mp=164° C.

Compound (36): N-[[[5-fluoro-3-(benzoylamino)phenyl]amino]thioxomethyl]-3,4,5-methoxy-benzamide ($C_{24}H_{22}FN_3O_5$): MW=483; [ES/MS] m/z 484 [M+1]$^+$; mp=153° C.

Compound (37): N-[[[4-Chloro-3-(4-phenyl-benzoylamino)phenyl]amino]oxomethyl]-3,4,5-methoxy-benzamide ($C_{30}H_{26}ClN_3O_6$): MW=560; [ES/MS] m/z 561 [M+H]$^+$; mp=144° C.

Compound (38): N-[[[3-(benzoylamino)phenyl]amino]thioxomethyl]-3,4,5-methoxy-benzamide ($C_{24}H_{23}N_3O_5S$): MW=465, [ES/MS] m/z 466 [M+H]$^+$; mp=164° C.

Compound (39): N-[[[4-chloro-3-(4-dimethylamino-phenylamino)carbonyl]thioxomethyl]-3,4,5-methoxy-benzamide ($C_{26}H_{27}N_4ClO_5S$): MW=543; [ES/MS] m/z 544 [M+H]$^+$; mp=201° C.

Compound (40): N-[[[4-chloro-3-(4-methoxy-phenylamino)carbonyl]thioxomethyl]-3,4,5-methoxy-benzamide ($C_{25}H_{24}N_3ClO_6S$): MW=530; [ES/MS] m/z 531 [M+H]$^+$; mp=165° C.

Compound (41): N-[[[5-bromo-3-(phenylamino)carbonyl]thioxomethyl]-3,4,5-methoxy-benzamide ($C_{24}H_{22}BrN_3O_5S$): MW=544; [ES/MS] m/z 545 [M+H]$^+$; mp=196° C.

Compound (42): N-[[[4-chloro-3-(4-methoxy-phenylamino)carbonyl]oxomethyl]-3,4,5-methoxy-benzamide ($C_{25}H_{24}N_3ClO_7$): MW=513; [ES/MS] m/z 514 [M+H]$^+$; mp=135° C.

Compound (43): N-[[[4-chloro-3-(4-chloro-phenylamino)]carbonyl]phenylamino]thioxomethyl]-3,4,5-methoxy-benzamide ($C_{24}H_{21}Cl_2N_3O_5S$): MW=534; [ES/MS] m/z 535 [M+H]$^+$; mp=188° C.

Compound (44): N-[[[4-chloro-3-(phenylamino)carbonyl]oxomethyl]-3,4,5-methoxy-benzamide ($C_{24}H_{22}ClN_3O_6$): MW=483; [ES/MS] m/z 484 [M+H]$^+$; mp=160° C.

Compound (45): N-[[[2-methyl-3-(benzoylamino)phenyl]amino]oxomethyl]-3,4,5-methoxy-benzamide ($C_{31}H_{29}N_3O_6$): MW=539, [ES/MS] m/z 540 [M+H]$^+$; mp=181° C.

Compound (46): N-[[[2-methyl-3-(benzoylamino)phenyl]amino]thioxomethyl]-3,4,5-methoxy-benzamide ($C_{31}H_{29}N_3O_5S$): MW=555; [ES/MS] m/z 556 [M+H]$^+$; mp=181° C.

Compound (47): N-[[[-3-(4-chloro-benzoylamino)phenyl]amino]oxomethyl]-3,4,5-methoxy-benzamide ($C_{24}H_{22}ClN_3O_5S$): MW=539; [ES/MS] m/z 540 [M+H]$^+$; mp=156° C.

Compound (48): N-[[[-3-(benzoylamino)phenyl]amino]oxomethyl]-2,4,5-methoxy-benzamide ($C_{24}H_{23}N_3O_6$): MW=449; [ES/MS] m/z 550 [M+H]$^+$; mp=192° C.

Compound (49): N-[[[-3-(benzoylamino)phenyl]amino]oxomethyl]-4-methoxy-benzamide ($C_{22}H_{19}N_3O_4$): MW=389; [ES/MS] m/z 390 [M+H]$^+$; mp=264° C.

Compound (50): N-[[[-3-(benzoylamino)phenyl]amino]oxomethyl]-benzamide ($C_{21}H_{17}N_3O_3$): MW=359; [ES/MS] m/z 360 [M+H]$^+$; mp=244° C.

Compound (51): 3,4,5-trimethoxy-N-(3-(3-phenylureido)phenylcarbamothioyl)-benzamide ($C_{30}H_{20}N_4O_4S_2$): MW 556; [ES/MS] m/z 557 [M+H]$^+$; mp=220° C.

Compound (52): N-(3-(3-biphenyl-4-ylureido)phenylcarbamothioyl)-3,4,5-trimethoxybenzamide ($C_{24}H_{24}N_4O_5S$): MW 480; [ES/MS] m/z 481 [M+H]$^+$; mp=250° C.

Compound (53): N-(3-(1H-indol-2-yl)phenylcarbamoyl)-3,4,5-trimethoxybenzamide ($C_{25}H_{23}N_3O_5$): MW 445; [ES/MS] m/z 446 [M+H]$^+$; mp=169° C.

Compound (54): N-(3-(1H-indol-2-yl)phenylcarbamothioyl)-3,4,5-trimethoxybenzamide ($C_{25}H_{23}N_3O_4S$): MW 461; [ES/MS] m/z 462 [M+H]$^+$; mp=131° C.

Compound (55): N-(3-(imidazo[1,2-a]pyridin-2-yl)phenylcarbamothioyl)-3,4,5-trimethoxybenzamide ($C_{24}H_{22}N_4O_4$): MW 462; [ES/MS] m/z 463 [M+H]$^+$; mp=136° C.

Compound (56): N-(3-(1H-benzo[d]imidazol-2-yl)-4-methylphenylcarbamothioyl)-3,4,5-trimethoxybenzamide ($C_{25}H_{24}N_4O_4S$): MW 476; [ES/MS] m/z 477 [M+H]$^+$; mp=187° C.

Compound (57): N-(3-(1H-indol-1-yl)phenylcarbamothioyl)-3,4,5-trimethoxybenzamide ($C_{25}H_{23}N_3O_4S$): MW 461; [ES/MS] m/z 462 [M+H]$^+$; mp=131° C.

Compound (58): N-(3-(imidazo[2,1-b]thiazol-6-yl)phenylcarbamothioyl)-3,4,5-trimethoxybenzamide ($C_{22}H_{20}N_4O_4S_2$): MW 468; [ES/MS] m/z 469 [M+H]$^+$; mp=133° C.

Compound (59): N-(3-(3-biphenyl-4-ylureido)phenylcarbamoyl)-3,4,5-trimethoxybenzamide MW 525; [ES/MS] m/z 526 [M+H]$^+$; mp=183° C.

EXAMPLE 2

Determination of the Inhibitor Effect of Compounds with Formula (I) on the Hedgehog Protein Signaling Pathway The effect of compounds with formula (I) as claimed in the invention on inhibition of the Hedgehog protein signaling pathway was determined by analysis of differentiation in the pluripotent fibroblast cell line C3H10T1/2 after activation of this pathway in these cells using a synthetic activator: SAG.

1) Methods and Apparatus

The compounds with formula (I) to be tested were dissolved in dimethylsulfoxide to a concentration of 10 mM, then stored at a temperature of −20° C. until use.

The pluripotent fibroblast cell line C3H10T1/2 (ATCC) was cultivated under the conditions recommended by the ATCC. These cells were activated using 0.1 µM of SAG, employing the methods described by Chen et al., Proc. Natl. Acad. Sci. USA, 2002, 99, 14071 and Frank-Kamenetsky et al., J. Biol., 2002, 1, 10.

Activation with SAG provokes differentiation of the cell line and allows them to express alkaline phosphatase. It is then possible to measure the activity of the Hedgehog protein signaling pathway by measuring the alkaline phosphatase activity.

The C3H10T1/2 cells were plated onto 96-well plates at a density of $5\times10^5$ cells per well, 24 hours before addition of the test compounds in a concentration of 1 nM to 30 µM and in the presence of 0.1 µM of SAG using DMEM supplemented with 10% fetal calf serum as the culture medium. The tests were carried out in quadruplicate. The plates were then incubated for 5-6 days at a temperature of 37° C. in an atmosphere of 5% $CO_2$. The cells were washed in a cold phosphate buffer ("Phosphate Buffer Serum": PBS) then lysed by sonication at 4° C. in 50 µl of a solution containing 0.9% of NaCl and 0.2% of Triton X-100.

By way of comparison, the activity of a known inhibitor of the Hedgehog protein signaling pathway, CURIS 61 414, as described, for example, by Frank-Kamenetsky M. et al. (J. Biol., 2002, 1, 10), was tested under the same conditions as those used to test the various compounds with formula (I) as claimed in the invention.

The alkaline phosphatase activity measurement in the lysates obtained was then carried out using the method described by Pepinsky et al. (J. Biol. Chem., 1998, 273, 14037). After adding 100 µl of reaction buffer (200 mM Tris-HCl; pH 10.5; 0.4 M of 2-amino-2-methylpropanol and 8 mM of $MgCl_2$) and 50 µl of substrate (4 mM of disodium p-nitrophenyl phosphate), the lysates were incubated at 37° C. for 30-60 min, then the optical density was read at a wavelength of 415 nm.

2) Results

The results obtained are reported in Tables 1 and 2 below in which:

Table 1 presents the inhibition of alkaline phosphatase activity induced by 10 µM of each of the test compounds. These results are expressed as a percentage of the alkaline phosphatase activity induced by the action of SAG. In this table, the letter A corresponds to an inhibition of more than 80%, the letter B corresponds to an inhibition in the range 20% to 80% and the letter C corresponds to an inhibition in the range 5% to 20%;

Table 2 presents the test concentration for each of the compounds that can inhibit 50% of the alkaline phosphatase activity ($IC_{50}$) after induction by 0.1 µM SAG. In this table, the letter A corresponds to a $IC_{50}$ in the range 0.01 µM to 1 µM and the letter B corresponds to a $IC_{50}$ in the range 1 µM to 3 µM.

TABLE 1

| COMPOUNDS | % INHIBITION |
|---|---|
| 1 | A |
| 2 | A |
| 3 | A |
| 4 | A |
| 5 | B |
| 6 | A |
| 7 | B |
| 8 | B |
| 9 | B |
| 10 | C |
| 11 | A |
| 12 | B |
| 13 | A |
| 14 | B |
| 15 | B |
| 16 | C |
| 17 | A |
| 18 | A |
| 19 | A |
| 20 | A |
| 21 | A |
| 22 | B |
| 23 | A |
| 24 | A |
| 25 | A |
| 26 | B |
| 27 | B |
| 28 | C |
| 29 | B |
| 30 | C |
| 31 | A |
| 32 | B |
| 33 | B |
| 34 | A |
| 35 | B |
| 36 | B |
| 37 | B |
| 38 | A |
| 39 | A |
| 40 | B |
| 41 | B |
| 42 | B |
| 43 | A |
| 44 | B |
| 45 | A |
| 46 | C |
| 47 | A |
| 48 | B |
| 49 | B |
| 50 | A |
| 51 | A |
| 52 | A |
| 53 | A |
| 54 | A |
| 55 | A |
| 56 | B |
| 57 | A |
| 58 | A |
| 59 | A |

TABLE 2

| COMPOUNDS | $IC_{50}$ (µM) |
|---|---|
| Curis 61 414 (*) | A |
| 1 | B |
| 2 | B |
| 3 | B |
| 4 | B |
| 5 | A |
| 13 | A |
| 18 | B |
| 19 | A |
| 20 | A |
| 21 | B |
| 22 | B |
| 23 | A |
| 31 | A |
| 34 | A |
| 38 | A |
| 39 | B |
| 45 | A |
| 48 | B |
| 51 | B |
| 52 | A |
| 53 | A |
| 54 | A |
| 55 | A |
| 57 | B |
| 58 | B |

(*): reference compound not forming part of the invention

These results demonstrate that the compounds with formula (I) as claimed in the invention are antagonists of the Hedgehog protein signaling pathway and that in consequence they are useful for the treatment of pathologies necessitating blockage of the Hedgehog pathway such as cancer, neurodegenerative diseases and diabetes.

EXAMPLE 3

Competitive Bodipycyclopamine Binding

1) Methods and Apparatus

HEK293 cells were plated in a quantity of 70 000 cells per well onto glass cover slips treated with poly-D-lysine into 24-well plates, and transfected the next day with 0.25 µg of plasmid encoding the mouse Smoothened protein (Masdeu C., Faure H., Coulombe J., Schoenfelder A., Mann A., Brabet I., Pin J-P., Traiffort E. and Ruat M., Identification and characterization of Hedgehog modulator properties after functional coupling of Smoothened to G15, Biochem Biophys Res. Commun., 2006, 349:471-479), using 0.7 µL of fugene6 (Roche Biochemicals). After 48 hours, the culture medium was eliminated, the cells were rinsed once with 1 mL of a phosphate buffer solution, PBS (Phosphate Buffered Saline), then fixed for 20 minutes in the presence of an iced 4% solution of paraformaldehyde (PFA) and 0.12M glucose in a PBS phosphate buffer solution. The cells were then rinsed twice and washed twice for 5 minutes with 1 mL of a phosphate buffer solution and 0.5% of fetal calf serum (PBS-FCS). Next, 1 mL of Bodipycyclopamine (BC) (Chen, J. K., Taipale, J., Cooper, M. K., and Beachy, P. A., *Genes Dev.*, 2002, 16 (21), 2743-2748), diluted to 5 nM in PBS-FCS, in the presence of compounds 31 and 38 of the invention, was applied to the cells for 2 hours at 37° C. The cells were then washed twice for 5 minutes with 1 mL of PBS-FCS and brought into the presence of 1 mL of a PBS 1× phosphate buffer solution. Finally, the cover slips were mounted on a glass slide in the presence of Vectashield containing DAPI (4',6'-DiAmidino-2-Phenyl Indole) to stain the cell nuclei (Vector).

2) Results

The activity of a known inhibitor of the Hedgehog protein signaling pathway, Cyclopamine (Cy), was also tested under the same conditions as those used for compounds 31 and 38 of the invention.

The results obtained are shown in the accompanying FIGS. 2 and 3.

In FIG. 2, the intensity of the fluorescence was analyzed using Simple PCI 6.2 software (Hamamatsu Corporation), then related to the surface area of the nuclei present in the photograph. This intensity depended on the inhibition of the Bodipycyclopamine by the analyzed compounds.

Bodipycyclopamine binding competition was observed in the presence of compounds 31 and 38 of the invention, as well as with the Cyclopamine (Cy). FIGS. 2 and 3 indicate that the compounds 31 and 38 of the invention interact with the Smoothened receptor at the Bodipycyclopamine binding site.

The mean inhibiting concentrations, $IC_{50}$, obtained for compounds 31 and 38 of the invention, and for cyclopamine (Cy), are as follows:

for compound 31 of the invention: $IC_{50}$=0.12 µM;
for compound 38 of the invention: $IC_{50}$=0.5 µM; and
for cyclopamine (Cy): $IC_{50}$=0.05 µM.

These results demonstrate that the compounds of the invention are antagonists of the Hedgehog protein signaling pathway, and that they act on the Smoothened receptor.

The invention claimed is:

1. A method for manufacturing a drug, said method comprising mixing at least one pharmaceutically acceptable excipient and at least one compound with the following formula (I):

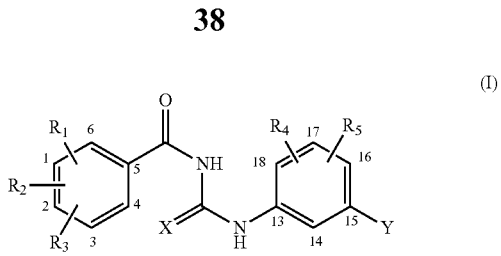

wherein:
$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, or a substituted alkoxy group;

X represents a sulfur or oxygen atom;

Y represents a a —NH—(C═O)—$R_6$, or —(C═O)—NH—$R_6$ group, wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;

$R_4$ and $R_5$, which are identical or different and independent of each other, represent a hydrogen or a halogen atom, or an alkoxy, alkylthio, alkyl, perfluoroalkyl, nitrile or nitro group.

2. A method for manufacturing a drug, said method comprising mixing at least one pharmaceutically acceptable excipient and at least one compound with the following formula (I):

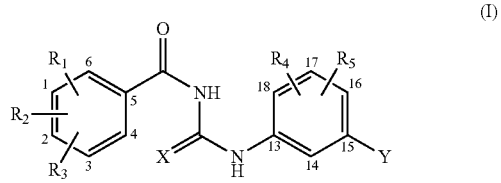

wherein:
$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, or a substituted alkoxy group;

X represents a sulfur or oxygen atom;

Y represents a a —NH—(C═O)—$R_6$, or —(C═O)—NH—$R_6$ group, wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;

$R_4$ and $R_5$, which are identical or different and independent of each other, represent a hydrogen or a halogen atom, or an alkoxy, alkylthio, alkyl, perfluoroalkyl or nitrile group;

it being understood that when Y represents a group —NH—(C═O)—$R_6$:

$R_4$ and/or $R_5$ can also represent a nitro group.

3. The method as claimed in claim 1, characterized in that the compound is selected from those in which, in the formula (I):

$R_1$, $R_2$, and $R_3$, which are identical or different, represent a hydrogen atom or a methyloxy or ethyloxy radical, X represents a sulfur or oxygen atom;

Y represents a or a —NH—(C=O)—$R_6$, or —(C=O)—NH—$R_6$ group, wherein $R_6$ represents a group selected from phenyl groups; phenyl substituted with a radical methoxy or dimethylamino, with a chlorine atom, with a phenyl group, with a benzyl, cyclohexyl, isopropyl, pyridinyl, naphthyl, furfuryl or thiophene group; and $R_4$ and $R_5$, which are identical or different, are selected from hydrogen, chlorine, bromine, fluorine, methyl and methoxy.

4. The method as claimed in claim 1, characterized in that the compound with formula (I) is selected from the group consisting of:

N-[[[3-(4-methoxy-benzoylamino)phenyl]amino]thioxomethyl]-3,4,5-methoxy-benzamide (I-a) with the following formula:

(compound 1)

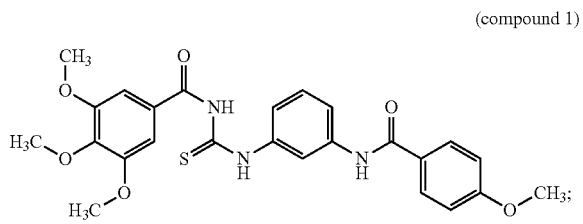 [SMILES: COc1ccc(C(=O)Nc2cccc(NC(=S)NC(=O)c3cc(OC)c(OC)c(OC)c3)c2)cc1]

N-[[[3-(2-chloro-benzoylamino)phenyl]amino]thioxomethyl]-3,4,5-methoxy-benzamide (I-a) with the following formula:

(compound 2)

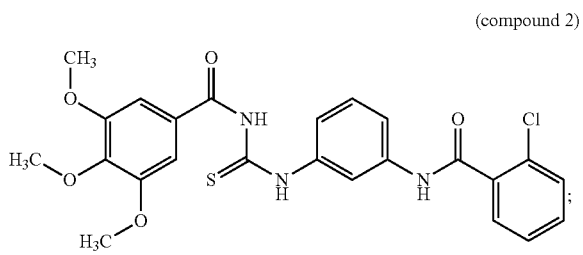 [SMILES: COc1cc(C(=O)NC(=S)Nc2cccc(NC(=O)c3ccccc3Cl)c2)cc(OC)c1OC]

N-[[[3-(3-methoxy-benzoylamino)phenyl]amino]thioxomethyl]-3,4,5-methoxy-benzamide (I-a) with the following formula:

(compound 3)

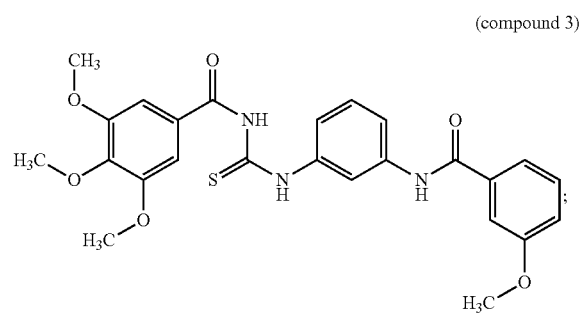 [SMILES: COc1cccc(C(=O)Nc2cccc(NC(=S)NC(=O)c3cc(OC)c(OC)c(OC)c3)c2)c1]

N-[[[3-(2-methoxy-benzoylamino)phenyl]amino]thioxomethyl]-3,4,5-methoxy-benzamide (I-a) with the following formula:

(compound 4)

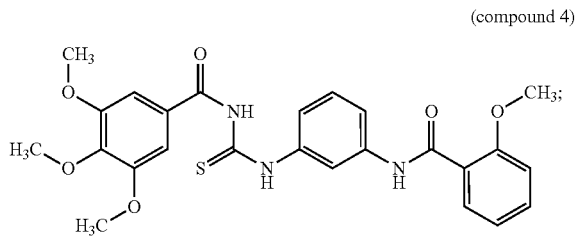 [SMILES: COc1ccccc1C(=O)Nc1cccc(NC(=S)NC(=O)c2cc(OC)c(OC)c(OC)c2)c1]

N-[[[3-(4-phenyl-benzoylamino)phenyl]amino]thioxomethyl]-3,4,5-methoxy-benzamide (I-a) with the following formula:

(compound 5)

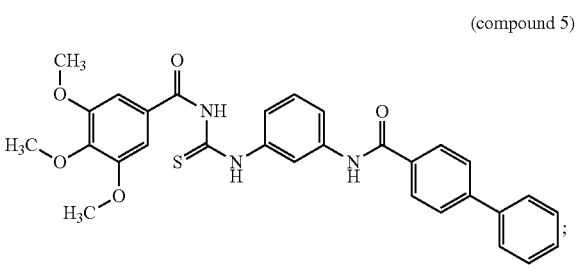

N-[[[3-(4-methoxy-benzoylamino)phenyl]amino]oxomethyl]-3,4,5-methoxy-benzamide (I-a') with the following formula:

(compound 6)

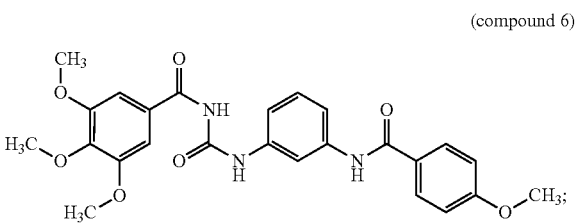

N-[[[3-(4-phenyl-benzoylamino)phenyl]amino]oxomethyl]-3,4,5-methoxy-benzamide (I-a') with the following formula:

(compound 7)

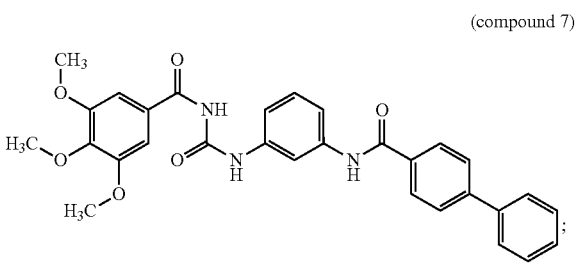 [SMILES: COc1cc(C(=O)NC(=O)Nc2cccc(NC(=O)c3ccc(-c4ccccc4)cc3)c2)cc(OC)c1OC]

N-[[[3-(-cyclohexylcarboxylamino)phenyl]amino]thioxomethyl]-3,4,5-methoxy-benzamide (I-a) with the following formula:

(compound 8)

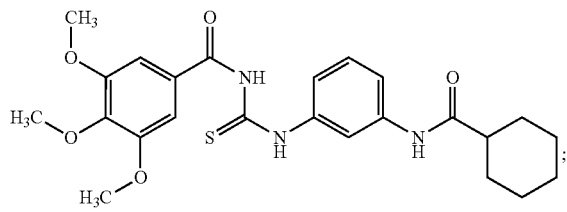

N-[[[3-(2-naphthoylamino)phenyl]amino]thioxomethyl]-3,4,5-methoxy-benzamide (I-a) with the following formula:

(compound 9)

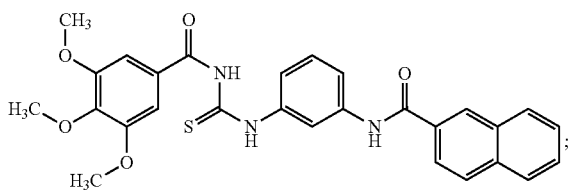

N-[[[3-(isopropoylcarboxylamino)phenyl]amino]thioxomethyl]-3,4,5-methoxy-benzamide (I-a) with the following formula:

(compound 10)

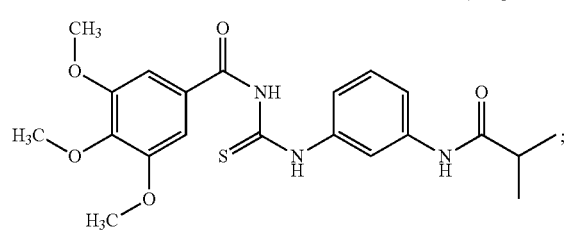

N-[[[3-(4-pyridocarboxylamino)phenyl]amino]thioxomethyl]-3,4,5-methoxy-benzamide (I-a) with the following formula:

(compound 11)

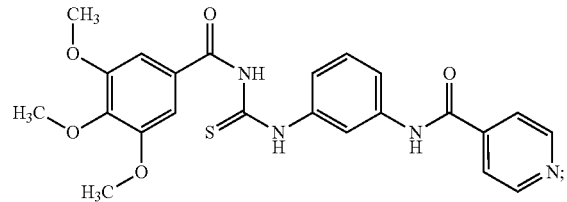

N-[[[3-(1-naphthoylamino)phenyl]amino]thioxomethyl]-3,4,5-methoxy-benzamide (I-a) with the following formula:

(compound 12)

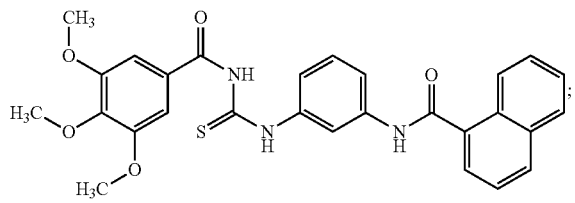

N-[[[3-(4-chloro-benzoylamino)phenyl]amino]thioxomethyl]-3,4,5-methoxy-benzamide (I-a) with the following formula:

(compound 13)

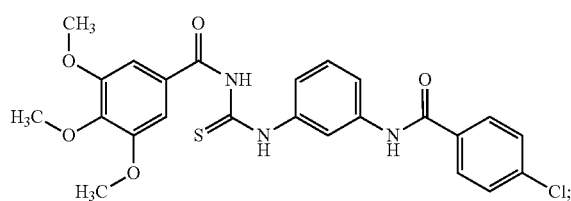

N-[[[3-(2-furoylamino)phenyl]amino]thioxomethyl]-3,4,5-methoxy-benzamide (I-a) with the following formula:

(compound 14)

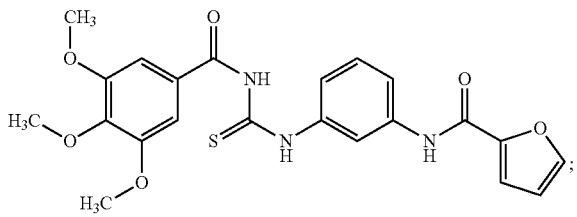

N-[[[3-(2-thiophenoylamino)phenyl]amino]thioxomethyl]-3,4,5-methoxy-benzamide (I-a) with the following formula:

(compound 15)

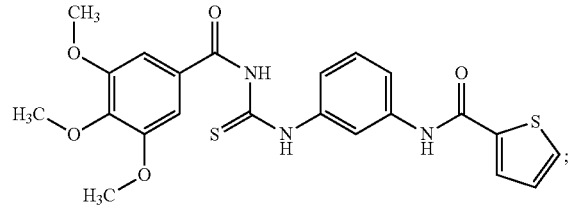

N-[[[3-(2-naphthoylamino)phenyl]amino]oxomethyl]-3,4,5-methoxy-benzamide (I-a') with the following formula:

(compound 16)

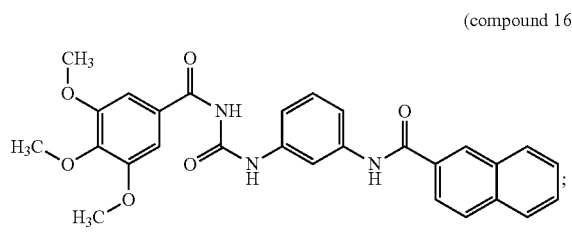

N-[[[3-(isopropoylcarboxylamino))phenyl]amino]oxomethyl]-3,4,5-methoxy-benzamide (I-a') with the following formula:

(compound 17)

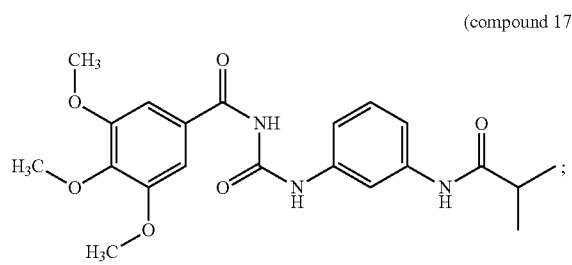 [SMILES: COc1cc(C(=O)NC(=S)Nc2cccc(NC(=O)C(C)C)c2)cc(OC)c1OC]

N-[[[3-(benzoylamino)phenyl]amino]thioxomethyl]-3,5-methoxy-benzamide (I-a) with the following formula:

(compound 18)

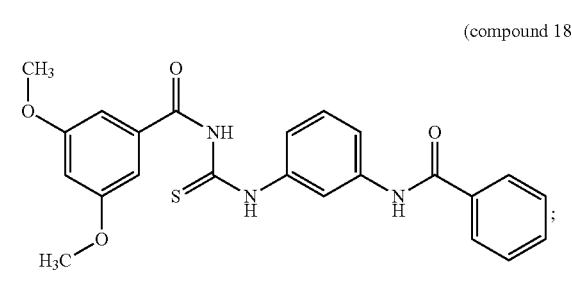

N-[[[3-(benzoylamino)phenyl]amino]thioxomethyl]-3,5-methoxy-4-ethoxy-benzamide (I-a) with the following formula:

(compound 19)

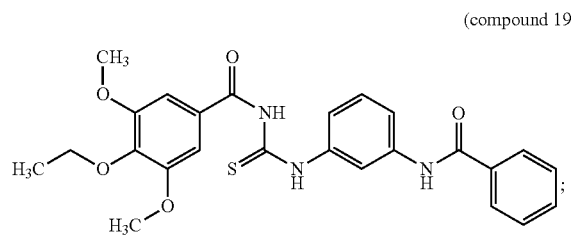

N-[[[3-(benzoylamino)phenyl]amino]thioxomethyl]-3,4-ethoxy-5-methoxy-benzamide (I-a) with the following formula:

(compound 20)

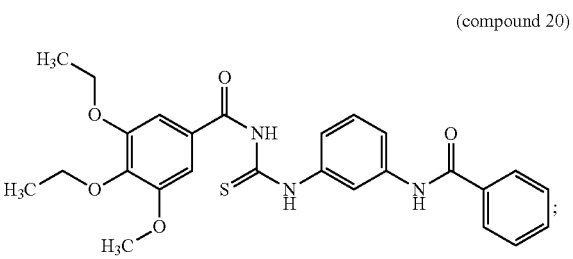 [SMILES: CCOc1cc(C(=O)NC(=S)Nc2cccc(NC(=O)c3ccccc3)c2)cc(OC)c1OCC]

N-[[[3-(benzoylamino)phenyl]amino]thioxomethyl]-2,4-methoxy-benzamide (I-a) with the following formula:

(compound 22)

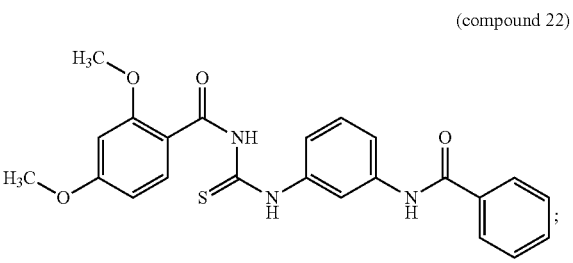 [SMILES: COc1ccc(C(=O)NC(=S)Nc2cccc(NC(=O)c3ccccc3)c2)c(OC)c1]

N-[[[3-(benzoylamino)phenyl]amino]thioxomethyl]-3,4,5-ethoxy-benzamide (I-a) with the following formula:

(compound 23)

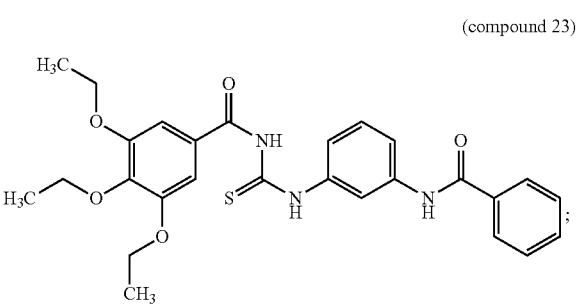 [SMILES: CCOc1cc(C(=O)NC(=S)Nc2cccc(NC(=O)c3ccccc3)c2)cc(OCC)c1OCC]

N-[[[4-fluoro-3-(benzoylamino)phenyl]amino]thioxomethyl]-3,4,5-methoxy-benzamide (I-a) with the following formula:

(compound 24)

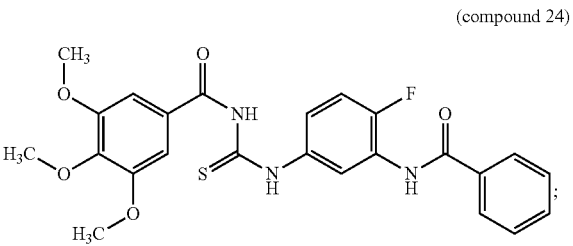

N-[[[4-chloro-3-(phenylamino)carbonyl]amino]thioxomethyl]-3,4,5-methoxy-benzamide (I-b) with the following formula:

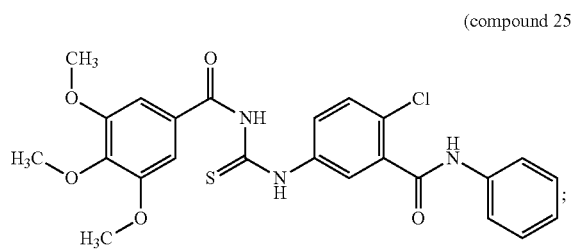

(compound 25)

N-[[[4-methoxy-3-(benzoylamino)phenyl]amino]thioxomethyl]-3,4,5-methoxy-benzamide (I-a) with the following formula:

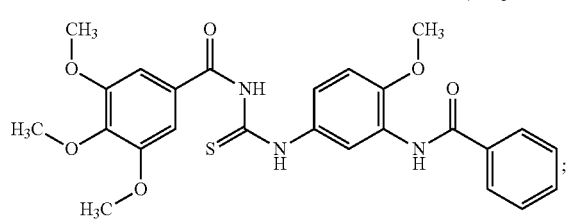

(compound 26)

N-[[[4-methyl-3-(benzoylamino)phenyl]amino]thioxomethyl]-3,4,5-methoxy-benzamide (I-a) with the following formula:

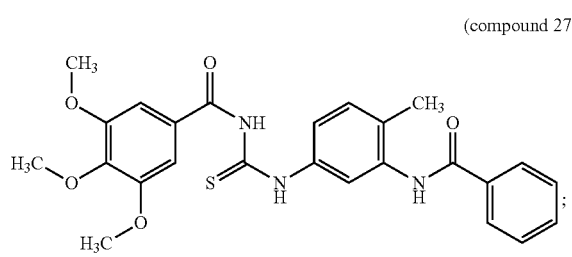

(compound 27)

N-[[[3-(benzoylamino)phenyl]amino]thioxomethyl]-3,4,5-ethoxy-benzamide (I-a') with the following formula:

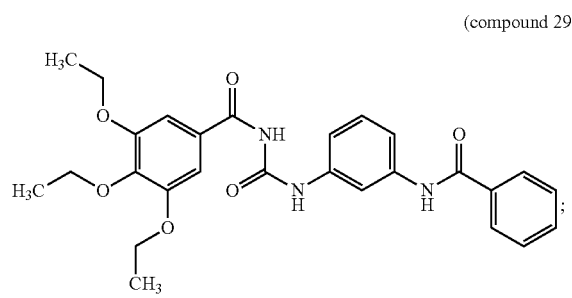

(compound 29)

N-[[[3-(benzoylamino)phenyl]amino]oxomethyl]-3,4,5-methoxy-benzamide (I-a') with the following formula:

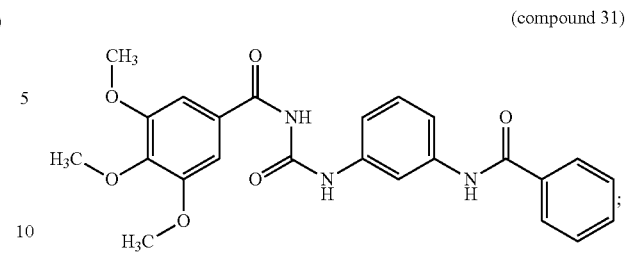

(compound 31)

N-[[[3-methyl-3-(benzoylamino)phenyl]amino]thioxomethyl]-3,4,5-methoxy-benzamide (I-a) with the following formula:

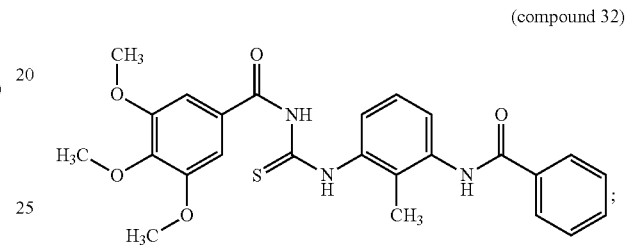

(compound 32)

N-[[[4-chloro-3-(benzoylamino)phenyl]amino]oxomethyl]-3,4,5-methoxy-benzamide (I-a') with the following formula:

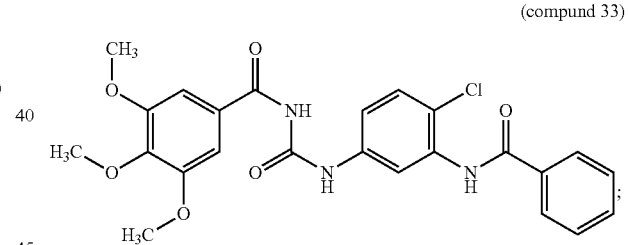

(compound 33)

N-[[[4-chloro-3-(benzoylamino)phenyl]amino]thioxomethyl]-3,4,5-methoxy-benzamide (I-a) with the following formula:

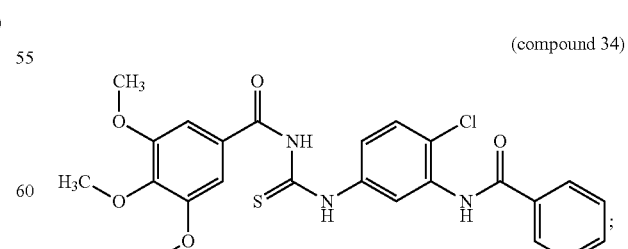

(compound 34)

N-[[[5-chloro-3-(benzoylamino)phenyl]amino]thioxomethyl]-3,4,5-methoxy-benzamide (I-a) with the following formula:

(compound 35)

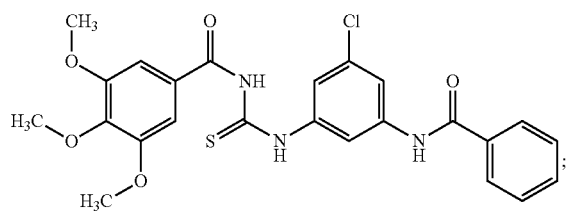

N-[[[5-fluoro-3-(benzoylamino)phenyl]amino]thioxomethyl]-3,4,5-methoxy-benzamide (I-a) with the following formula:

(compound 36)

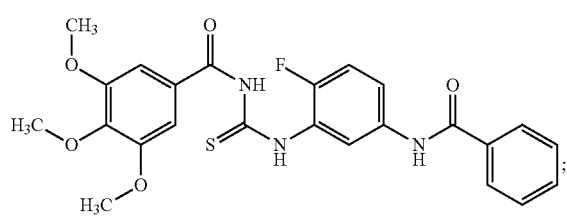

N-[[[4-chloro-3-(4-Phenyl-benzoylamino)phenyl]amino]oxomethyl]-3,4,5-methoxy-benzamide (I-a') with the following formula:

(compound 37)

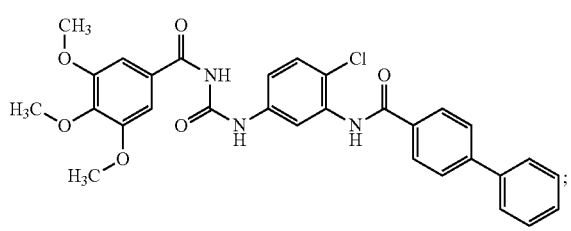

N-[[[3-(benzoylamino)phenyl]amino]thioxomethyl]-3,4,5-methoxy-benzamide (I-a) with the following formula:

(compound 38)

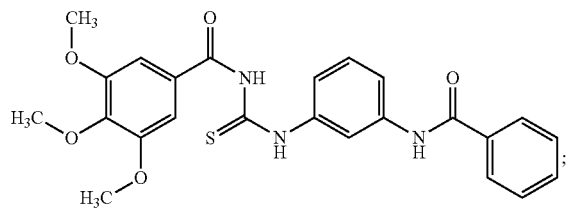

N-[[[4-chloro-3-(4-dimethylamino-phenylamino)carbonyl] thioxomethyl]-3,4,5-methoxy-benzamide (I-b) with the following formula:

(compound 39)

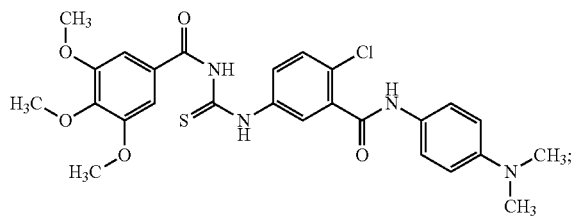

N-[[[4-chloro-3-(4-methoxy-phenylamino)carbonyl]thioxomethyl]-3,4,5-methoxy-benzamide (I-b) with the following formula:

(compound 40)

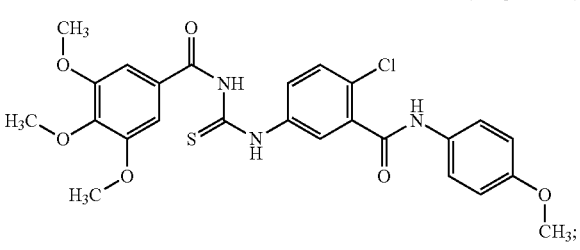

N-[[[5-bromo-3-(phenylamino)carbonyl]thioxomethyl]-3,4,5-methoxy-benzamide (I-b) with the following formula:

(compound 41)

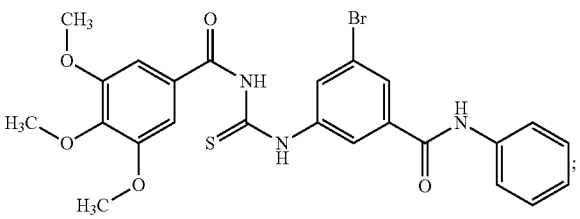

N-[[[4-chloro-3-(4-methoxy-phenylamino)carbonyl]oxomethyl]-3,4,5-methoxy-benzamide (I-b') with the following formula:

(compound 42)

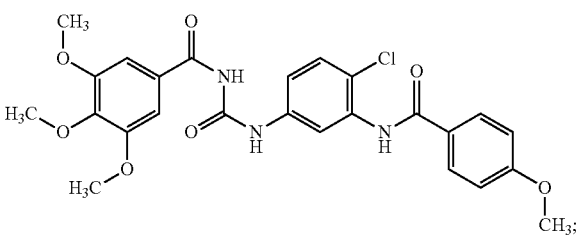

N-[[[4-chloro-3-(4-chloro-phenylamino)]carbonyl]phenylamino]thioxomethyl]-3,4,5-methoxy-benzamide (I-b) with the following formula:

(compound 43)

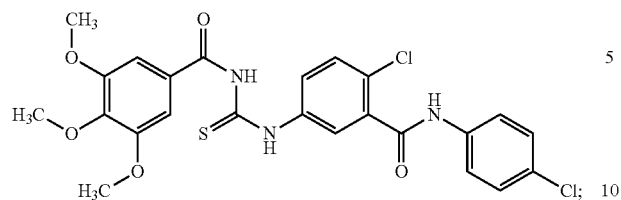

N-[[[4-chloro-3-(phenylamino)carbonyl]oxomethyl]-3,4,5-methoxy-benzamide (I-b') with the following formula:

(compound 44)

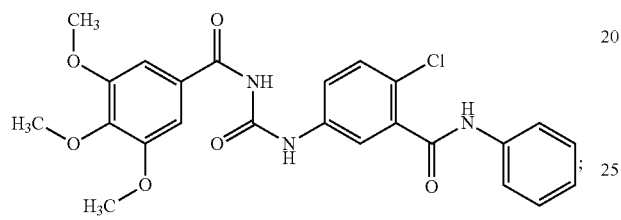

N-[[[2-methyl-3-(benzoylamino)phenyl]amino]oxomethyl]-3,4,5-methoxy-benzamide (I-a') with the following formula:

(compound 45)

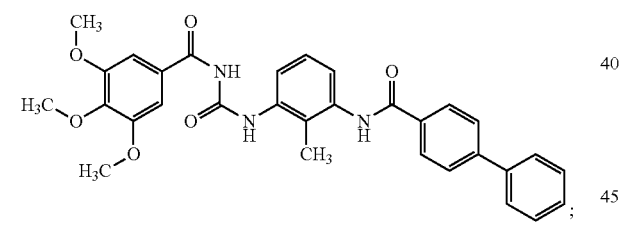

N-[[[2-methyl-3-(benzoylamino)phenyl]amino]thioxomethyl]-3,4,5-methoxy-benzamide (I-a) with the following formula:

(compound 46)

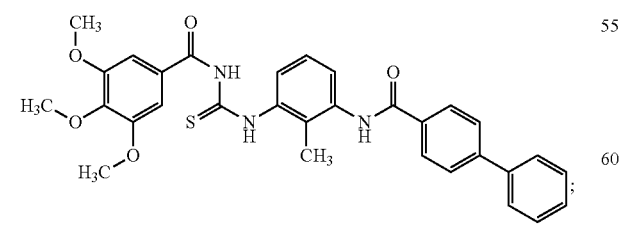

N-[[[-3-(4-chloro-benzoylamino)phenyl]amino]oxomethyl]-3,4,5-methoxy-benzamide (I-a') with the following formula:

(compound 47)

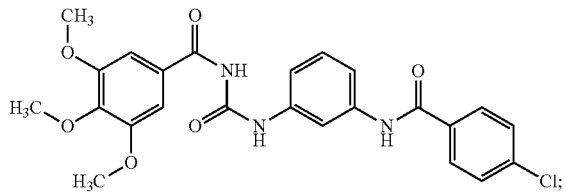

N-[[[-3-(benzoylamino)phenyl]amino]oxomethyl]-2,4,5-methoxy-benzamide (I-a') with the following formula:

(compound 48)

N-[[[-3-(benzoylamino)phenyl]amino]oxomethyl]-4-methoxy-benzamide (I-a') with the following formula:

(compound 49)

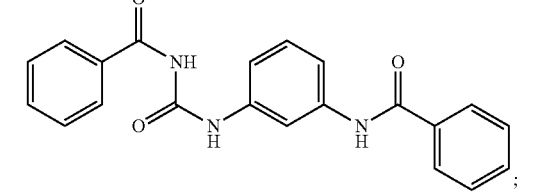

N-[[[-3-(benzoylamino)phenyl]amino]oxomethyl]-benzamide (I-a') with the following formula:

(compound 50)

N-(3-(1H-indol-2-yl)phenylcarbamoyl)-3,4,5-trimethoxybenzamide (I-d') with formula.

5. The method as claimed in claim 2, characterized in that the compounds with formula (I) are selected from the group consisting of:
N-[[[3-(4-methoxy-benzoylamino)phenyl]amino]thioxomethyl]-3,4,5-methoxy-benzamide (compound 1);
N-[[[3-(2-chloro-benzoylamino)phenyl]amino]thioxomethyl]-3,4,5-methoxy-benzamide (compound 2);
N-[[[3-(3-methoxy-benzoylamino)phenyl]amino]thioxomethyl]-3,4,5-methoxy-benzamide (compound 3);

N-[[[3-(2-methoxy-benzoylamino)phenyl]amino]thioxomethyl]-3,4,5-methoxy-benzamide (compound 4);
N-[[[3-(4-methoxy-benzoylamino)phenyl]amino]oxomethyl]-3,4,5-methoxy-benzamide (compound 6);
N-[[[3-(4-pyridocarboxylamino)phenyl]amino]thioxomethyl]-3,4,5-methoxy-benzamide (compound 11);
N-[[[3-(4-chloro-benzoylamino)phenyl]amino]thioxomethyl]-3,4,5-methoxy-benzamide (compound 13);
N-[[[3-(isopropoylcarboxylamino))phenyl]amino]oxomethyl]-3,4,5-methoxy-benzamide (compound 17);
N-[[[3-(benzoylamino)phenyl]amino]thioxomethyl]-3,5-methoxy-benzamide (compound 18);
N-[[[3-(benzoylamino)phenyl]amino]thioxomethyl]-3,5-methoxy-4-ethoxy-benzamide (compound 19);
N-[[[3-(benzoylamino)phenyl]amino]thioxomethyl]-3,4-ethoxy-5-methoxy-benzamide (compound 20);
N-[[[3-(benzoylamino)phenyl]amino]thioxomethyl]-3,4,5-ethoxy-benzamide (compound 23);
N-[[[4-fluoro-3-(benzoylamino)phenyl]amino]thioxomethyl]-3,4,5-methoxy-benzamide (compound 24);
N-[[[4-chloro-3-(phenylamino)carbonyl]amino]thioxomethyl]-3,4,5-methoxy-benzamide (compound 25);
N-[[[3-(benzoylamino)phenyl]amino]oxomethyl]-3,4,5-methoxy-benzamide (compound 31);
N-[[[4-chloro-3-(benzoylamino)phenyl]amino]thioxomethyl]-3,4,5-methoxy-benzamide (compound 34);
N-[[[3-(benzoylamino)phenyl]amino]thioxomethyl]-3,4,5-methoxy-benzamide (compound 38);
N-[[[4-chloro-3-(4-dimethylamino-phenylamino)carbonyl]thioxomethyl]-3,4,5-methoxy-benzamide (compound 39);
N-[[[4-chloro-3-(4-chloro-phenylamino)]carbonyl]phenylamino]thioxomethyl]-3,4,5-methoxy-benzamide (compound 43);
N-[[[2-methyl-3-(benzoylamino)phenyl]amino]oxomethyl]-3,4,5-methoxy-benzamide (compound 45);
N-[[[-3-(4-chloro-benzoylamino)phenyl]amino]oxomethyl]-3,4,5-methoxy-benzamide (compound 47).

6. The method as claimed in claim 1, characterized in that the drug is for treating tumors characterized by a hyperactivation of Hedgehog protein signaling pathway.

7. The method as claimed in claim 1, characterized in that the drug is for treating neuro-degenerative type pathology characterized by a hyperactivation of Hedgehog protein signaling pathway.

8. Compounds with the following formula (I'):

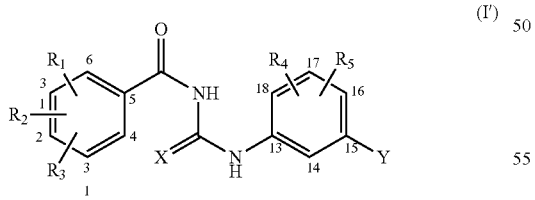

(I')

wherein:
R$_1$, R$_2$ and R$_3$, which are identical or different and independent of each other, represent a hydrogen or a halogen atom, a hydroxyl radical, an alkyl, perfluoroalkyl, alkoxy, alkylthio or nitrile group, a substituted alkoxy group;
X represents a sulfur or oxygen atom;
Y represents a a —NH—(C=O)—R$_6$ group, wherein R$_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;
R$_4$ and R$_5$, which are identical or different and independent of each other, represent a hydrogen or a halogen atom, or an alkoxy, alkylthio, alkyl, perfluoroalkyl, nitrile or nitro group;
it being understood that when Y represents a —NH—(C=O)—R$_6$ group, X represents a sulfur atom.

9. The compounds as claimed in claim 8, characterized in that they are selected from the group consisting of:
N-[[[3-(4-methoxy-benzoylamino)phenyl]amino]thioxomethyl]-3,4,5-methoxy-benzamide (I-a) with the following formula:

(compound 1)

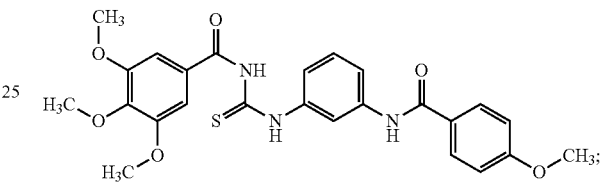

N-[[[3-(2-chloro-benzoylamino)phenyl]amino]thioxomethyl]-3,4,5-methoxy-benzamide (I-a) with the following formula:

(compound 2)

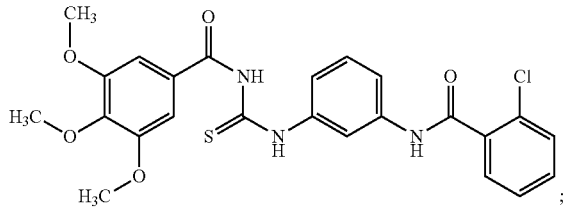

N-[[[3-(3-methoxy-benzoylamino)phenyl]amino]thioxomethyl]-3,4,5-methoxy-benzamide (I-a) with the following formula:

(compound 3)

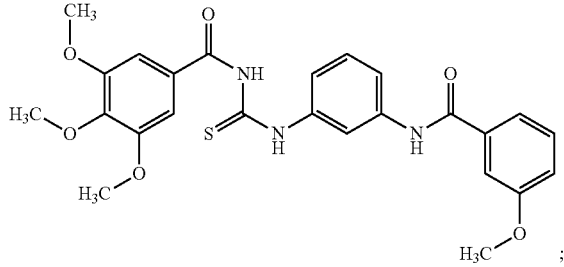

N-[[[3-(2-methoxy-benzoylamino)phenyl]amino]thioxomethyl]-3,4,5-methoxy-benzamide (I-a) with the following formula:

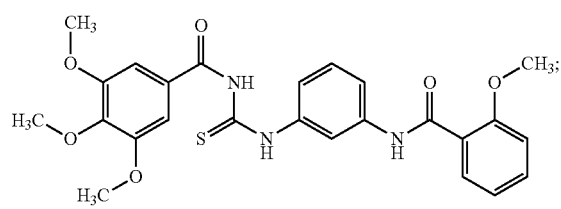

(compound 4)

N-[[[3-(4-phenyl-benzoylamino)phenyl]amino]thioxom-ethyl]-3,4,5-methoxy-benzamide (I-a) with the following formula:

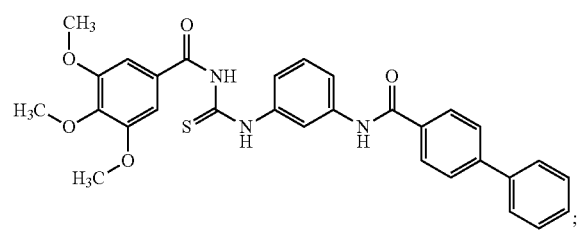

(compound 5)

N-[[[3-(-cyclohexylcarboxylamino)phenyl]amino]thiox-omethyl]-3,4,5-methoxy-benzamide (I-a) with the following formula:

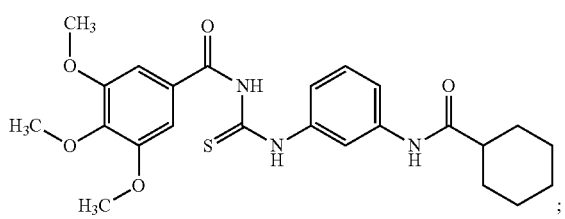

(compound 8)

N-[[[3-(2-naphthoylamino)phenyl]amino]thioxomethyl]-3,4,5-methoxy-benzamide (I-a) with the following formula:

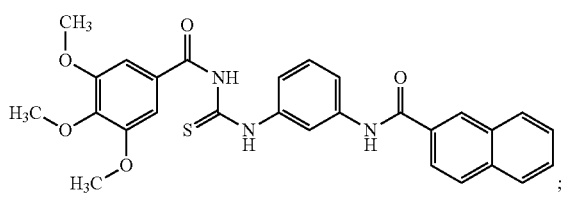

(compound 9)

N-[[[3-(isopropoylcarboxylamino)phenyl]amino]thiox-omethyl]-3,4,5-methoxy-benzamide (I-a) with the following formula:

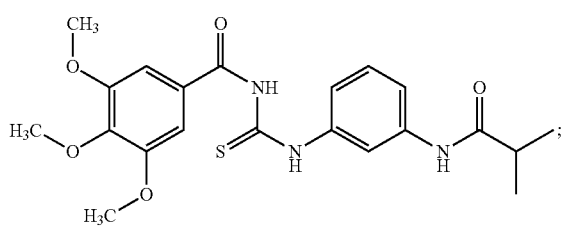

(compound 10)

N-[[[3-(4-pyridocarboxylamino)phenyl]amino]thioxom-ethyl]-3,4,5-methoxy-benzamide (I-a) with the following formula:

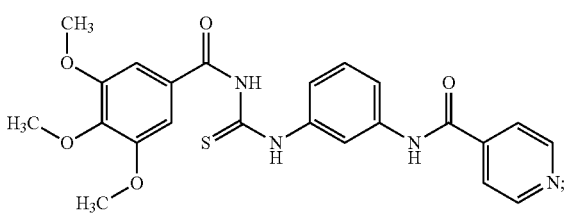

(compound 11)

N-[[[3-(1-naphthoylamino)phenyl]amino]thioxomethyl]-3,4,5-methoxy-benzamide (I-a) with the following formula:

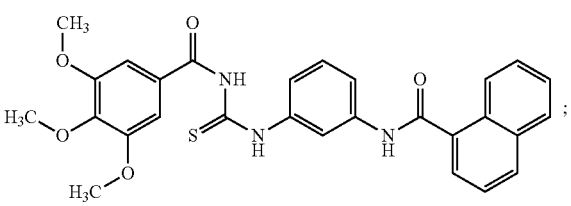

(compound 12)

N-[[[3-(4-chloro-benzoylamino)phenyl]amino]thioxom-ethyl]-3,4,5-methoxy-benzamide (I-a) with the following formula:

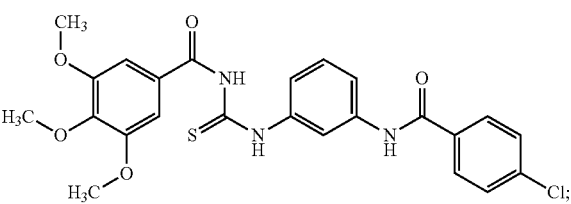

(compound 13)

N-[[[3-(2-furoylamino)phenyl]amino]thioxomethyl]-3,4,5-methoxy-benzamide (I-a) with the following formula:

(compound 14)

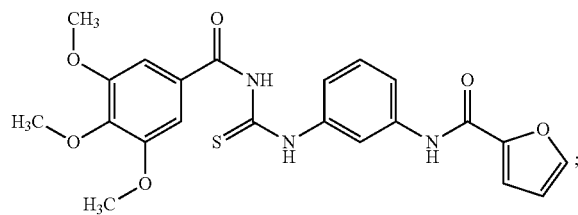

N-[[[3-(2-thiophenoylamino)phenyl]amino]thioxomethyl]-3,4,5-methoxy-benzamide (I-a) with the following formula:

(compound 15)

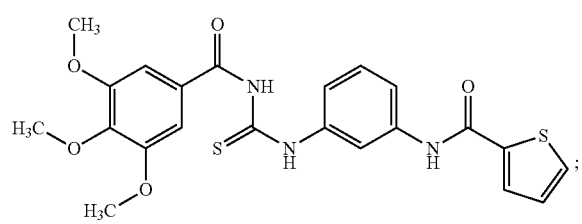

N-[[[3-(benzoylamino)phenyl]amino]thioxomethyl]-3,5-methoxy-benzamide (I-a) with the following formula:

(compound 18)

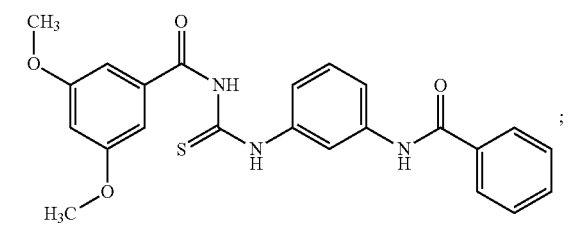

N-[[[3-(benzoylamino)phenyl]amino]thioxomethyl]-3,5-methoxy-4-ethoxy-benzamide (I-a) with the following formula:

(compound 19)

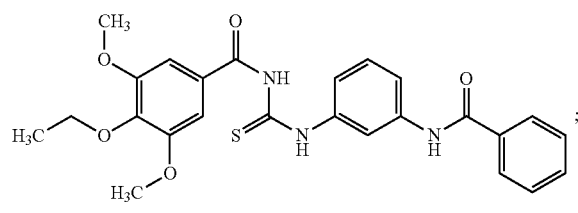

N-[[[3-(benzoylamino)phenyl]amino]thioxomethyl]-3,4-ethoxy-5-methoxy-benzamide (I-a) with the following formula:

(compound 20)

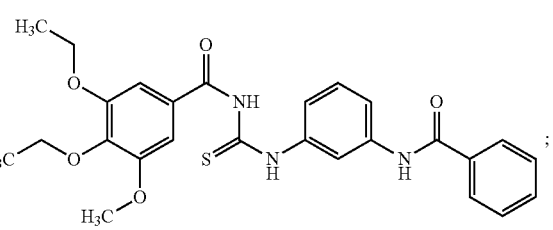

N-[[[3-(benzoylamino)phenyl]amino]thioxomethyl]-2,4-methoxy-benzamide (I-a) with the following formula:

(compound 22)

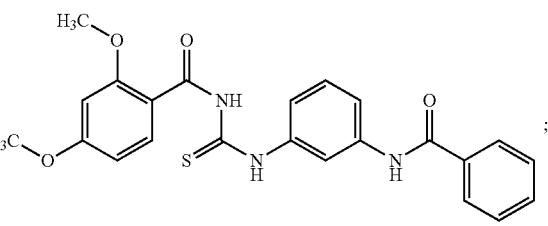

N-[[[3-(benzoylamino)phenyl]amino]thioxomethyl]-3,4,5-ethoxy-benzamide (I-a) with the following formula:

(compound 23)

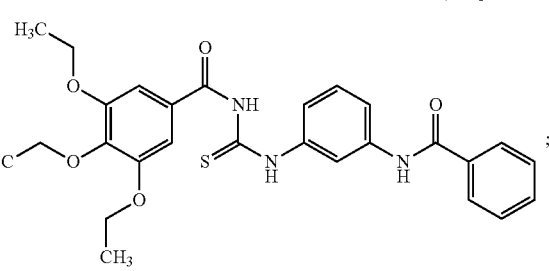

N-[[[4-fluoro-3-(benzoylamino)phenyl]amino]thioxomethyl]-3,4,5-methoxy-benzamide (I-a) with the following formula:

(compound 24)

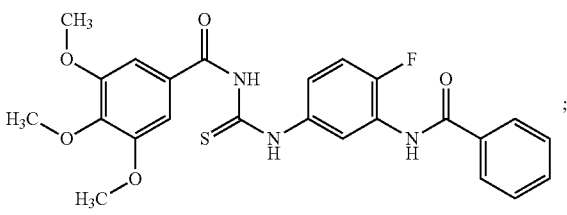

N-[[[4-methoxy-3-(benzoylamino)phenyl]amino]thioxomethyl]-3,4,5-methoxy-benzamide (I-a) with the following formula:

(compound 26)

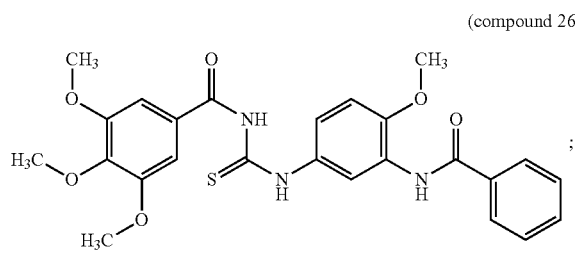

N-[[[4-methyl-3-(benzoylamino)phenyl]amino]thioxomethyl]-3,4,5-methoxy-benzamide (I-a) with the following formula:

(compound 27)

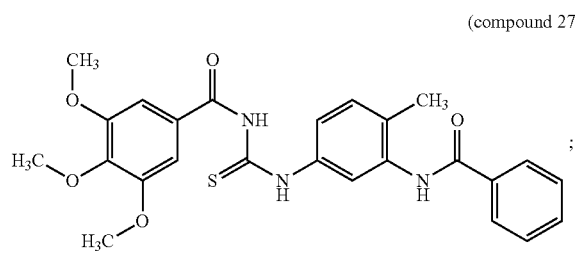

N-[[[3-methyl-3-(benzoylamino)phenyl]amino]thioxomethyl]-3,4,5-methoxy-benzamide (I-a) with the following formula:

(compound 32)

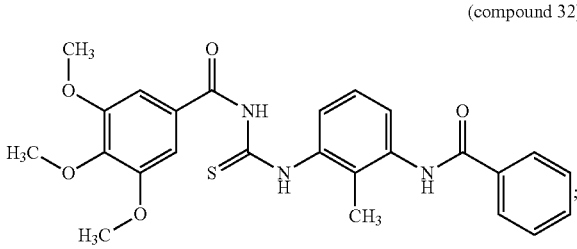 [SMILES: COc1cc(C(=O)NC(=S)Nc2cccc(NC(=O)c3ccccc3)c2C)cc(OC)c1OC]

N-[[[4-chloro-3-(benzoylamino)phenyl]amino]thioxomethyl]-3,4,5-methoxy-benzamide (I-a) with the following formula:

(compound 34)

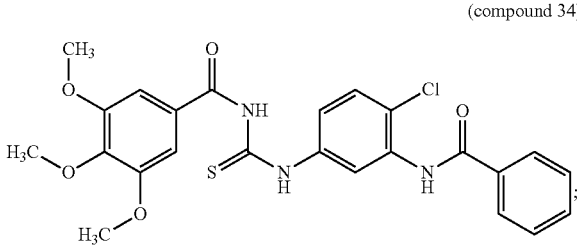

N-[[[5-chloro-3-(benzoylamino)phenyl]amino]thioxomethyl]-3,4,5-methoxy-benzamide (I-a) with the following formula:

(compound 35)

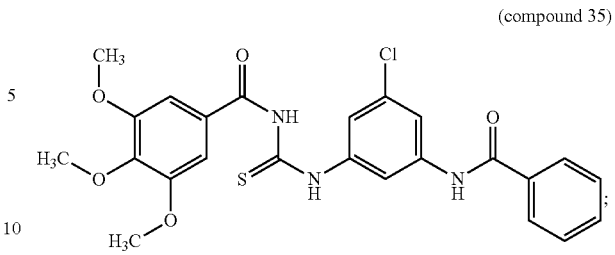

N-[[[5-fluoro-3-(benzoylamino)phenyl]amino]thioxomethyl]-3,4,5-methoxy-benzamide (I-a) with the following formula:

(compound 36)

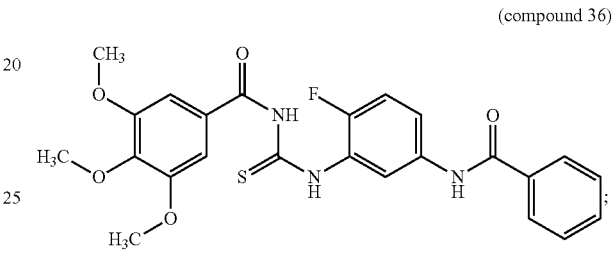

N-[[[3-(benzoylamino)phenyl]amino]thioxomethyl]-3,4,5-methoxy-benzamide (I-a) with the following formula:

(compound 38)

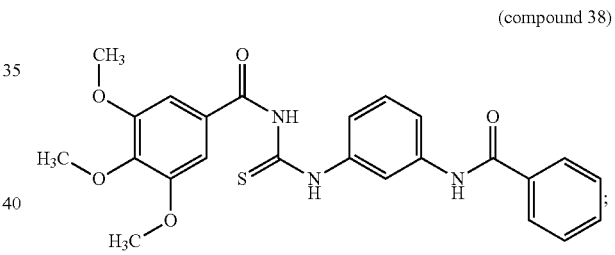

N-[[[2-methyl-3-(benzoylamino)phenyl]amino]thioxomethyl]-3,4,5-methoxy-benzamide (I-a) with the following formula:

(compound 46)

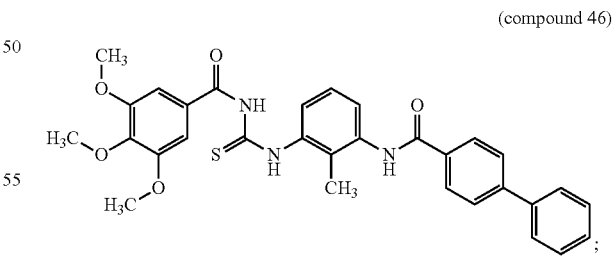

N-(3-(1H-indol-2-yl)phenylcarbamoyl)-3,4,5-trimethoxybenzamide (I-d') with formula.

10. The compounds as claimed in claim 8, characterized in that they are selected from the group consisting of:
N-[[[3-(4-methoxy-benzoylamino)phenyl]amino]thioxomethyl]-3,4,5-methoxy-benzamide (compound 1);
N-[[[3-(2-chloro-benzoylamino)phenyl]amino]thioxomethyl]-3,4,5-methoxy-benzamide (compound 2);

N-[[[3-(3-methoxy-benzoylamino)phenyl]amino]thioxomethyl]-3,4,5-methoxy-benzamide (compound 3);
N-[[[3-(2-methoxy-benzoylamino)phenyl]amino]thioxomethyl]-3,4,5-methoxy-benzamide (compound 4);
N-[[[3-(4-pyridocarboxylamino)phenyl]amino]thioxomethyl]-3,4,5-methoxy-benzamide (compound 11);
N-[[[3-(4-chloro-benzoylamino)phenyl]amino]thioxomethyl]-3,4,5-methoxy-benzamide (compound 13);
N-[[[3-(benzoylamino)phenyl]amino]thioxomethyl]-3,5-methoxy-benzamide (compound 18);
N-[[[3-(benzoylamino)phenyl]amino]thioxomethyl]-3,5-methoxy-4-ethoxy-benzamide (compound 19);
N-[[[3-(benzoylamino)phenyl]amino]thioxomethyl]-3,4-ethoxy-5-methoxy-benzamide (compound 20);
N-[[[3-(benzoylamino)phenyl]amino]thioxomethyl]-3,4,5-ethoxy-benzamide (compound 23);
N-[[[4-fluoro-3-(benzoylamino)phenyl]amino]thioxomethyl]-3,4,5-methoxy-benzamide (compound 24);
N-[[[4-chloro-3-(benzoylamino)phenyl]amino]thioxomethyl]-3,4,5-methoxy-benzamide (compound 34);
N-[R3-(benzoylamino)phenyl]amino]thioxomethyl]-3,4,5-methoxy-benzamide (compound 38).

11. A pharmaceutical composition, characterized in that it comprises, as active principle, at least one compound as defined in claim 8, and at least one pharmaceutically acceptable excipient.

12. A method for treating tumors characterized by a hyperactivation of Hedgehog protein signaling pathway or neurodegenerative type pathologies characterized by a hyperactivation of Hedgehog protein signaling pathway, comprising a step of administering at least one compound of formula (I):

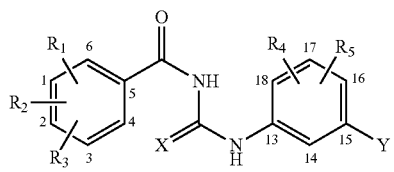
(I)

wherein:
$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, or a substituted alkoxy group;
X represents a sulfur or oxygen atom;
Y represents a —NH—(C═O)—$R_6$ or —(C═O)—NH—$R_6$ group, wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;
$R_4$ and $R_5$, which are identical or different and independent of each other, represent a hydrogen or a halogen atom, or an alkoxy, alkylthio, alkyl, perfluoroalkyl, nitrile or nitro group, to a patient in need thereof.

13. A method for treating tumors characterized by a hyperactivation of Hedgehog protein signaling pathway or neurodegenerative type pathologies characterized by a hyperactivation of Hedgehog protein signaling pathway, comprising a step of administering at least one compound of formula (I):

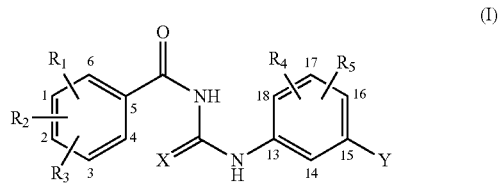
(I)

wherein:
$R_1$, $R_2$ and $R_3$, which are identical or different and independent of each other, represent a hydrogen or a halogen atom, a hydroxyl radical, an alkyl, perfluoroalkyl, alkoxy, alkylthio or nitrile group, or a substituted alkoxy group;
X represents a sulfur or oxygen atom;
Y represents a —NH—(C═O)—$R_6$ or —(C═O)—NH—$R_6$ group, wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group;
$R_4$ and $R_5$, which are identical or different and independent of each other, represent a hydrogen or a halogen atom, or an alkoxy, alkylthio, alkyl, perfluoroalkyl or nitrile group;
it being understood that when Y represents a group —NH—(C═O)—$R_6$:
$R_4$ and/or $R_5$ can also represent a nitro group, to a patient in need thereof.

14. The method of claim 12, wherein the compounds are selected from those in which, in the formula (I):
$R_1$, $R_2$, and $R_3$, which are identical or different, represent a hydrogen atom or a methyloxy or ethyloxy radical,
X represents a sulfur or oxygen atom;
Y represents or a —NH—(C═O)—$R_6$ or —(C═O)—NH—$R_6$ group wherein $R_6$ represents a group selected from phenyl groups; phenyl substituted with a radical methoxy or dimethylamino, with a chlorine atom, with a phenyl group, with a benzyl, cyclohexyl, isopropyl, pyridinyl, naphthyl, furfuryl or thiophene group; and
$R_4$ and $R_5$, which are identical or different, are selected from hydrogen, chlorine, bromine, fluorine, methyl and methoxy.

15. The method of claim 12, wherein the compounds with formula (I) are selected from the group consisting of:
N-[[[3-(4-methoxy-benzoylamino)phenyl]amino]thioxomethyl]-3,4,5-methoxy-benzamide (I-a) with the following formula:

(compound 1)

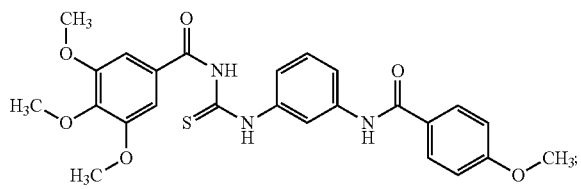

N-[[[3-(2-chloro-benzoylamino)phenyl]amino]thioxomethyl]-3,4,5-methoxy-benzamide (I-a) with the following formula:

(compound 2)

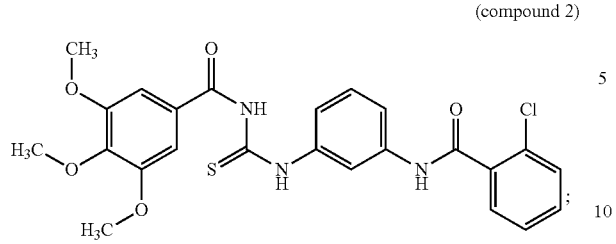

N-[[[3-(3-methoxy-benzoylamino)phenyl]amino]thioxomethyl]-3,4,5-methoxy-benzamide (I-a) with the following formula:

(compound 3)

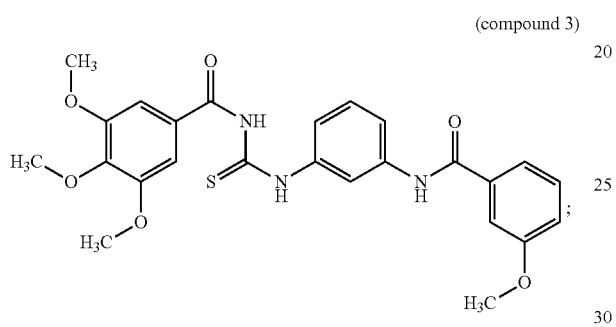

N-[[[3-(2-methoxy-benzoylamino)phenyl]amino]thioxomethyl]-3,4,5-methoxy-benzamide (I-a) with the following formula:

(compound 4)

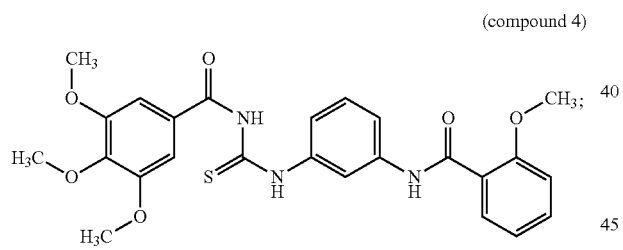

N-[[[3-(4-phenyl-benzoylamino)phenyl]amino]thioxomethyl]-3,4,5-methoxy-benzamide (I-a) with the following formula:

(compound 5)

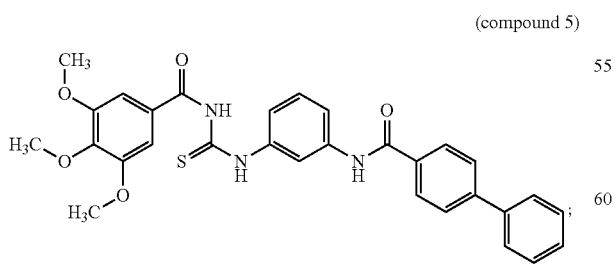

N-[[[3-(4-methoxy-benzoylamino)phenyl]amino]oxomethyl]-3,4,5-methoxy-benzamide (I-a') with the following formula:

(compound 6)

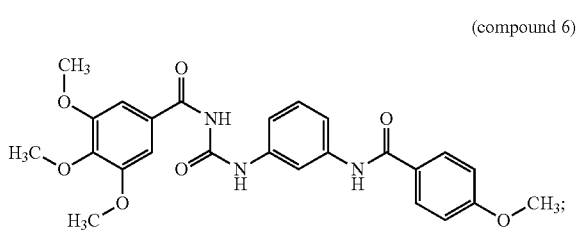 [SMILES: COc1ccc(C(=O)Nc2cccc(NC(=O)NC(=O)c3cc(OC)c(OC)c(OC)c3)c2)cc1]

N-[[[3-(4-phenyl-benzoylamino)phenyl]amino]oxomethyl]-3,4,5-methoxy-benzamide (I-a') with the following formula:

(compound 7)

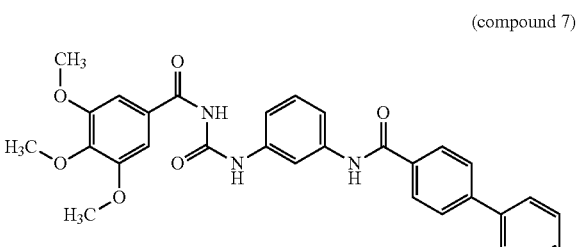

N-[[[3-(-cyclohexylcarboxylamino)phenyl]amino]thioxomethyl]-3,4,5-methoxy-benzamide (I-a) with the following formula:

(compound 8)

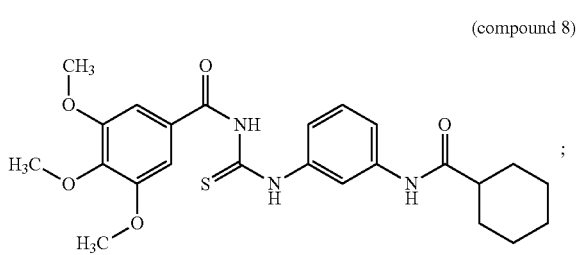 [SMILES: COc1cc(C(=O)NC(=S)Nc2cccc(NC(=O)C3CCCCC3)c2)cc(OC)c1OC]

N-[[[3-(2-naphthoylamino)phenyl]amino]thioxomethyl]-3,4,5-methoxy-benzamide (I-a) with the following formula:

(compound 9)

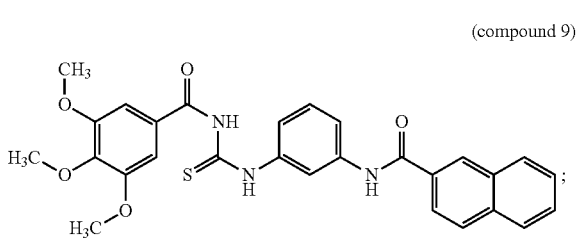 [SMILES: COc1cc(C(=O)NC(=S)Nc2cccc(NC(=O)c3ccc4ccccc4c3)c2)cc(OC)c1OC]

N-[[[3-(isopropoylcarboxylamino)phenyl]amino]thioxomethyl]-3,4,5-methoxy-benzamide (I-a) with the following formula:

(compound 10)

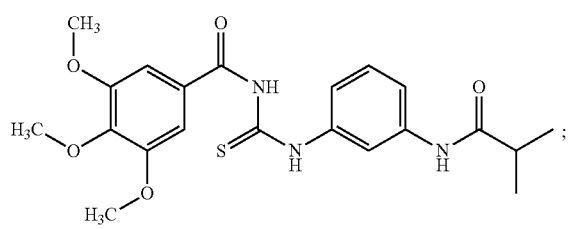

N-[[[3-(4-pyridocarboxylamino)phenyl]amino]thioxomethyl]-3,4,5-methoxy-benzamide (I-a) with the following formula:

(compound 11)

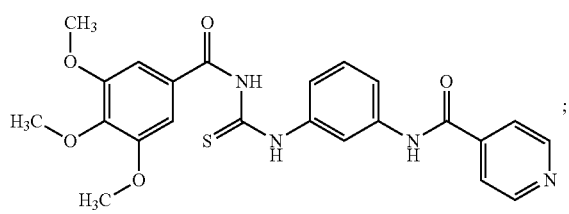

N-[[[3-(1-naphthoylamino)phenyl]amino]thioxomethyl]-3,4,5-methoxy-benzamide (I-a) with the following formula:

(compound 12)

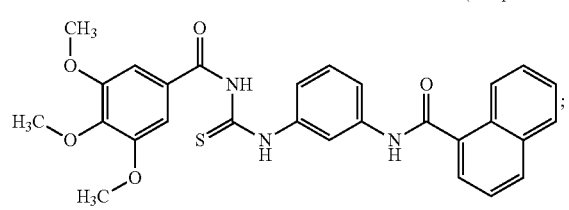

N-[[[3-(4-chloro-benzoylamino)phenyl]amino]thioxomethyl]-3,4,5-methoxy-benzamide (I-a) with the following formula:

(compound 13)

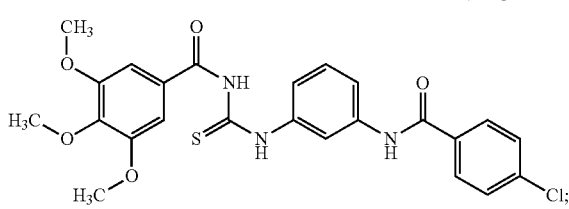

N-[[[3-(2-furoylamino)phenyl]amino]thioxomethyl]-3,4,5-methoxy-benzamide (I-a) with the following formula:

(compound 14)

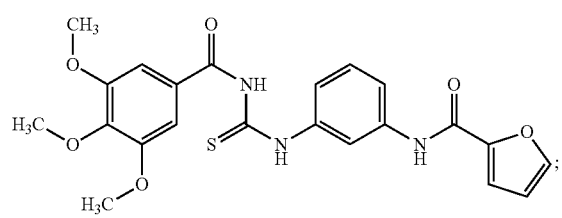

N-[[[3-(2-thiophenoylamino)phenyl]amino]thioxomethyl]-3,4,5-methoxy-benzamide (I-a) with the following formula:

(compound 15)

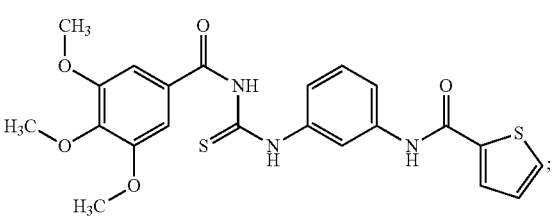

N-[[[3-(2-naphthoylamino)phenyl]amino]oxomethyl]-3,4,5-methoxy-benzamide (I-a') with the following formula:

(compound 16)

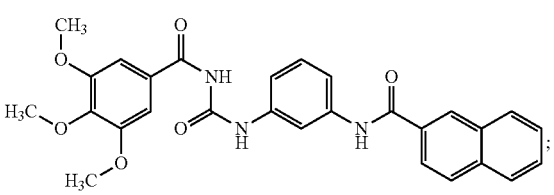

N-[[[3-(isopropoylcarboxylamino))phenyl]amino]oxomethyl]-3,4,5-methoxy-benzamide (I-a') with the following formula:

(compound 17)

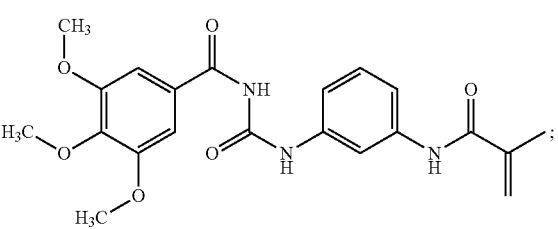

N-[[[3-(benzoylamino)phenyl]amino]thioxomethyl]-3,5-methoxy-benzamide (I-a) with the following formula:

(compound 18)

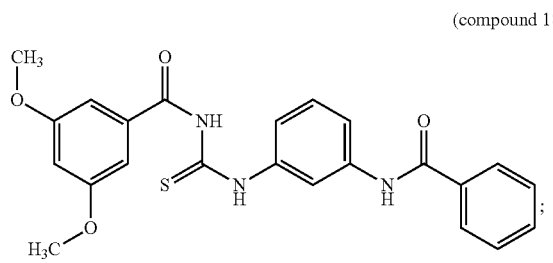

N-[[[3-(benzoylamino)phenyl]amino]thioxomethyl]-3,5-methoxy-4-ethoxy-benzamide (I-a) with the following formula:

(compound 19)

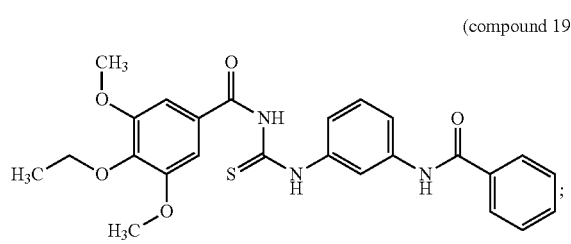

N-[[[3-(benzoylamino)phenyl]amino]thioxomethyl]-3,4-ethoxy-5-methoxy-benzamide (I-a) with the following formula:

(compound 20)

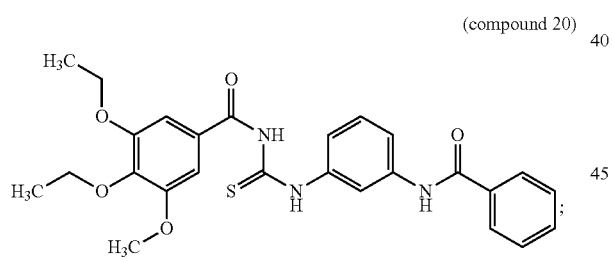

N-[[3-(benzoylamino)phenyl]amino]thioxomethyl]-2,4-methoxy-benzamide (I-a) with the following formula:

(compound 22)

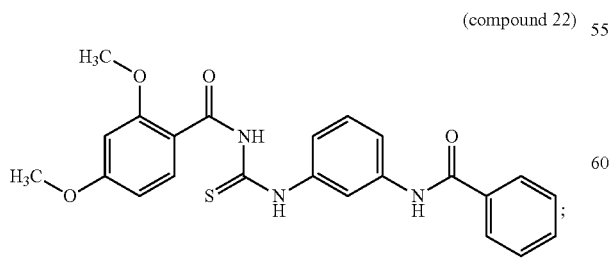

N-[[[3-(benzoylamino)phenyl]amino]thioxomethyl]-3,4,5-ethoxy-benzamide (I-a) with the following formula:

(compound 23)

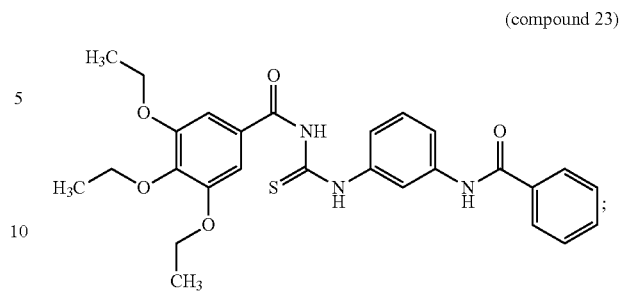

N-[[[4-fluoro-3-(benzoylamino)phenyl]amino]thioxomethyl]-3,4,5-methoxy-benzamide (I-a) with the following formula:

(compound 24)

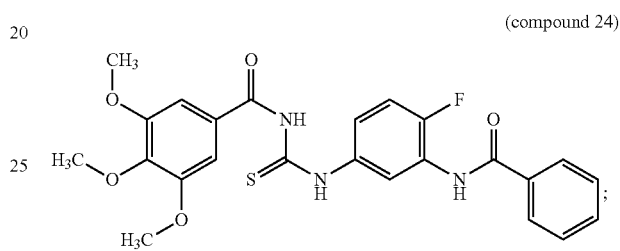

N-[[[4-chloro-3-(phenylamino)carbonyl]amino]thioxomethyl]-3,4,5-methoxy-benzamide (I-b) with the following formula:

(compound 25)

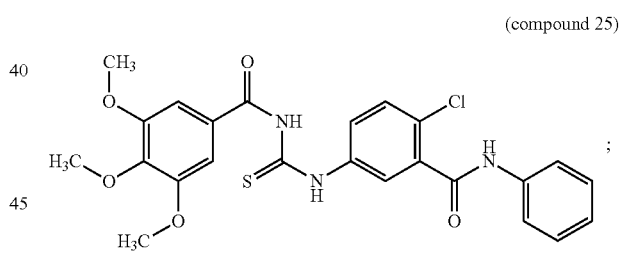

N-[[[4-methoxy-3-(benzoylamino)phenyl]amino]thioxomethyl]-3,4,5-methoxy-benzamide (I-a) with the following formula:

(compound 26)

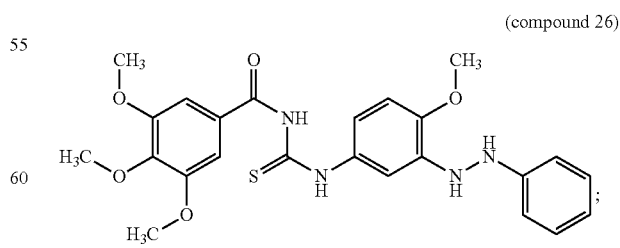

N-[[[4-methyl-3-(benzoylamino)phenyl]amino]thioxomethyl]-3,4,5-methoxy-benzamide (I-a) with the following formula:

(compound 27)

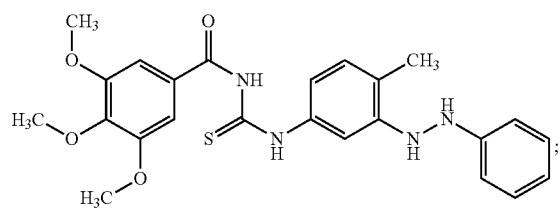

N-[[[3-(benzoylamino)phenyl]amino]oxomethyl]-3,4,5-ethoxy-benzamide (I-a') with the following formula:

(compound 29)

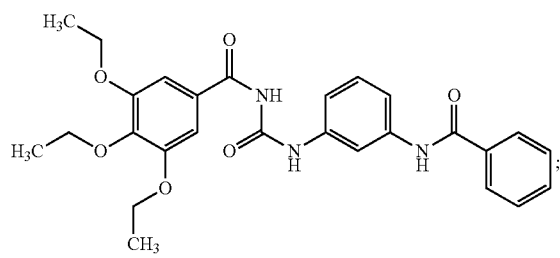

N-[[[3-(benzoylamino)phenyl]amino]oxomethyl]-3,4,5-methoxy-benzamide (I-a') with the following formula:

(compound 31)

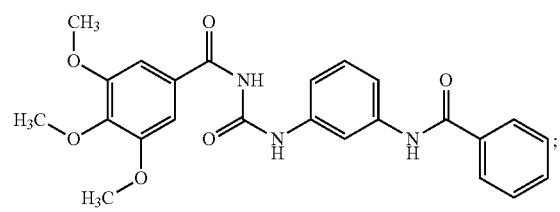

N-[[[3-methyl-3-(benzoylamino)phenyl]amino]thioxomethyl]-3,4,5-methoxy-benzamide (I-a) with the following formula:

(compound 32)

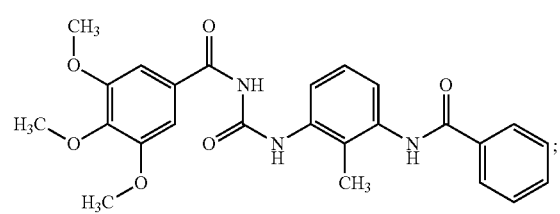

N-[[[4-chloro-3-(benzoylamino)phenyl]amino]oxomethyl]-3,4,5-methoxy-benzamide (I-a') with the following formula:

(compound 33)

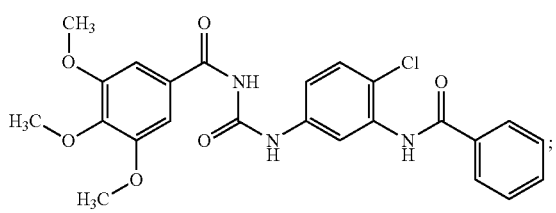

N-[[[4-chloro-3-(benzoylamino)phenyl]amino]thioxomethyl]-3,4,5-methoxy-benzamide (I-a) with the following formula:

(compound 34)

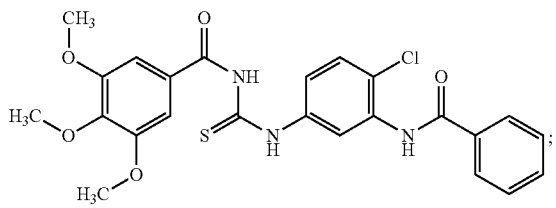

N-[[[5-chloro-3-(benzoylamino)phenyl]amino]thioxomethyl]-3,4,5-methoxy-benzamide (I-a) with the following formula:

(compound 35)

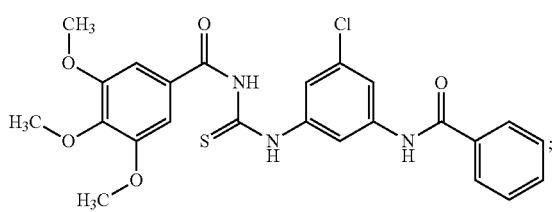

N-[[[5-fluoro-3-(benzoylamino)phenyl]amino]thioxomethyl]-3,4,5-methoxy-benzamide (I-a) with the following formula:

(compound 36)

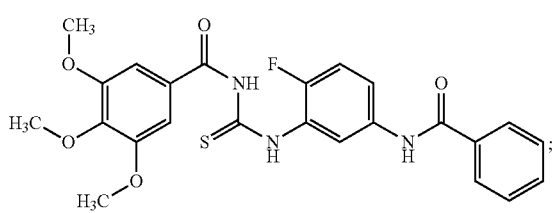

N-[[[4-chloro-3-(4-Phenyl-benzoylamino)phenyl]amino]oxomethyl]-3,4,5-methoxy-benzamide (I-a') with the following formula:

(compound 37)

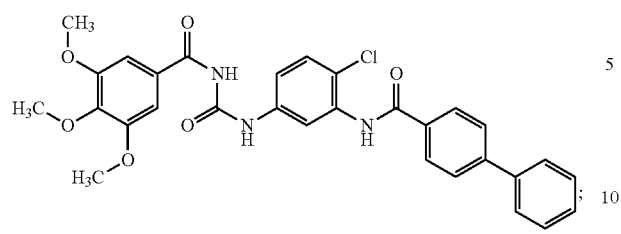

N-[[[3-(benzoylamino)phenyl]amino]thioxomethyl]-3,4,5-methoxy-benzamide (I-a) with the following formula:

(compound 38)

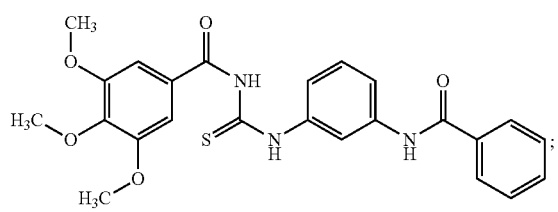

N-[[[4-chloro-3-(4-dimethylamino-phenylamino)carbonyl]thioxomethyl]-3,4,5-methoxy-benzamide (I-b) with the following formula:

(compound 39)

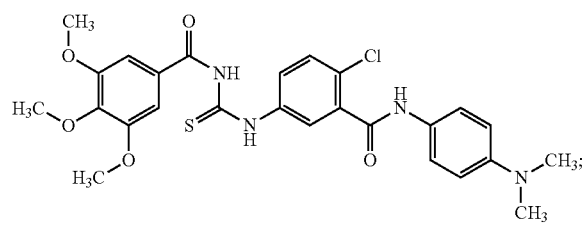

N-[[[4-chloro-3-(4-methoxy-phenylamino)carbonyl]thioxomethyl]-3,4,5-methoxy-benzamide (I-b) with the following formula:

(compound 40)

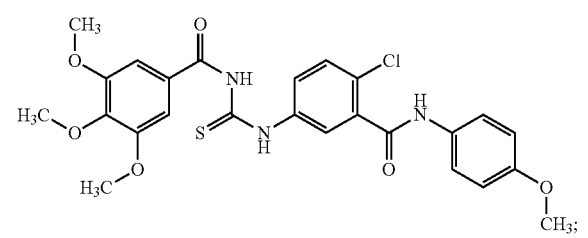

N-[[[5-bromo-3-(phenylamino)carbonyl]thioxomethyl]-3,4,5-methoxy-benzamide (I-b) with the following formula:

(compound 41)

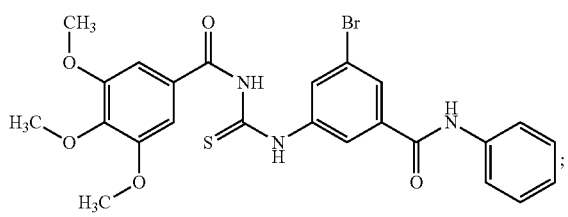

N-[[[4-chloro-3-(4-methoxy-phenylamino)carbonyl]oxomethyl]-3,4,5-methoxy-benzamide (I-b') with the following formula:

(compound 42)

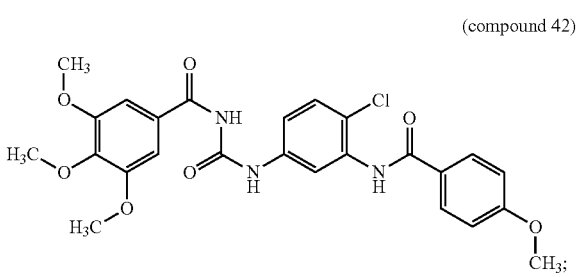 [SMILES: COc1ccc(C(=O)Nc2cc(NC(=O)NC(=O)c3cc(OC)c(OC)c(OC)c3)ccc2Cl)cc1]

N-[[[4-chloro-3-(4-chloro-phenylamino)]carbonyl]phenylamino]thioxomethyl]-3,4,5-methoxy-benzamide (I-b) with the following formula:

(compound 43)

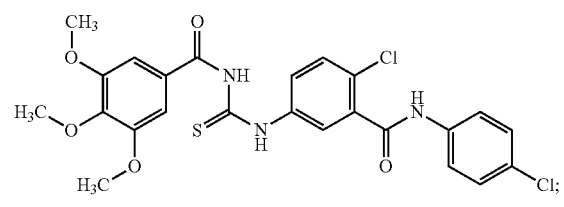

N-[[[4-chloro-3-(phenylamino)carbonyl]oxomethyl]-3,4,5-methoxy-benzamide (I-b') with the following formula:

(compound 44)

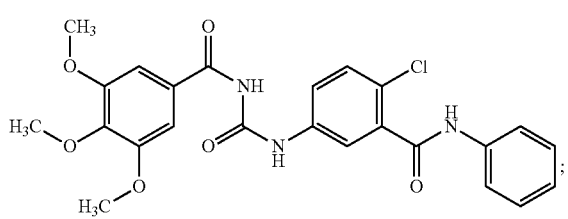

N-[[[2-methyl-3-(benzoylamino)phenyl]amino]oxomethyl]-3,4,5-methoxy-benzamide (I-a') with the following formula:

(compound 45)

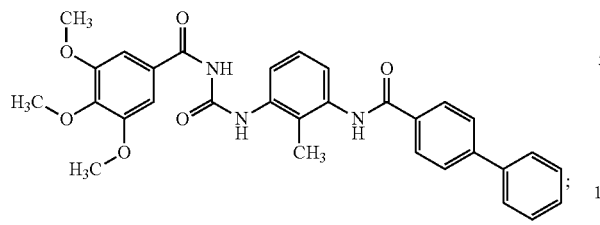

N-[[[2-methyl-3-(benzoylamino)phenyl]amino]thioxomethyl]-3,4,5-methoxy-benzamide (I-a) with the following formula:

(compound 46)

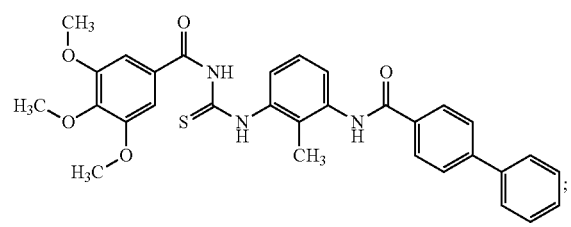

N-[[[-3-(4-chloro-benzoylamino)phenyl]amino]oxomethyl]-3,4,5-methoxy-benzamide (I-a') with the following formula:

(compound 47)

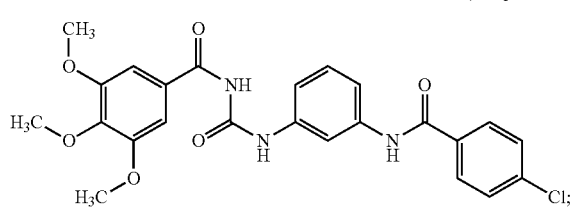

N-[[[-3-(benzoylamino)phenyl]amino]oxomethyl]-2,4,5-methoxy-benzamide (I-a') with the following formula:

(compound 48)

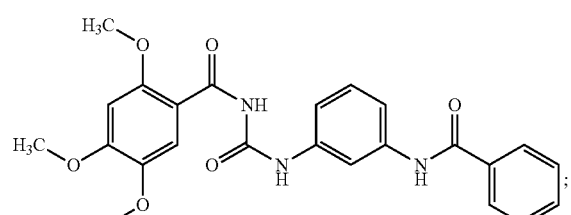

N-[[[-3-(benzoylamino)phenyl]amino]oxomethyl]-4-methoxy-benzamide (I-a') with the following formula:

(compound 49)

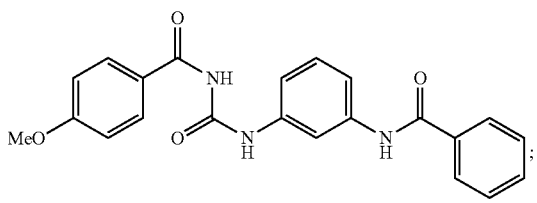

N-[[[-3-(benzoylamino)phenyl]amino]oxomethyl]benzamide (I-a') with the following formula:

(compound 50)

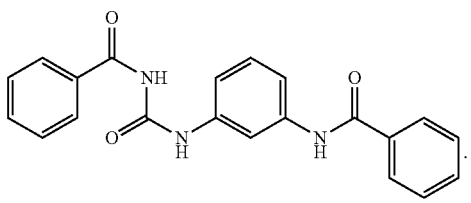

16. The method of claim 12, wherein the compounds with formula (I) are selected from the group consisting of:
N-[[[3-(4-methoxy-benzoylamino)phenyl]amino]thioxomethyl]-3,4,5-methoxy-benzamide (compound 1);
N-[[[3-(2-chloro-benzoyl amino)phenyl]amino]thioxomethyl]-3,4,5-methoxy-benzamide (compound 2);
N-[[[3-(3-methoxy-benzoylamino)phenyl]amino]thioxomethyl]-3,4,5-methoxy-benzamide (compound 3);
N-[[[3-(2-methoxy-benzoylamino)phenyl]amino]thioxomethyl]-3,4,5-methoxy-benzamide (compound 4);
N-[[[3-(4-methoxy-benzoylamino)phenyl]amino]oxomethyl]-3,4,5-methoxy-benzamide (compound 6);
N-[[[3-(4-pyridocarboxylamino)phenyl]amino]thioxomethyl]-3,4,5-methoxy-benzamide (compound 11);
N-[[[3-(4-chloro-benzoylamino)phenyl]amino]thioxomethyl]-3,4,5-methoxy-benzamide (compound 13);
N-[[[3-(isopropoylcarboxylamino))phenyl]amino]oxomethyl]-3,4,5-methoxy-benzamide (compound 17);
N-[[[3-(benzoylamino)phenyl]amino]thioxomethyl]-3,5-methoxy-benzamide (compound 18);
N-[[[3-(benzoylamino)phenyl]amino]thioxomethyl]-3,5-methoxy-4-ethoxy-benzamide (compound 19);
N-[[[3-(benzoylamino)phenyl]amino]thioxomethyl]-3,4-ethoxy-5-methoxy-benzamide (compound 20);
N-[[[3-(benzoylamino)phenyl]amino]thioxomethyl]-3,4,5-ethoxy-benzamide (compound 23);
N-[[[4-fluoro-3-(benzoylamino)phenyl]amino]thioxomethyl]-3,4,5-methoxy-benzamide (compound 24);
N-[[[4-chloro-3-(phenylamino)carbonyl]amino]thioxomethyl]-3,4,5-methoxy-benzamide (compound 25);
N-[[[3-(benzoylamino)phenyl]amino]oxomethyl]-3,4,5-methoxy-benzamide (compound 31);
N-[[[4-chloro-3-(benzoylamino)phenyl]amino]thioxomethyl]-3,4,5-methoxy-benzamide (compound 34);
N-[[[3-(benzoylamino)phenyl]amino]thioxomethyl]-3,4,5-methoxy-benzamide (compound 38);
N-[[[4-chloro-3-(4-dimethylamino-phenylamino)carbonyl]thioxomethyl]-3,4,5-methoxy-benzamide (compound 39);
N-[[[4-chloro-3-(4-chloro-phenylamino)]carbonyl]phenylamino]thioxomethyl]-3,4,5-methoxy-benzamide (compound 43);

N-[[[2-methyl-3-(benzoylamino)phenyl]amino]oxomethyl]-3,4,5-methoxy-benzamide (compound 45);

N-[[[-3-(4-chloro-benzoylamino)phenyl]amino]oxomethyl]-3,4,5-methoxy-benzamide (compound 47).

17. The method of claim 12, wherein:

Y represents a —NH—(C=O)—$R_6$ group wherein $R_6$ represents a non-substituted aryl group; an aryl group comprising one or more substituents selected from a halogen atom and an alkyl, alkoxy or mono- or dialkylamino radical; a mono- or polycyclic heteroaryl group; a linear or branched alkyl radical; or a saturated or unsaturated mono- or polycyclic hydrocarbon group; and when Y represents a —NH—(C=O)—$R_6$, X represents a sulfur atom.

18. The method of claim 12, wherein the compounds with formula (I) are selected from the group consisting of:

N-[[[3-(4-methoxy-benzoylamino)phenyl]amino]thioxomethyl]-3,4,5-methoxy-benzamide (I-a) with the following formula:

(compound 1)

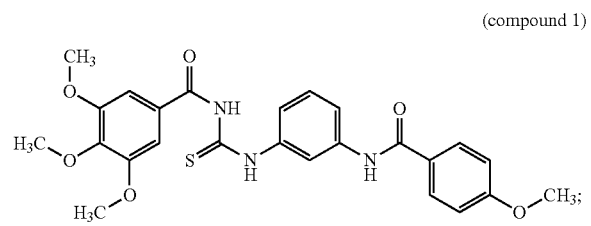 [SMILES: COc1ccc(C(=O)Nc2cccc(NC(=S)NC(=O)c3cc(OC)c(OC)c(OC)c3)c2)cc1]

N-[[[3-(2-chloro-benzoylamino)phenyl]amino]thioxomethyl]-3,4,5-methoxy-benzamide (I-a) with the following formula:

(compound 2)

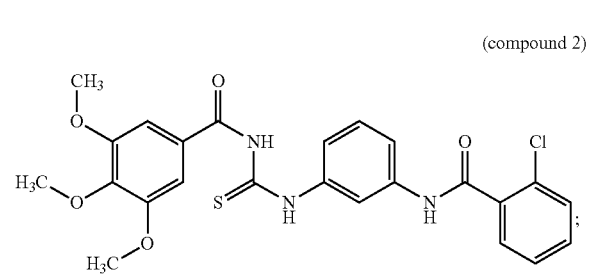 [SMILES: COc1cc(C(=O)NC(=S)Nc2cccc(NC(=O)c3ccccc3Cl)c2)cc(OC)c1OC]

N-[[[3-(3-methoxy-benzoylamino)phenyl]amino]thioxomethyl]-3,4,5-methoxy-benzamide (I-a) with the following formula:

(compound 3)

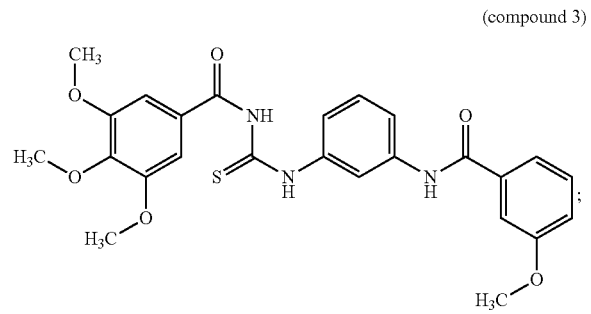 [SMILES: COc1cccc(C(=O)Nc2cccc(NC(=S)NC(=O)c3cc(OC)c(OC)c(OC)c3)c2)c1]

N-[[[3-(2-methoxy-benzoylamino)phenyl]amino]thioxomethyl]-3,4,5-methoxy-benzamide (I-a) with the following formula:

(compound 4)

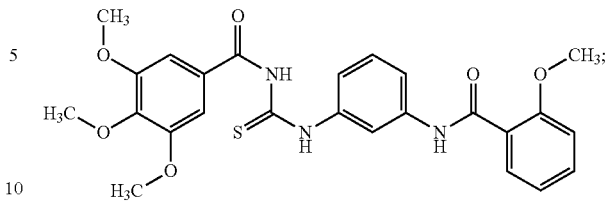

N-[[[3-(4-phenyl-benzoylamino)phenyl]amino]thioxomethyl]-3,4,5-methoxy-benzamide (I-a) with the following formula:

(compound 5)

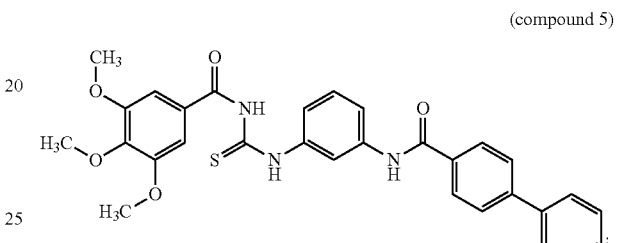

N-[[[3-(-cyclohexylcarboxylamino)phenyl]amino]thioxomethyl]-3,4,5-methoxy-benzamide (I-a) with the following formula:

(compound 8)

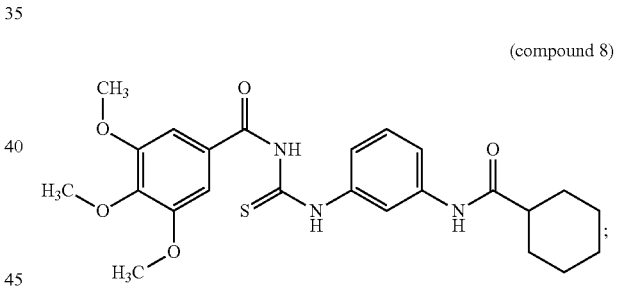

N-[[[3-(2-naphthoylamino)phenyl]amino]thioxomethyl]-3,4,5-methoxy-benzamide (I-a) with the following formula:

(compound 9)

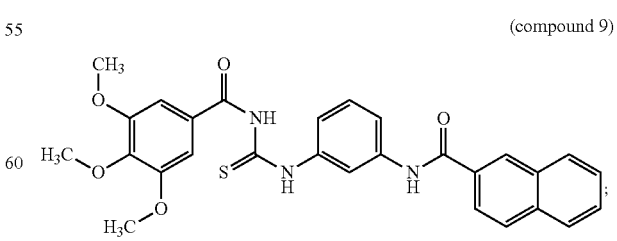

N-[[[3-(isopropoylcarboxylamino)phenyl]amino]thioxomethyl]-3,4,5-methoxy-benzamide (I-a) with the following formula:

(compound 10)

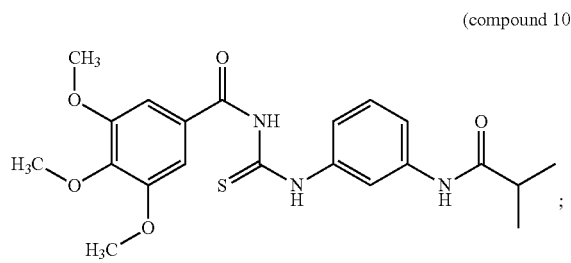

N-[[[3-(4-pyridocarboxylamino)phenyl]amino]thioxomethyl]-3,4,5-methoxy-benzamide (I-a) with the following formula:

(compound 11)

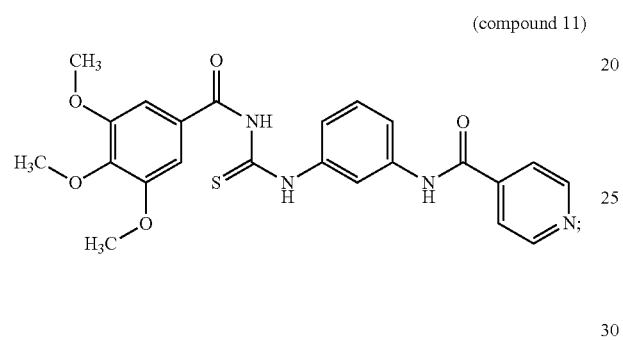

N-[[[3-(1-naphthoylamino)phenyl]amino]thioxomethyl]-3,4,5-methoxy-benzamide (I-a) with the following formula:

(compound 12)

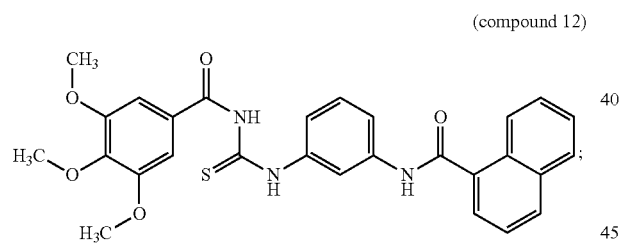

N-[[[3-(4-chloro-benzoylamino)phenyl]amino]thioxomethyl]-3,4,5-methoxy-benzamide (I-a) with the following formula:

(compound 13)

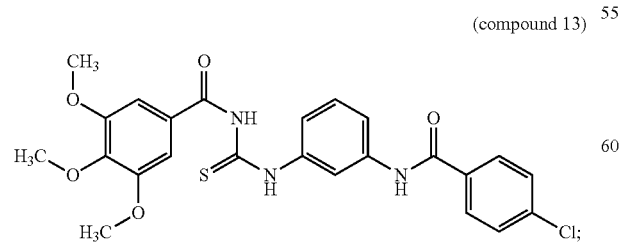

N-[[[3-(2-furoylamino)phenyl]amino]thioxomethyl]-3,4,5-methoxy-benzamide (I-a) with the following formula:

(compound 14)

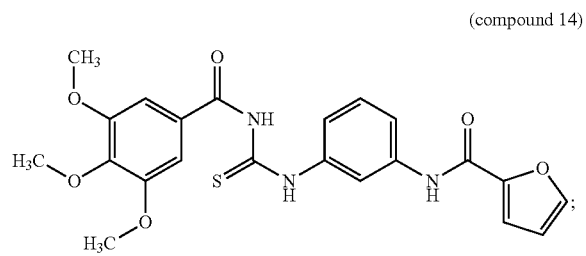 [SMILES: COc1cc(C(=O)NC(=S)Nc2cccc(NC(=O)c3ccco3)c2)cc(OC)c1OC]

N-[[[3-(2-thiophenoylamino)phenyl]amino]thioxomethyl]-3,4,5-methoxy-benzamide (I-a) with the following formula:

(compound 15)

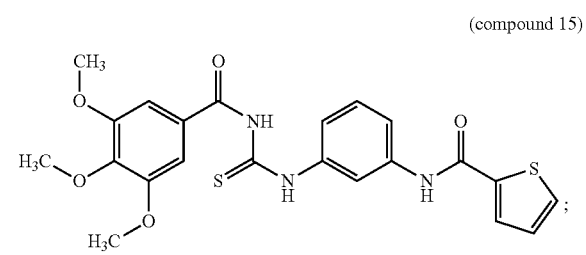 [SMILES: COc1cc(C(=O)NC(=S)Nc2cccc(NC(=O)c3cccs3)c2)cc(OC)c1OC]

N-[[[3-(benzoylamino)phenyl]amino]thioxomethyl]-3,5-methoxy-benzamide (I-a) with the following formula:

(compound 18)

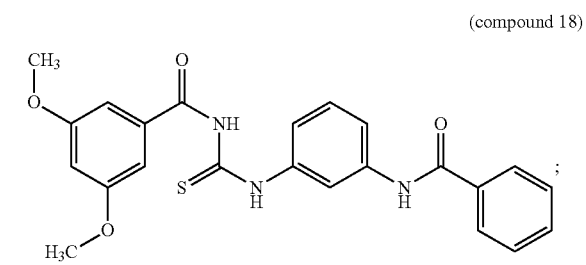 [SMILES: COc1cc(OC)cc(C(=O)NC(=S)Nc2cccc(NC(=O)c3ccccc3)c2)c1]

N-[[[3-(benzoylamino)phenyl]amino]thioxomethyl]-3,5-methoxy-4-ethoxy-benzamide (I-a) with the following formula:

(compound 19)

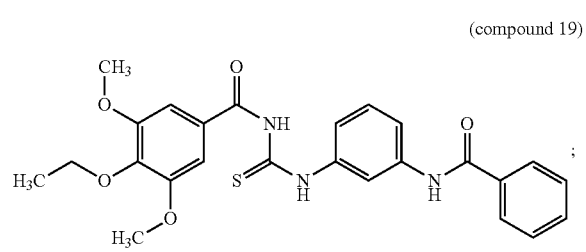 [SMILES: CCOc1c(OC)cc(C(=O)NC(=S)Nc2cccc(NC(=O)c3ccccc3)c2)cc1OC]

N-[[[3-(benzoylamino)phenyl]amino]thioxomethyl]-3,4-ethoxy-5-methoxy-benzamide (I-a) with the following formula:

(compound 20)

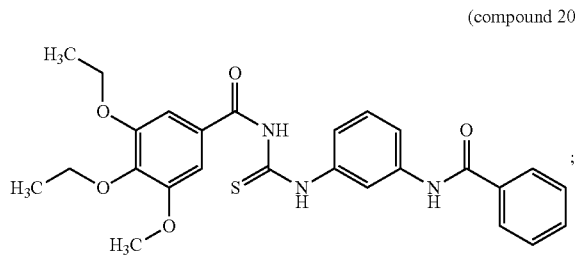

N-[[[3-(benzoylamino)phenyl]amino]thioxomethyl]-2,4-methoxy-benzamide (I-a) with the following formula:

(compound 22)

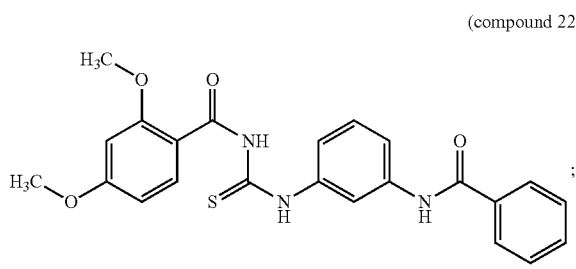

N-[[[3-(benzoylamino)phenyl]amino]thioxomethyl]-3,4,5-ethoxy-benzamide (I-a) with the following formula:

(compound 23)

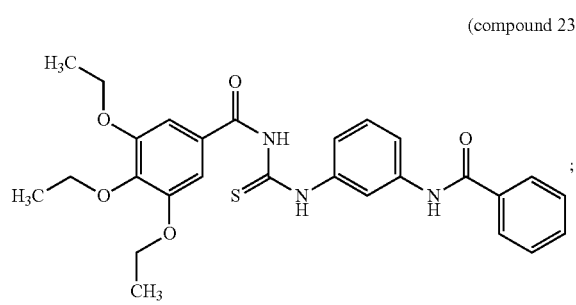

N-[[[4-fluoro-3-(benzoylamino)phenyl]amino]thioxomethyl]-3,4,5-methoxy-benzamide (I-a) with the following formula:

(compound 24)

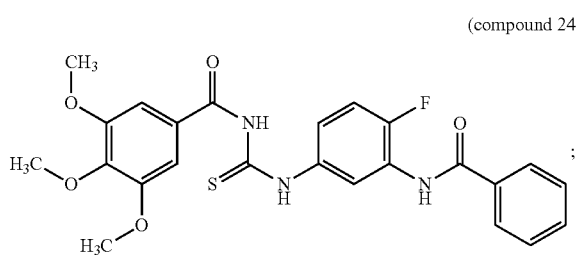

N-[[[4-methoxy-3-(benzoylamino)phenyl]amino]thioxomethyl]-3,4,5-methoxy-benzamide (I-a) with the following formula:

(compound 26)

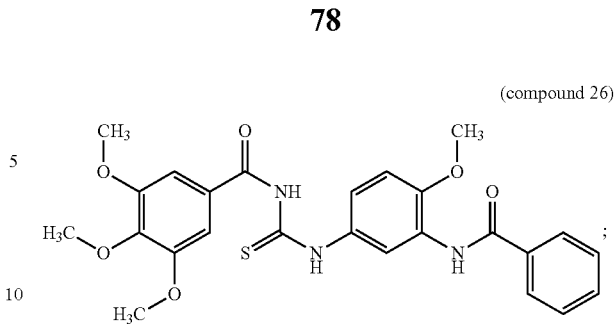

N-[[[4-methyl-3-(benzoylamino)phenyl]amino]thioxomethyl]-3,4,5-methoxy-benzamide (I-a) with the following formula:

(compound 27)

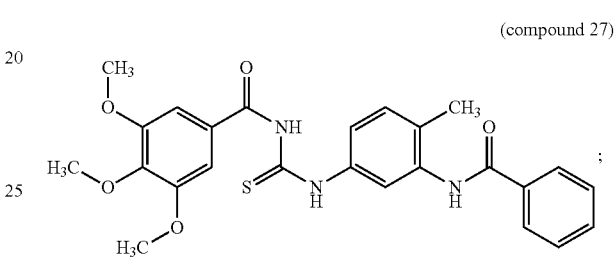

N-[[[3-methyl-3-(benzoylamino)phenyl]amino]thioxomethyl]-3,4,5-methoxy-benzamide (I-a) with the following formula:

(compound 32)

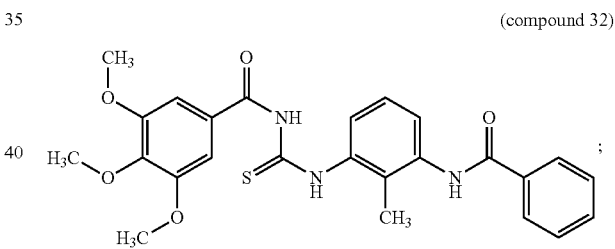

N-[[[4-chloro-3-(benzoylamino)phenyl]amino]thioxomethyl]-3,4,5-methoxy-benzamide (I-a) with the following formula:

(compound 34)

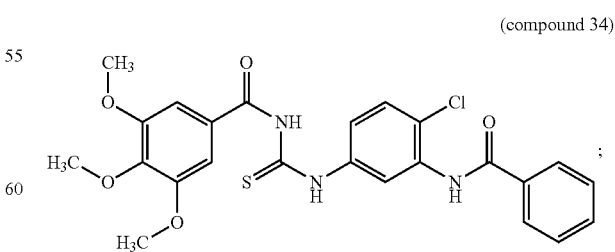

N-[[[5-chloro-3-(benzoylamino)phenyl]amino]thioxomethyl]-3,4,5-methoxy-benzamide (I-a) with the following formula:

(compound 35)

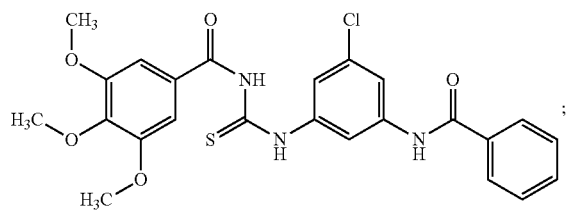

N-[[[5-fluoro-3-(benzoylamino)phenyl]amino]thioxomethyl]-3,4,5-methoxy-benzamide (I-a) with the following formula:

(compound 36)

N-[[[3-(benzoylamino)phenyl]amino]thioxomethyl]-3,4,5-methoxy-benzamide (I-a) with the following formula:

(compound 38)

N-[[[2-methyl-3-(benzoylamino)phenyl]amino]thioxomethyl]-3,4,5-methoxy-benzamide (I-a) with the following formula:

(compound 46)

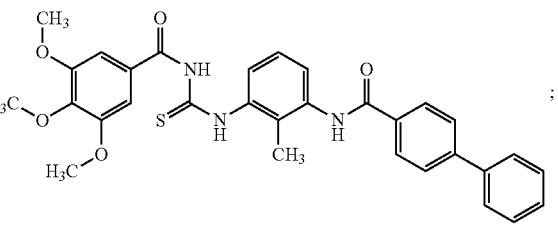

19. The method of claim 12, wherein the compounds with formula (I) are selected from the group consisting of:
N-[[[3-(4-methoxy-benzoylamino)phenyl]amino]thioxomethyl]-3,4,5-methoxy-benzamide (compound 1);
N-[[[3-(2-chloro-benzoylamino)phenyl]amino]thioxomethyl]-3,4,5-methoxy-benzamide (compound 2);
N-[[[3-(3-methoxy-benzoylamino)phenyl]amino]thioxomethyl]-3,4,5-methoxy-benzamide (compound 3);
N-[[[3-(2-methoxy-benzoylamino)phenyl]amino]thioxomethyl]-3,4,5-methoxy-benzamide (compound 4);
N-[[[3-(4-pyridocarboxylamino)phenyl]amino]thioxomethyl]-3,4,5-methoxy-benzamide (compound 11);
N-[[[3-(4-chloro-benzoylamino)phenyl]amino]thioxomethyl]-3,4,5-methoxy-benzamide (compound 13);
N-[[[3-(benzoylamino)phenyl]amino]thioxomethyl]-3,5-methoxy-benzamide (compound 18);
N-[[[3-(benzoylamino)phenyl]amino]thioxomethyl]-3,5-methoxy-4-ethoxy-benzamide (compound 19);
N-[[[3-(benzoylamino)phenyl]amino]thioxomethyl]-3,4-ethoxy-5-methoxy-benzamide (compound 20);
N-[[[3-(benzoylamino)phenyl]amino]thioxomethyl]-3,4,5-ethoxy-benzamide (compound 23);
-N-[[[4-fluoro-3-(benzoylamino)phenyl]amino]thioxomethyl]-3,4,5-methoxy-benzamide (compound 24);
N-[[[4-chloro-3-(benzoylamino)phenyl]amino]thioxomethyl]-3,4,5-methoxy-benzamide (compound 34);
N-[[[3-(benzoylamino)phenyl]amino]thioxomethyl]-3,4,5-methoxy-benzamide (compound 38).

\* \* \* \* \*

UNITED STATES PATENT AND TRADEMARK OFFICE
CERTIFICATE OF CORRECTION

| | | |
|---|---|---|
| PATENT NO. | : 9,073,835 B2 | Page 1 of 1 |
| APPLICATION NO. | : 12/988975 | |
| DATED | : July 7, 2015 | |
| INVENTOR(S) | : Martial Ruat et al. | |

It is certified that error appears in the above-identified patent and that said Letters Patent is hereby corrected as shown below:

IN THE CLAIMS

Column 45, Line 50, "N-[[[3-(benzoylamino)phenyl]amino]thioxomethyl]-3,4,5-ethoxy-benzamide (I-a')" should read -- N-[[[3-(benzoylamino)phenyl]amino]oxomethyl]-3,4,5-ethoxy-benzamide (I-a') --.

Column 50, Line 56, delete "; N-(3-(1H-indol-2-yl)phenylcarbamoyl)-3,4,5-trimethoxybenzamide (I-d') with formula".

Column 58, Line 59, delete "; N-(3-(1H-indol-2-yl)phenylcarbamoyl)-3,4,5-trimethoxybenzamide (I-d') with formula".

Column 59, line 22, "N-[R3-(benzoylamino)phenyl]amino]thioxomethyl]-3,4,5-methoxy-benzamide" should read -- N-[[[3-(benzoylamino)phenyl]amino]thioxomethyl]-3,4,5-methoxy-benzamide --.

Column 65, Line 50, "N-[[3-(benzoylamino)phenyl]amino]thioxomethyl]-2,4-methoxy-benzamide (I-a)" should read -- N-[[[3-(benzoylamino)phenyl]amino]thioxomethyl]-2,4-methoxy-benzamide (I-a) --.

Signed and Sealed this
Eighth Day of December, 2015

Michelle K. Lee
*Director of the United States Patent and Trademark Office*